US009029136B2

(12) United States Patent
Heidtman et al.

(10) Patent No.: US 9,029,136 B2
(45) Date of Patent: May 12, 2015

(54) ALPHA (1,2) FUCOSYLTRANSFERASES SUITABLE FOR USE IN THE PRODUCTION OF FUCOSYLATED OLIGOSACCHARIDES

(75) Inventors: Matthew Ian Heidtman, Brighton, MA (US); Massimo Merighi, Somerville, MA (US); John M. McCoy, Reading, MA (US)

(73) Assignee: Glycosyn LLC, Waltham, MA (US)

(*) Notice: Subject to any disclaimer, the term of this patent is extended or adjusted under 35 U.S.C. 154(b) by 0 days.

(21) Appl. No.: 13/557,655

(22) Filed: Jul. 25, 2012

(65) Prior Publication Data
US 2014/0031541 A1 Jan. 30, 2014

(51) Int. Cl.
| C12N 1/21 | (2006.01) |
| C07H 3/06 | (2006.01) |
| C12N 15/63 | (2006.01) |
| C12P 19/18 | (2006.01) |
| C12N 9/10 | (2006.01) |
| C12N 15/72 | (2006.01) |

(52) U.S. Cl.
CPC ............. *C12N 9/1051* (2013.01); *C12N 15/72* (2013.01)

(58) Field of Classification Search
CPC ...... C12N 15/72; C12N 9/1051; C12P 19/18; C12Y 204/01069
USPC .................. 536/123.1; 435/252.33, 320.1, 97
See application file for complete search history.

(56) References Cited

U.S. PATENT DOCUMENTS

| 6,656,714 | B2 | 12/2003 | Holmes et al. |
| 7,214,517 | B2 | 5/2007 | Kamada et al. |
| 2004/0048331 | A1 | 3/2004 | Taylor et al. |
| 2004/0219553 | A1 | 11/2004 | Kamada et al. |
| 2008/0145899 | A1 | 6/2008 | Johnson et al. |
| 2012/0208181 | A1 | 8/2012 | Merighi et al. |

FOREIGN PATENT DOCUMENTS

EP 2479263 A1 7/2012

OTHER PUBLICATIONS

Zimbro et al. Difco "& BBL" Manual, second edition. 2009.*
Xu et al. Evolution of Symbiotic Bacteria in the Distal Human Intestine. PLos Biol 5(7): E156, 2007 (GenBank Accession No. ABR40839).*
Snap Gene, pQE-80L Sequence and Map. http://www.snapgene.com/resources/plasmid_files/qiagen_vectors/pQE-80L/. Accessed on Apr. 14, 2014.*
Enequist et al. Energy is Required for Maturation of Exported Proteins in *Escherichia coli*. Eur J Biochem 116:227-233, 1981.*
Ebel et al. *Escherichia coli* RcsA, a Positive Activator of Colanic Acid Capsular Polysaccharide Synthesis, Functions to Activate Its Own Expression. J Bacteriol 181:577-584, 1999.*
Schallmey et al. "Developments in the Use of *Bacillus* Species for Industrial Production." *Can. J. Microbiol.* 50.1(2004):1-17.
Ward et al. "Human Milk Metagenome: A Functional Capacity Analysis." *BMC Microbiol.* 13(2013):116.
Mergaert et al. "Transfer of *Erwinia ananas* (Synonym, *Erwinia uredora*) and *Erwinia stewartii* to the Genus *Pantoea* emend. as *Pantoea ananas* (Serrano 1928) comb. nov. and *Pantoea stewartii* (Smith 1989) comb. nov., Respectively, and Description of *Pantoea stewartii* subsp. *indologenes* subsp. nov." *Int. J. Syst. Bacteriol.* 43.1(1993):162-173.
"E2DNL9." Oct. 30, 2012. Web. Apr. 1, 2014. <http://www.uniprot.org/uniprot/E2DNL9.txt?version=7>.
Westers et al. "*Bacillus subtilis* as Cell Factory for Pharmaceutical Proteins: A Biotechnological Approach to Optimize the Host Organism." *Biochim. Biophys. Acta.* 1694.1-3(2004):299-310.
Albermann et al. "Synthesis of the Milk Oligosaccharide 2'-Fucosyllactose Using Recombinant Bacterial Enzymes." *Carbohydr. Res.* 334.2(2001):97-103.
Amonsen et al. "Human Parainfluenza Viruses hPIV1 and hPIV3 Bind Oligosaccharides with a 2-3-Linked Sialic Acids That are Distinct From Those Bound by H5 Avian Influenza Virus Hemagglutinin." *J. Virol.* 81.15(2007):8341-8345.
Appelmelk et al. "Phase Variation in *Helicobacter pylori* Lipopolysaccharide." *Infect. Immun.* 66.1(1998):70-76.
Bachmann. "Pedigrees of Some Mutant Strains of *Escherichia coli* K-12." *Bacteriol. Rev.* 36.4(1972):525-557.
Belfort et al. "Characterization of the *Escherichia coli thyA* Gene and its Amplified Thymidylate Synthetase Product." *PNAS.* 80.7(1983):1858-1861.
Bettler et al. "The Living Factory: In vivo Production of N-Acetyllactosamine Containing Carbohydrates in *E. coli*." *Glycoconj. J.* 16.3(1999):205-212.
Bode. "Recent Advances on Structure, Metabolism, and Function of Human Milk Oligosaccharides." *J. Nutr.* 136.8(2006):2127-2130.
Charlwood et al. "A Detailed Analysis of Neutral and Acidic Carbohydrates in Human Milk." *Anal. Biochem.* 273.2(1999):261-277.
Chaturvedi et al. "Fucosylated Human Milk Oligosaccharides Vary Between Individuals and Over the Course of Lactation." *Glycobiol.* 11.5(2001):365-372.
Chaturvedi et al. "Survival of Human Milk Oligosaccharides in the Intestine of Infants." *Bioactive Components of Human Milk.* Newburg, ed. New York: Kluwer Academic/Plenum Publishers. Chapter 34 (2001):315-323.
Couceiro et al. "Influenza Virus Strains Selectively Recognize Sialyloligosaccharides on Human Respiratory Epithelium; The Role of the Host Cell in Selection of Hemagglutinin Receptor Specificity." *Virus Res.* 29.2(1993):155-165.
Court et al. "Genetic Engineering Using Homologous Recombination." *Annu. Rev. Genet.* 36(2002):361-388.
Cox et al. "Structural Analysis of the Lipopolysaccharide from *Vibrio cholerae* Serotype O22." *Carbohydr. Res.* 304.3-4(1997):191-208.

(Continued)

*Primary Examiner* — Brandon Fetterolf
*Assistant Examiner* — Yih-Horng Shiao
(74) *Attorney, Agent, or Firm* — Mintz Levin Cohn Ferris Glovsky and Popeo, P.C.; Ingrid A. Beattie

(57) ABSTRACT

The invention provides compositions and methods for engineering *E. coli* or other host production bacterial strains to produce fucosylated oligosaccharides, and the use thereof in the prevention or treatment of infection.

18 Claims, 7 Drawing Sheets

(56) References Cited

OTHER PUBLICATIONS

Coyne et al. "Human Symbionts Use a Host-Like Pathway for Surface Fucosylation." *Science.* 307.5716(2005):1778-1781.
Crout et al. "Glycosidases and Glycosyl Transferases in Glycoside and Oligosaccharide Synthesis." *Curr. Opin. Chem. Biol.* 2.1(1998):98-111.
Drouillard et al. "Large-Scale Synthesis of H-Antigen Oligosaccharides by Expressing *Helicobacter pylori* α1,2-Fucosyltransferase in Metabolically Engineered *Escherichia coli* Cells." *Angew Chem. Int. Ed. Engl.* 45.11(2006):1778-1780.
Dumon et al. "Assessment of the Two *Helicobacter pylori* α-1,3-Fucosyltranferase Ortholog Genes for the Large-Scale Synthesis of LewisX Human Milk Oligosaccharides by Metabolically Engineered *Escherichia coli.*" *Biotechnol. Prog.* 20.2(2004):412-419.
Dumon et al. "In vivo Fucosylation of lacto-*N*-neotetraose and lacto-*N*-neohexaose by Heterologous Expression of *Helicobacter pylori* α-1,3 Fucosylatransferase in Engineered *Escherichia coli.*" *Glycoconj. J.* 18.6(2001):465-474.
Dumon et al. "Production of Lewis x Tetrasaccharides by Metabolically Engineered *Escherichia coli.*" *Chembiochem.* 7.2(2006):359-365.
Endo et al. "Large-Scale Production of *N*-Acetyllactosamine Through Bacterial Coupling." *Carbohydr. Res.* 316.1-4(1999):179-183.
Endo et al. "Large-Scale Production of Oligosaccharides Using Engineered Bacteria." *Curr. Opin. Struct. Biol.* 10.5(2000):536-541.
Endo et al. "Large-Scale Production of the Carbohydrate Portion of the siayl-Tn Epitope, α-Neu$p$5Ac-(2→6)-D-Gal$p$NAc, Through Bacterial Coupling." *Carbohydr. Res.* 330.4(2001):439-443.
Endo et al. "Large-Scale Production of the CMP-NeuAc and Sialylated Oligosaccharides Through Bacterial Coupling." *Appl. Microbiol. Biotechnol.* 53.3(2000):257-261.
Flowers. "Chemical Synthesis of Oligosaccharides." *Methods Enzymol.* 50(1978):93-121.
GenBank Accession No. ADN43847, Sep. 25, 2010.
GenBank Accession No. BAA33632, Oct. 16, 1999.
GenBank Accession No. CAH06753, Jul. 1, 2011.
GenBank Accession No. CAH09369, Jul. 1, 2011.
GenBank Accession No. NP_206893, Jul. 10, 2012.
GenBank Accession No. NP_206894, Jul. 10, 2012.
GenBank Accession No. U16857.1, May 24, 1995.
GenBank Accession No. YP_001300461, Jan. 26, 2012.
GenBank Accession No. YP_003500093, Feb. 14, 2012.
GenBank Accession No. YP_003517185, Jan. 26, 2012.
GenBank Accession No. ZP_02065239, Nov. 9, 2010.
GenBank Accession No. ZP_04580654, Jun. 9, 2010.
GenBank Accession No. ZP_07805473, Dec. 1, 2010.
Gottesman et al. "Regulation of Capsular Polysaccharide Synthesis in *Escherichia coli* K12." *Mol. Microbiol.* 5.7(1991):1599-1606.
Hamosh. "Bioactive Factors in Human Milk." *Pediatr. Clin. North Am.* 48.1(2001):69-86.
Johnson. "Synthesis of Oligosaccharides by Bacterial Enzymes." *Glycoconj. J.* 16.2(1999):141-146.
Koeller et al. "Synthesis of Complex Carbohydrates and Glycoconjugates: Enzyme-Based and Programmable One-Pot Strategies." *Chem. Rev.* 100.12(2000):4465-4493.
Koizumi et al. "Large-Scale Production of UDP-Galactose and Globotriose by Coupling Metabolically Engineered Bacteria." *Nat. Biotechnol.* 16.9(1998):847-850.
Kuhlenschmidt et al. "Sialic Acid Dependence and Independence of Group A Rotaviruses." *Mechanisms in the Pathogenesis of Enteric Disases* 2. Paul et al., eds. New York: Springer Science Business Media. Chapter 33 (1999):309-317.
Kunz et al. "Oligosaccharides in Human Milk: Structural, Functional, and Metabolic Aspects." *Annu. Rev. Nutr.* 20(2000):699-722.
LaVallie et al. "A Thioredoxin Gene Fusion Expression System That Circumvents Inclusion Body Formation in the *E. coli* Cytoplasm." *Biotechnol.* 11.2(1993):187-193.
LaVallie et al. "Thioredoxin as a Fusion Partner for Production of Soluble Recombinant Proteins in *Escherichia coli.*" *Methods Enzymol.* 326(2000):322-340.
Li et al. "Characterization of a Novel α1,2-Fucosyltransferase of *Escherichia coli*O128:B12 and Functional Investigation of its Common Motif." *Biochemistry.* 47.1(2008):378-387.
Mahdavi et al. "*Helicobacter pylori* SabA Adhesin in Persistent Infection and Chronic Inflammation." *Science.* 297.5581(2002):573-578.
Marcobal et al. "Consumption of Human Milk Oligosaccharides by Gut-Related Microbes." *J. Agric. Food Chem.* 58.9(2010):5334-5340.
Martin-Sosa et al. "Sialyligosaccharides in Human and Bovine Milk and in Infant Formulas: Variations with the Progression of Lactation." *J. Dairy Sci.* 86.1(2003):52-59.
Mieschendahl et al. "A Nogel Prophage Independent *TRP* Regulated Lambda PL Expression System." *Nat. Biotechnol.* 4(1986):802-808.
Morrow et al. "Human Milk Oligosaccharides are Associated with Protection Against Diarrhea in Breast-Fed Infants." *J. Pediatr.* 145.3(2004):297-303.
Newburg et al. "Human Milk Glycans Protect Infants Against Enteric Pathogens." *Annu. Rev. Nutr.* 25(2005):37-58.
Newburg et al. "Innate Protection Conferred by Fucosylated Oligosaccharides of Human Milk Against Diarrhea in Breastfed Infants." *Glycobiol.* 14.3(2004):253-263.
Newburg et al. "Protection of the Neonate by the Innate Immune System of Developing Gut and of Human Milk." *Pediatr. Res.* 61.1(2007):2-8.
Newburg et al. "Role of Human-Milk Lactadherin in Protection Against Symptomatic Rotavirus Infection." *Lancet.* 351.9110(1998):1160-1164.
Newburg. "Bioactive Components of Human Milk: Evolution, Efficiency, and Protection." *Bioactive Components of Human Milk.* Newburg, ed. New York: Kluwer Academic/Plenum Publishers. Chapter 1 (2001):3-10.
Newburg. "Human Milk Gylcoconjugtes That Inhibit Pathogens." *Curr. Med. Chem.* 6.2(1999):117-127.
Ninoneuvo et al. "A Strategy for Annotating the Human Milk Glycome." *J. Agric. Food Chem.* 54.20(2006):7471-7480.
Palcic. "Biocatalytic Synthesis of Oligosaccharides." *Curr. Opin. Biotechnol.* 10.6(1999):616-624.
Parkkinen et al. "Isolation of Sialyl Oligosaccharides and Sialyl Oligosaccharide Phosphates From Bovine Colostrum and Human Urine." *Methods Enzymol.* 138(1987):289-300.
Ruffing et al. "Metabolic Engineering of Microbes for Oligosaccharide and Polysaccharide Synthesis." *Microb. Cell Fact.* 5(2006):25.
Ruiz-Palacios et al. "*Campylobacter jejuni* Binds Intestinal H(O) Antigen (Fucα1, 2Galβ1, 4GlcNAc), and Fucosyloligosaccharides of Human Milk Inhibit its Binding and Infection." *J. Biol. Chem.* 278.16(2003):14112-14120.
Rydell et al. "Human Noroviruses Recognize Sialyl Lewis x Neoglycoprotein." *Glycobiol.* 19.3(2009):309-320.
Scharfman et al. "Sialyl-Lex and Sulfo-Sialyl-Lex Determinants are Receptors for *P. aeruginosa.*" *Glycoconj. J.* 17.10(2000):735-740.
Seeberger. "Automated Carbohydrate Synthesis to Drive Chemical Glycomics." *Chem. Commun. (Camb.).* 10(2003):1115-1121.
Shen et al. "Resolution of Structural Isomers of Sialylated Oligosaccharides by Capillary Electrophoresis." *J. Chromatogr. A.* 921.2(2001):315-321.
Stevenson et al. "Organization of the *Escherichia coli* K-12 Gene Cluster Responsible for Production of the Extracellular Polysaccharide Colanic Acid." *J. Bacteriol.* 178.16(1996):4885-4893.
Wymer et al. "Enzyme-Catalyzed Synthesis of Carbohydrates." *Curr. Opin. Chem. Biol.* 4.1(2000):110-119.
Yamasaki et al. "The Genes Responsible for O-Antigen Synthesis of *Vibrio cholerae* O139 are Closely Related to Those of *Vibrio cholerae* O22." *Gene.* 237.2(1999):321-332.

\* cited by examiner

US 9,029,136 B2

ALPHA (1,2) FUCOSYLTRANSFERASES SUITABLE FOR USE IN THE PRODUCTION OF FUCOSYLATED OLIGOSACCHARIDES

INCORPORATION-BY-REFERENCE OF SEQUENCE LISTING

The contents of the text file named "37847-510F01US_ST25.txt", which was created on Aug. 20, 2012 and is 71.1 KB in size, are hereby incorporated by reference in their entirety.

FIELD OF THE INVENTION

The invention provides compositions and methods for producing purified oligosaccharides, in particular certain fucosylated oligosaccharides that are typically found in human milk.

BACKGROUND OF THE INVENTION

Human milk contains a diverse and abundant set of neutral and acidic oligosaccharides. More than 130 different complex oligosaccharides have been identified in human milk, and their structural diversity and abundance is unique to humans. Although these molecules may not be utilized directly by infants for nutrition, they nevertheless serve critical roles in the establishment of a healthy gut microbiome, in the prevention of disease, and in immune function. Prior to the invention described herein, the ability to produce human milk oligosaccharides (HMOS) inexpensively was problematic. For example, their production through chemical synthesis was limited by stereo-specificity issues, precursor availability, product impurities, and high overall cost. As such, there is a pressing need for new strategies to inexpensively manufacture large quantities of HMOS.

SUMMARY OF THE INVENTION

The invention features an efficient and economical method for producing fucosylated oligosaccharides. Such production of a fucosylated oligosaccharide is accomplished using an isolated nucleic acid comprising a sequence encoding a lactose-utilizing α(1,2) fucosyltransferase gene product (e.g., polypeptide or protein), which is operably linked to one or more heterologous control sequences that direct the production of the recombinant fucosyltransferase gene product in a bacterium such as *Escherichia coli* (*E. coli*). In one example, the bacterium is an enteric bacterium. The amino acid sequence of the lactose-accepting α(1,2)fucosyltransferase gene product is preferably at least 10% and less than 40% identical to FutC (SEQ ID NO:2).

Also within the invention is a nucleic acid construct comprising an isolated nucleic acid encoding a lactose-accepting α(1,2)fucosyltransferase enzyme, said nucleic acid being operably linked to one or more heterologous control sequences that direct the production of the enzyme in a host bacteria production strain, wherein the amino acid sequence of the gene product (enzyme) encoded by the nucleic acid comprises about 70% identity to SEQ ID NO:2. For example, the construct comprises SEQ ID NO: 7, which encodes a FutL protein. By "heterologous" is meant that the control sequence and protein-encoding sequence originate from different bacterial strains. A suitable production host bacterial strain is one that is not the same bacterial strain as the source bacterial strain from which the fucosyltransferase-encoding nucleic acid sequence was identified.

A method for producing a fucosylated oligosaccharide, e.g., an HMOS, in a bacterium is carried out by providing a bacterium such as a production host strain, *Escherichia coli* (*E. coli*), that is characterized by a reduced level of β-galactosidase activity, a defective colonic acid synthesis pathway, a mutation in an ATP-dependent intracellular protease, a mutation in a lacA gene and an exogenous α(1,2)fucosyltransferase gene. Preferably, a mutation in a thyA gene in the host bacterium allows for the maintenance of plasmids that carry thyA as a selectable marker gene. Exemplary alternative selectable markers include antibiotic resistance genes such as BLA (beta-lactamase), or proBA genes (to complement a proAB host strain proline auxotropy) or purC (to complement a purC host strain adenine auxotrophy). The bacterium comprising these characteristics is cultured in the presence of lactose, and a fucosylated oligosaccharide is retrieved from the bacterium or from a culture supernatant of the bacterium. In some cases, the method further comprises culturing the bacterium in the presence of tryptophan and in the absence of thymidine. In preferred embodiments, the production host strain comprises *E. coli* K12. Other production host organisms are listed below.

The invention provides a purified fucosylated oligosaccharide produced by the methods described herein. The fucosylated oligosaccharide is purified for use in therapeutic or nutritional products, or the bacterium is used directly in such products. The fucosylated oligosaccharide produced by the engineered bacterium is 2'-fucosyllactose (2'-FL) or lactodifucotetraose (LDFT). The new alpha 1,2-fucosyltransferases are also useful to synthesize HMOS of larger molecular weight bearing alpha 1,2 fucose moieties, e.g., lacto-N-fucopentaose (LNF I) and lacto-N-difucohexaose (LDFH I).

The bacterium used to produce the oligosaccharides is genetically engineered to comprise an increased intracellular guanosine diphosphate (GDP)-fucose pool (compared to wild type), an increased intracellular lactose pool (compared to wild type), and to comprise fucosyltransferase activity. Accordingly, an endogenous lacZ gene and an endogenous lacI gene of the *E. coli* are deleted or functionally inactivated to reduce the level of β-galactosidase activity. The bacterium may also comprise a mutation in the lacA gene. The isolated *E. coli* bacterium also comprises a lacIq gene promoter immediately upstream of a lacY gene. In some cases, the isolated *E. coli* bacterium comprises a defective colonic acid synthesis pathway due to an endogenous wcaJ gene of the *E. coli* being deleted or functionally inactivated. The bacterium comprises a mutation in an adenosine-5'-triphosphate (ATP)-dependant intracellular protease. For example, the bacterium comprises a null mutation in a ion gene. The bacterium also comprises a mutation in a thyA gene. Preferably, the bacterium accumulates an increased intracellular lactose pool and an increased intracellular GDP-fucose pool. In one aspect, the *E. coli* bacterium comprises the genotype ΔampC::$P_{trp}^{B}$cI, Δ(lacI-lacZ)::FRT, $P_{lacIq}$lacY$^+$, ΔwcaJ::FRT, thyA::Tn10, Δlon:(npt3, lacZ$^+$), ΔlacA.

The bacterium possesses fucosyl transferase activity. For example, the bacterium comprises an exogenous α(1,2)fucosyltransferase gene. Preferably, the exogenous α(1,2) fucosyltransferase gene comprises at least 10% homology/identity and less than 40% at the amino acid level to *Helicobacter pylori* 26695 alpha-(1,2)fucosyltransferase (futC), e.g., at least 15%, at least 20%, at least 25%, at least 30% identity. In other examples, the sequences are at least 50%, at least 55%, at least 60%, at least 65%, at least 70%, at least 75%, at least 80%, at least 85%, at least 90%, at least 95% homology/ identity to *Helicobacter pylori* 26695 alpha-(1,2)fucosyltransferase (futC). In one example, FutL is 70% identical to FutC at the amino acid level.

The term "% identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For example, % identity is relative to the entire length of the coding regions of the sequences being compared.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Percent identity is determined using search algorithms such as BLAST and PSI-BLAST (Altschul et al., 1990, J Mol Biol 215:3, 403-410; Altschul et al., 1997, Nucleic Acids Res 25:17, 3389-402). For the PSI-BLAST search, the following exemplary parameters are employed: (1) Expect threshold was 10; (2) Gap cost was Existence:11 and Extension:1; (3) The Matrix employed was BLOSUM62; (4) The filter for low complexity regions was "on". The bacterium expresses a fucosyltransferase gene product encoded by a sequence that is not identical to futC.

Exemplary α(1,2)fucosyltransferase genes include *Escherichia coli* O126 wbgL, *Helicobacter mustelae* 12198 (ATCC 43772) alpha-1,2-fucosyltransferase (futL), and *Bacteroides vulgatus* ATCC 8482 glycosyl transferase family protein (futN). An exogenous α(1,2)fucosyltransferase gene is selected from the group consisting of *Escherichia coli* O126 wbgL, *Helicobacter mustelae* 12198 (ATCC 43772) alpha-1,2-fucosyltransferase (futL), *Bacteroides vulgatus* ATCC 8482 glycosyl transferase family protein (futN), *Bacteroides fragilis* (NCTC) 9343 fucosyl transferase (bft3/wcfB), *Escherichia coli* O55:H7 (str. CB9615)fucosyltransferase (wbgN), *Helicobacter bilis* ATCC 437879 futD, *Vibrio cholera* O22 wblA, *Bacteroides fragilis* (NCTC) 9343 alpha-1,2-fucosyltransferase (bft1), *Bacteroides ovatus* ATCC 8483 futO, and *Helicobacter cinaedi* CCUG 18818 alpha-1,2-fucosyltransferase (futE).

The invention also features a vector, e.g., a vector containing a nucleic acid. The vector can further include one or more regulatory elements, e.g., a heterologous promoter. The regulatory elements can be operably linked to a gene encoding a protein, a gene construct encoding a fusion protein gene, or a series of genes linked in an operon in order to express the fusion protein. In yet another aspect, the invention comprises an isolated recombinant cell, e.g., a bacterial cell containing an aforementioned nucleic acid molecule or vector. The nucleic acid is optionally integrated into the genome.

Also provided is a nucleic acid construct comprising at least one of a promoter of bacteriophage λ, an *E. coli* rcsA gene, a bla gene, and a native thyA gene. As an example of such a construct, the plasmid map of pG171 in FIG. 5.

The sequence of pG171 is set forth below with annotations from GenBank regarding specific features (SEQ ID NO: 1):

```
LOCUS           pEC2-futC-MYC-rcsA-thyA_(pG171)           6244 bp DNA
circular SYN 24-MAY-1995
DEFINITION      Fusion cloning vector pTRXFUS, complete sequence.
ACCESSION       U16857
VERSION         U16857.1 GI:575447
KEYWORDS        thioredoxin gene fusion vector.
SOURCE          Cloning vector pTRXFUS (unknown)
  ORGANISM      Cloning vector pTRXFUS
                other sequences; artificial sequences; vectors.
REFERENCE       1 (bases 1 to 3585)
  AUTHORS       LaVallie,E.R., DiBlasio,E.A., Kovacic,S., Grant,K.L.,
Schendel,P.F.
                and McCoy,J.M.
  TITLE         A thioredoxin gene fusion expression system that circumvents
                inclusion body formation in the E. coli cytoplasm
  JOURNAL       Biotechnology (N.Y.) 11 (2), 187-193 (1993)
   PUBMED       7763371
REFERENCE       2 (bases 1 to 3585)
  AUTHORS       LaVallie,E.R.
  TITLE         Direct Submission
  JOURNAL       Submitted (03-NOV-1994) Edward R. LaVallie, Genetics Institute, 87
                CambridgePark Drive, Cambridge, MA 02140, USA
FEATURES             Location/Qualifiers
     Primer          163..183
                     /label=lacZR6
     CDS             243..481
                     /gene="lgt"
                     /note="ECK2824:JW2796:b2828"
                     /codon_start=1
                     /transl_table=11
                     /product="phosphatidylglycerol-
prolipoproteindiacylglyceryl
                     transferase"
                     /protein_id="BAE76897.1"
                     /db_xref="GI:85675644"
```

```
                         /translation="MTSSYLHFPEFDPVIFSIGPVALHWYGLMYLVGFIFAMWLATRRA
                         NRPGSGWTKNEVENLLYAGFLGVFLGGRIGYVLFYNFPQFMADPLYLFRVWDSFHG
GLIGVIVVMIIFARRTKRSFFQVSDFIAPLIPFGLGAGRLGNFINGELWGRVDPNFPFA
MLFPGSRTEDILLLQTNPQWQSIFDTYGVLPRHPSQLYELLLEGVVLFIILNLYIRKPR
         PMGAVSGLFLIGYGAFRIIVEFFRQPDAQFTGAWVQYISMGQILSIPMIVAGVIMMVA
YRRSPQQHVS"
     Source                complement(243..1365)
                           /organism="Escherichia coli W3110"
                           /mol_type="genomic DNA"
                           /strain="K-12"
                           /sub_strain="W3110"
                           /db_xref="taxon:316407"
                           /note="synonym: Escherichia coli str. K12 substr.
W3110"
     Source                complement(242^243)
                           /organism="Escherichia coli W3110"
                           /mol_type="genomic DNA"
                           /strain="K-12"
                           /sub_strain="W3110"
                           /db_xref="taxon:316407"
                           /note="synonym: Escherichia coli str. K12 substr.
W3110"
     Primer                243..266
                           /note=cagtcagtcaggcgccTCCTCAACCTGTATATTCGTAAAC
                           /label=THYA-F
     Promoter              359..364
                           /label="thyA -35"
     Promoter              380..385
                           /label="thyA WEAK -10"
     Binding_site          479..484
                           /label="thyA RBS"
     Gene                  488..1282
                           /gene="thyA"
     CDS                   488..1282
                           /gene="thyA"
                           /note="ECK2823:JW2795:b2827"
                           /codon_start=1
                           /transl_table=11
                           /product="thymidylate synthetase"
                           /protein_id="BAE76896.1"
                           /db_xref="GI:85675643"
         /translation="MKQYLELMQKVLDEGTQKNDRTGTGTLSIFGHQMRFNLQDGFPLV
                         TTKRCHLRSIIHELLWFLQGDTNIAYLHENNVTIWDEWADENGDLGPVYGKQWRTP
                         DGRHIDQITTVLNQLKNDPDSRRIIVSAWNVGELDKMALAPCHAFFQFYVADGKLSL
                         YQRSCDVFLGLPFNIASYALLVHMMAQQCDLEVGDFVWTGGDTHLYSNHMDQLSR
EPRPLPKLIIKRKPESIFDYRFEDFEIEGYDPHPGIKAPVAI"
     Hairpin_loop          1304..1310
                           /label=Terminator
     Hairpin_loop          1317..1323
                           /label=Terminator
     Primer                complement(1345..1365)
                           /note=cagtcagtcaggcgccTTCGGGAAGGCGTCTCGAAGA
                           /label=THYA-R
     Primer                complement(1468..1489)
                           /label=lacZF5
     Primer                1508..1524
                           /label=aspAseq
     Gene                  1536..1588
                           /gene="dsrB"
     Primer                1536..1558
                           /note=cagtcagtcaaagcttTCTTTAATGAAGCAGGGCATCAG
                           /label=rcsA-R
     Hairpin_loop          complement(1600..1610)
                           /label=Hairpin
     Hairpin_loop          complement(1615..1625)
                           /label=Hairpin
     CDS                   complement(1632..2255)
                           /gene="rcsA"
                           /note="ECK1949:JW1935:b1951"
                           /codon_start=1
                           /transl_table=11
                           /product="DNA-binding transcriptional co-regulator
withRcsB"
                           /protein_id="BAA15776.1"
                           /db_xref="GI:1736617"
         /translation="MSTIIMDLCSYTRLGLTGYLLSRGVKKREINDIETVDDLAIACDS
QRPSVVFINEDCFIHDASNSQRIKLIINQHPNTLFIVFMAIANVHFDEYLLVRKNLLIS
         SKSIKPESLDDILGDILKKETTITSFLNMPTLSLSRTESSMLRMWMAGQGTIQISDQMN
IKAKTVSSHKGNIKRKIKTHNKQVIYHVVRLTDNVTNGIFVNMR"
```

-continued

```
  Promoter              complement(2393..2398)
                        /label=-10
  Promoter              complement(2419..2424)
                        /label=-35
  Primer                complement(2473..2495)
                        /note=cagtcagtcaaagcttCTACGAACATCTTCCAGGATACT
                        /label=rcsA-F2
  Terminator            complement(2502..2571)
                        /note="aspA transcription terminator"
  Primer                complement(2553..2574)
                        /note=cagtcagtcaCTCGAGGCTGCAGTAATCGTACAGGGTAG
                        /label=PLvect2
  Primer_binding_       2575..2644
/PCR_primers=cagtcagtcactcgagtTTAattcaaatcttcttcagaaatcaatt
                        tttgttcAGCGTTATACTTTTGGGATTTTACCTC
                        /label="Primer 0011-futCMYC-4"
  CDS                   complement(2574^2575)
                        /note="Identical to previously sequenced to
                        BacteroidesfragilisSWALL:Q9F7604.3e-
123,coli(EMBL:AF461121)
                        id"
                        /transl_table=11
                        /product="putative LPS biosynthesis
                        relatedalpha-1,2-fucosyltransferase"
                        /gene=wcfW
                        /locus_tag=BF1902
                        /protein_id=CAH07600.1
/translation=MIVSSLRGGLGNQMFIYAMVKAMALRNNVPFAFNLTTDFANDEVYK
RKLLLSYFALDLPENKKLTFDFSYGNYYRRLSRNLGCHILHPSYRYICEERPPHFESRL
ISSKITNAFLEGYWQSEKYFLDYKQEIKEDFVIQKKLEYTSYLELEEIKLLDKNAIMIG
VRRYQESDVAPGGVLEDDYYKCAMDIMASKVTSPVFFCFSQDLEWVEKHLAGKYPVRLISKKEDDSGTIDDMFLM
MHFRNYIISNSSFYWWGAWLSKYDDKLVIAPGNFINKDSVPESWFKLNVR
  POLYLINKER            complement(2575..2580)
    Protein             complement(2578..2581)
                        /label="K.lactis alpha-factor leader"
    Gene                complement(2582..3055)
                        /locus_tag="HP0093"
                        /db_xref="GeneID:900162"
    CDS                 complement(2582..3517)
                        /label="futC strain 26695 (fixed)"
    Source              2582..3517
                        /organism="Helicobacter pylori 26695"
                        /mol_type="genomic DNA"
                        /strain="26695"
                        /db_xref="taxon:85962"
    MYC-tag             complement(2585..2617)
    Primer              2968..2990
                        /note=GATAGTCAATACCAAGCTGACAG
                        /label=3-6-R
    Primer              2968..2990
                        /label="42 (3-6-R)"
    Gene                complement(3052..3517)
                        /locus_tag="HP0094"
                        /db_xref="GeneID:899021"
    Primer              complement(3495..3517)
                        /note=GAAttcaagaaggagatataCATATGGCTTTTAAGGTGGTGCAAAT
                        /label=pLfutC-F
    Source              3517^3518
                        /organism="Escherichia coli W3110"
                        /mol_type="genomic DNA"
                        /strain="K-12"
                        /sub_strain="W3110"
                        /db_xref="taxon:316407"
                        /note="synonym: Escherichia coli str. K12 substr.
W3110"
    RBS                 complement(3521..3535)
                        /label="T7 gene 10 RBS"
    Source              complement(3541..3715)
                        /note="originates from LAMCG"
                        /label="lambda DNA"
    Primer              3541..3567
                        /note=cagtcagtcagaattcTAACAATTGATTGAATGTATGCAAATA
                        /label=pLnut-R
    Region              complement(3544)
                        /label="TR1 termination site"
    note                3544
                        /note="original sequenced pEC2-BfT2-MYC plasmid is a
                        mixture of C and A here. This plasmid is A"
```

```
        Misc._feature       complement(3547..3553)
                            /label="TR1 rho-dep consensus box"
        Region              complement(3566..3571)
                            /label="TR1 termination site"
        Misc._feature       complement(3580..3599)
                            /note="rho utilization site B (rutB)"
        Misc._binding       complement(3600..3616)
                            /note="N-utilization rightward; putative"
                            /bound_moiety="Nutr"
        Region              complement(3601..3632)
                            /label=nutR
        Misc._feature       complement(3615..3632)
                            /note="rho utilization site A (rutA)"
        Variation           complement(3636..3715)
                            /note="imm434 region"
        CDS                 complement(3640..3715)
                            /codon_start=1
                            /transl_table=11
                            /product="cro (antirepressor; also tof;66)"
                            /protein_id="AAA96582.1"
                            /db_xref="GI:215148"
/translation="MEQRITLKDYAMRFGQTKTAKDLGVYQSAINKAIHAGRKIFLTIN
                            ADGSVYAEEVKPFPSNKKTTA"
        Region              complement(3729..3730)
                            /label="1/2 HaeIII site that Rosenberg used"
        CDS                 complement(3731..3907)
                            /codon_start=1
                            /transl_table=11
                            /product="N (early gene regulator;133)"
                            /protein_id="AAA96578.1"
                            /db_xref="GI:508997"
/translation="MCQSRGVFVQDYNCHTPPKLTDRRIQMDAQTRRRERRAEKQAQWK
AANPLLVGVSAKPVNRPILSLNRKPKSRVESALNPIDLTVLAEYHKQIESNLQRIERKNQRTWYSKPGERGITCS
GRQKIKGKSIPLI"
        Source              complement(3731..4023)
                            /note="originates from LAMCG rev"
                            /label="lambda DNA"
        Region              complement(3731..3733)
                            /label="1/2 HpaI site that Rosenberg used"
        Variation           3731..4184
                            /note="imm21 region"
        Misc._binding       complement(3987..4003)
                            /note="N-utilization leftward.; putative"
                            /bound_moiety="Nutl"
        Region              complement(3988..4018)
                            /label=nutL
        Source              complement(4024..4184)
                            /note="originates from LAMCG rev"
                            /label="lambda DNA"
        Primer              4024..4044
                            /note=cagtcagtcagaaTTCATGGTGGTCAGTGCGTCC
                            /label=PLvect3
        Region              complement(4024..4369)
                            /note="originates from EC1 pL region"
                            /label="EC1 pL region"
        mRNA                complement(4051)
                            /note="mRNA-pl (alt.; via tl2a terminator)"
                            /label="pL1 mRNA start"
        Variation           4052..4184
                            /note="imm434 region"
        Promoter            complement(4058..4063)
                            /label="pL1 -10"
        operator            complement(4060..4076)
                            /note="operator-l1 (first base on comp strand)"
                            /label=OL1
        Primer              complement(4075..4092)
                            /label=pLseq
        Promoter            complement(4081..4086)
                            /label="pL1 -35"
        operator            complement(4084..4100)
                            /note="operator-l2 (first base on comp strand)"
                            /label=OL2
        mRNA                complement(4093)
                            /label="pL2 mRNA start"
        Promoter            complement(4100..4105)
                            /label="pL2 -10"
        operator            complement(4104..4120)
                            /note="operator-l3 (first base on comp strand)"
                            /label=OL3
```

-continued

| Promoter | complement(4122..4127) |
| | /label="pL2 -35" |
| Source | complement(4185..6244) |
| | /label="pUC18 DNA" |
| Primer | complement(4350..4369) |
| | /note=cagtcagtcaACATGTTCTTTCCTGCGTTA |
| | /label=pLnut-F |
| Primer | complement(4414..4430) |
| | /label=pLnutseq-F |
| Replication_ori | complement(4425..5013) |
| | /label="Replication origin" |
| RNA_transcript | complement(4425..4977) |
| | /label=RNAII |
| Promoter | 4832..4836 |
| | /label="RNAI -35" |
| Promoter | 4853..4858 |
| | /label="RNAI -10" |
| RNA_transcript | 4867..4974 |
| | /label=RNAI |
| Promoter | complement(4988..4992) |
| | /label="RNAII -10" |
| Promoter | complement(5008..5013) |
| | /label="RNAII -35" |
| CDS | complement(5184..6044) |
| | /label=beta-lactamase |
| Restriction_sit | 5916..5927 |
| | /label="EcoK site" |
| Signal_peptide | complement(5976..6044) |
| | /label=beta-lactamase |
| Promoter | complement(6088..6093) |
| | /label="beta-lactamase -10" |
| Promoter | complement(6109..6114) |
| | /label="beta-lactamase -35" |

```
ORIGIN
     1 TCGCGCGTTT CGGTGATGAC GGTGAAAACC TCTGACACAT GCAGCTCCCG GAGACGGTCA
    61 CAGCTTGTCT GTAAGCGGAT GCCGGGAGCA GACAAGCCCG TCAGGGCGCG TCAGCGGGTG
   121 TTGGCGGGTG TCGGGGCTGG CTTAACTATG CGGCATCAGA GCAGATTGTA CTGAGAGTGC
   181 ACCATATATG CGGTGTGAAA TACCGCACAG ATGCGTAAGG AGAAAATACC GCATCAGGCG
   241 CCTCCTCAAC CTGTATATTC GTAAACCACG CCCAATGGGA GCTGTCTCAG GTTTGTTCCT
   301 GATTGGTTAC GGCGCGTTTC GCATCATTGT TGAGTTTTTC CGCCAGCCCG ACGCGCAGTT
   361 TACCGGTGCC TGGGTGCAGT ACATCAGCAT GGGGCAAATT CTTTCCATCC CGATGATTGT
   421 CGCGGGTGTG ATCATGATGG TCTGGGCATA TCGTCGCAGC CCACAGCAAC ACGTTTCCTG
   481 AGGAACCATG AAACAGTATT TAGAACTGAT GCAAAAGTG CTCGACGAAG GCACACAGAA
   541 AAACGACCGT ACCGGAACCG GAACGCTTTC CATTTTTGGT CATCAGATGC GTTTTAACCT
   601 GCAAGATGGA TTCCCGCTGG TGACAACTAA ACGTTGCCAC CTGCGTTCCA TCATCCATGA
   661 ACTGCTGTGG TTTCTGCAGG GCGACACTAA CATTGCTTAT CTACACGAAA ACAATGTCAC
   721 CATCTGGGAC GAATGGGCCG ATGAAAACGG CGACCTCGGG CCAGTGTATG GTAAACAGTG
   781 GCGCGCCTGG CCAACGCCAG ATGGTCGTCA TATTGACCAG ATCACTACGG TACTGAACCA
   841 GCTGAAAAAC GACCCGGATT CGCGCCGCAT TATTGTTTCA GCGTGGAACG TAGGCGAACT
   901 GGATAAAATG GCGCTGGCAC CGTGCCATGC ATTCTTCCAG TTCTATGTGG CAGACGGCAA
   961 ACTCTCTTGC CAGCTTTATC AGCGCTCCTG TGACGTCTTC CTCGGCCTGC CGTTCAACAT
  1021 TGCCAGCTAC GCGTTATTGG TGCATATGAT GGCGCAGCAG TGCGATCTGG AAGTGGGTGA
  1081 TTTTGTCTGG ACCGGTGGCG ACACGCATCT GTACAGCAAC CATATGGATC AAACTCATCT
  1141 GCAATTAAGC CGCGAACGC GTCCGCTGCC GAAGTTGATT ATCAAACGTA AACCCGAATC
  1201 CATCTTCGAC TACCGTTTCG AAGACTTTGA GATTGAAGGC TACGATCCGC ATCGGGCAT
  1261 TAAAGCGCCG GTGGCTATCT AATTACGAAA CATCCTGCCA GAGCCGACGC CAGTGTGCGT
  1321 CGGTTTTTTT ACCCTCCGTT AAATTCTTCG AGACGCCTTC CCGAAGGCGC CATTCGCCAT
  1381 TCAGGCTGCG CAACTGTTGG GAAGGGCGAT CGGTGCGGGC CTCTTCGCTA TTACGCCAGC
  1441 TGGCGAAAGG GGGATGTGCT GCAAGGCGAT TAAGTTGGGT AACGCCAGGG TTTTCCCAGT
  1501 CACGACGTTG TAAAACGACG GCCAGTGCCA AGCTTTCTTT AATGAAGCAG GGCATCAGGA
  1561 CGGTATCTTT GTGGAGAAAG CAGAGTAATC TTATTCAGCC TGACTGGTGG GAAACCACCA
  1621 GTCAGAATGT GTTAGCGCAT GTTGACAAAA ATACCATTAG TCACATTATC CGTCAGTCGG
  1681 ACGACATGGT AGATAACCTG TTTATTATGC GTTTTGATCT TACGTTTAAT ATTACCTTTA
  1741 TGCATGAAA CGGTCTTGGC TTTGATATTC ATTTGGTCAG AGATTTGAAT GGTTCCCTGA
  1801 CCTGCCATCC ACATTCGCAA CATACTCGAT TCGGTTCGGC TCAATGATAA CGTCGGCATA
  1861 TTTAAAAACG AGGTTATCGT TGTCTCTTTT TTCAGAATAT CGCCAAGGAT ATCGTCGAGA
  1921 GATTCCGGTT TAATCGATTT AGAACTGATC AATAAATTTT TTCTGACCAA TAGATATTCA
  1981 TCAAAATGAA CATTGGCAAT TGCCATAAAA ACGATAAATA ACGTATTGGG ATGTTGATTA
  2041 ATGATGAGCT TGATACGCTG ACTGTTAGAA GCATCGTGGA TGAAACAGTC TCATTAATA
  2101 AACACCACTG AAGGGCGCTG TGAATCACAA GCTATGCAA GGTCATCAAC GGTTTCAATG
  2161 TCGTTGATTT CTCTTTTTTT AACCCCTCTA CTCAACAGAT ACCCGGTTAA ACCTAGTCGG
  2221 GTGTAACTAC ATAAATCCAT AATAATCGTT GACATGGCAT ACCCTCACTC AATGCGTAAC
  2281 GATAATTCCC CTTACCTGAA TATTTCATCA TGACTAAACG GAACAACATG GGTCACCTTA
  2341 TGCGCCACTC TCGCGATTTT TCAGGCGGAC TTACTATCCC GTAAAGTGTT GTATAATTTG
  2401 CCTGGAATTG TCTTAAAGTA AAGTAAATGT TGCGTATATGT GAGTGAGCTT AAAACAAATA
  2461 TTTCGCTGCA GGAGTATCCT GGAAGATGTT CGTAGaagct tACTGCTCAC AAGAAAAAAG
  2521 GCACGTCATC TGACGTGCCT TTTTTATTTG TACTACCCTG TACGATTACT GCAGCTCGAG
  2581 TTTAattcaa atcttcttca gaaatcaatt tttgttcAGC GTTATACTTT TGGGATTTTA
```

-continued

```
2641  CCTCAAAATG GGATTCTATT TTCACCCACT CCTTACAAAG GATATTCTCA TGCCCAAAAA
2701  GCCAGTGTTT GGGGCCAATA ATGATTTTTT CTGGATTTTC TATCAAATAG GCCGCCCACC
2761  AGCTATAAGT GCTATTAGCG ATAATGCCAT GCTGACAAGA TTGCATGAGC AGCATGTCCC
2821  AATACGCCTC TTCTTCTTTA TCCCTAGTGG TCATGTCCAT AAAAGGGTAG CCAAGATCAA
2881  GATTTTGCGT GAATTCTAAG TCTTCGCAAA ACACAAAAAG TTCCATGTTT GGCACGCGCT
2941  TTGCCATATA CTCAAGCGCC TTTTTTTGAT AGTCAATACC AAGCTGACAG CCAATCCCCA
3001  CATAATCCCC TCTTCTTATA TGCACAAACA CGCTGTTTTT AGCGGCTAAA ATCAAAGAAA
3061  GCTTGCACTG ATATTCTTCC TCTTTTTTAT TATTATTCTT ATTATTTTCG GGtGGtGGtG
3121  GTAGAGTGAA GGTTTGCTTG ATTAAAGGGG ATATAGCATC AAAGTATCGT GGATCTTGGA
3181  AATAGCCAAA AAAATAAGTC AAGCGGCTTG GCTTTAGCAA TTTAGGCTCG TATTCAAAAA
3241  CGATTTCTTG ACTCACCCTA TCAAATCCCA TGCATTTGAG CGCGTCTCTT ACTAGCTTGG
3301  GGAGGTGTTG CATTTTAGCT ATAGCGATTT CTTTCGCGCT CGCATAGGGC AAATCAATAG
3361  GGAAAAGTTC TAATTGCATT TTCCTATCGC TCCAATCAAA AGAAGTGATA TCTAACAGCA
3421  CAGGCGTATT AGAGTGTTTT TGCAAACTTT TAGCGAAAGC GTATTGAAAC ATTTGATTCC
3481  CAAGCCCTCC GCAAATTTGC ACCACCTTAA AAGCCATATG tatatctcct tcttgaaTTC
3541  TAAaAATTGA TTGAATGTAT GCAAATAAAT GCATACACCA TAGGTGTGGT TTAATTTGAT
3601  GCCCTTTTTC AGGGCTGGAA TGTGTAAGAG CGGGGTTATT TATGCTGTTG TTTTTTTGTT
3661  ACTCGGGAAG GGCTTTACCT CTTCCGCATA AACGCTTCCA TCAGCGTTTA TAGTTAAAAA
3721  AATCTTTCGG AACTGGTTTT GCGCTTACCC CAACCAACAG GGGATTTGCT GCTTTCCATT
3781  GAGCCTGTTT CTCTGCGCGA CGTTCGCGGC GGCGTGTTTG TGCATCCATC TGGATTCTCC
3841  TGTCAGTTAG CTTTGGTGGT GTGTGGCAGT TGTAGTCCTG AACGAAAACC CCCCGCGATT
3901  GGCACATTGG CAGCTAATCC GGAATCGCAC TTACGGCCAA TGCTTCGTTT CGTATCACAC
3961  ACCCCAAAGC CTTCTGCTTT GAATGCTGCC CTTCTTCAGG GCTTAATTTT TAAGAGCGTC
4021  ACCTTCATGG TGGTCAGTGC GTCCTGCTGA TGTGCTCAGT ATCACCGCCA GTGGTATTTA
4081  TGTCAACACC GCCAGAGATA ATTTATCACC GCAGATGGTT ATCTGTATGT TTTTTATATG
4141  AATTTATTTT TTGCAGGGGG GCATTGTTTG GTAGGTGAGA GATCAATTCT GCATTAATGA
4201  ATCGGCCAAC GCGCGGGGAG AGGCGGTTTG CGTATTGGGC GCTCTTCCGC TTCCTCGCTC
4261  ACTGACTCGC TGCGCTCGGT CGTTCGGCTG CGGCGAGCGG TATCAGCTCA CTCAAAGGCG
4321  GTAATACGGT TATCCACAGA ATCAGGGGAT AACGCAGGAA AGAACATGTG AGCAAAAGGC
4381  CAGCAAAAGG CCAGGAACCG TAAAAAGGCC GCGTTGCTGG CGTTTTTCCA TAGGCTCCGC
4441  CCCCCTGACG AGCATCACAA AAATCGACGC TCAAGTCAGA GGTGGCGAAA CCCGACAGGA
4501  CTATAAAGAT ACCAGGCGTT TCCCCCTGGA AGCTCCCTCG TGCGCTCTCC TGTTCCGACC
4561  CTGCCGCTTA CCGGATACCT GTCCGCCTTT CTCCCTTCGG GAAGCGTGGC GCTTTCTCAT
4621  AGCTCACGCT GTAGGTATCT CAGTTCGGTG TAGGTCGTTC GCTCCAAGCT GGGCTGTGTG
4681  CACGAACCCC CCGTTCAGCC CGACCGCTGC GCCTTATCCG GTAACTATCG TCTTGAGTCC
4741  AACCCGGTAA GACACGACTT ATCGCCACTG GCAGCAGCCA CTGGTAACAG GATTAGCAGA
4801  GCGAGGTATG TAGGCGGTGC TACAGAGTTC TTGAAGTGGT GGCCTAACTA CGGCTACACT
4861  AGAAGGACAG TATTTGGTAT CTGCGCTCTG CTGAAGCCAG TTACCTTCGG AAAAAGAGTT
4921  GGTAGCTCTT GATCCGGCAA ACAAACCACC GCTGGTAGCG GTGGTTTTTT TGTTTGCAAG
4981  CAGCAGATTA CGCGCAGAAA AAAAGGATCT CAAGAAGATC CTTTGATCTT TTCTACGGGG
5041  TCTGACGCTC AGTGGAACGA AAACTCACGT TAAGGGATTT TGGTCATGAG ATTATCAAAA
5101  AGGATCTTCA CCTAGATCCT TTTAAATTAA AAATGAAGTT TTAAATCAAT CTAAAGTATA
5161  TATGAGTAAA CTTGGTCTGA CAGTTACCAA TGCTTAATCA GTGAGGCACC TATCTCAGCG
5221  ATCTGTCTAT TTCGTTCATC CATAGTTGCC TGACTCCCCG TCGTGTAGAT AACTACGATA
5281  CGGGAGGGCT TACCATCTGG CCCCAGTGCT GCAATGATAC CGCGAGACCC ACGCTCACCG
5341  GCTCCAGATT TATCAGCAAT AAACCAGCCA GCCGGAAGGG CCGAGCGCAG AAGTGGTCCT
5401  GCAACTTTAT CCGCCTCCAT CCAGTCTATT AATTGTTGCC GGGAAGCTAG AGTAAGTAGT
5461  TCGCCAGTTA ATAGTTTGCG CAACGTTGTT GCCATTGCTA CAGGCATCGT GGTGTCACGC
5521  TCGTCGTTTG GTATGGCTTC ATTCAGCTCC GGTTCCCAAC GATCAAGGCG AGTTACATGA
5581  TCCCCCATGT TGTGCAAAAA AGCGGTTAGC TCCTTCGGTC CTCCGATCGT TGTCAGAAGT
5641  AAGTTGGCCG CAGTGTTATC ACTCATGGTT ATGGCAGCAC TGCATAATTC TCTTACTGTC
5701  ATGCCATCCG TAAGATGCTT TTCTGTGACT GGTGAGTACT CAACCAAGTC ATTCTGAGAA
5761  TAGTGTATGC GGCGACCGAG TTGCTCTTGC CCGGCGTCAA TACGGGATAA TACCGCGCCA
5821  CATAGCAGAA CTTTAAAAGT GCTCATCATT GGAAAACGTT CTTCGGGGCG AAAACTCTCA
5881  AGGATCTTAC CGCTGTTGAG ATCCAGTTCG ATGTAACCCA CTCGTGCACC CAACTGATCT
5941  TCAGCATCTT TTACTTTCAC CAGCGTTTCT GGGTGAGCAA AACAGGAAG GCAAAATGCC
6001  GCAAAAAAGG GAATAAGGGC GACACGGAAA TGTTGAATAC TCATACTCTT CCTTTTTCAA
6061  TATTATTGAA GCATTTATCA GGGTTATTGT CTCATGAGCG GATACATATT TGAATGTATT
6121  TAGAAAAATA AACAAATAGG GGTTCCGCGC ACATTTCCCC GAAAAGTGCC ACCTGACGTC
6181  TAAGAAACCA TTATTATCAT GACATTAACC TATAAAAATA GGCGTATCAC GAGGCCCTTT
6241  CGTC (SEQ ID NO: 1; plasmid G171)
```

The nucleic acid construct further comprises an α(1,2) fucosyltransferase gene comprising, e.g., at least 10% and less than 40% identity at the amino acid level to *Helicobacter pylori* 26695 alpha-(1,2)fucosyltransferase (futC). For example, the exogenous α(1,2)fucosyltransferase gene is selected from the group consisting of *Helicobacter pylori* 26695 alpha-(1,2)fucosyltransferase (futC), *Vibrio cholera* O22 wblA, *Escherichia coli* O126 wbgL, *Helicobacter bilis* ATCC 437879 futD, *Helicobacter cinaedi* CCUG 18818 alpha-1,2-fucosyltransferase (futE), *Helicobacter mustelae* 12198 (ATCC 43772) alpha-(1,2)-fucosyltransferase (futL), *Bacteroides vulgatus* ATCC 8482 glycosyl transferase family protein (futN), *Bacteroides ovatus* ATCC 8483 futO, *Escherichia coli* O55:H7 (str. CB9615) fucosyltransferase (wbgN), *Bacteroides fragilis* (NCTC) 9343 alpha-1,2-fucosyltransferase (bft1), and *Bacteroides fragilis* (NCTC) 9343 fucosyl transferase (bft3/wcfB). The depiction of pG171 bears the alpha 1,2 FT gene futC to serve as an example.

Also within the invention is an isolated *E. coli* bacterium as described above and characterized as comprising a reduced level of β-galactosidase activity, a defective colonic acid synthesis pathway, a mutation in the lacA gene, a mutation in an ATP-dependant intracellular protease, and a mutation in a thyA gene. The invention also provides methods of identifying an α(1,2)fucosyltransferase gene capable of synthesizing 2'-fucosyllactose (2'-FL) in *E. coli*. The method of identifying non-FutC lactose-utilizing, α(1,2)fucosyltransferase enzyme comprises the following steps:

1) performing a computational search of sequence databases to define a broad group of simple sequence homologs of any known, lactose-utilizing α(1,2)fucosyltransferase;

2) using the list from step (1), deriving a search profile containing common sequence and/or structural motifs shared by the members of the list;

3) searching sequence databases, using a derived search profile based on the common sequence or structural motif from step (2) as query, and identifying a candidate sequences, wherein a sequence homology to a reference lactose-utilizing α(1,2)fucosyltransferase is 40% or less;

4) compiling a list of candidate organisms, said organisms being characterized as expressing α(1,2)fucosyl-glycans in a naturally-occurring state;

5) selecting candidate sequences that are derived from candidate organisms to generate a list of candidate lactose-utilizing enzymes;

6) expressing the candidate lactose-utilizing enzyme in a host organism; and 7) testing for lactose-utilizing α(1,2)fucosyltransferase activity, wherein detection of 2'-FL in said organism indicates that the candidate sequence comprises a non-FutC lactose-utilizing α(1,2)fucosyltransferase. For example, the sequence homology to a reference lactose-utilizing α(1,2) fucosyltransferase is 40% or less.

A purified fucosylated oligosaccharide produced by the methods described above is also within the invention. The purified oligosaccharide (2'-FL) obtained at the end of the process is a white/slightly off-white, crystalline, sweet powder. Unlike oligosaccharide production methods using FutC, the methods utilizing certain non-FutC enzymes (e.g. FutL) do not possess α(1,3)fucosyltransferase activity which leads to side reactions. The lack of a (1,3)fucosyltransferase activity associated with FutL contributes to its efficiency in producing 2'FL and is an advantage compared to FutC. FutL does not possess alpha 1,3 fucosyltransferase activity. For example, an engineered E. coli cell, E. coli culture supernatant, or E. coli cell lysate according to the invention comprises recombinant 2'-FL and does not substantially comprise α1,3 fucosylated lactose prior to purification of 2'-FL from the cell, culture supernatant, or lysate. Both FutN and WbgL appear to have alpha 1,3 fucosyltransferase activity (similar to FutC). However as a general matter, the fucosylated oligosaccharide produced by the methods contains a negligible amount of 3-FL in a 2'-FL-containing cell, cell lysate or culture, or supernatant, e.g., less than 1% of the level of 2'-FL or 0.5% of the level of 2'-FL.

A purified oligosaccharide, e.g., 2'-FL or LDFT, is one that is at least 90%, 95%, 98%, 99%, or 100% (w/w) of the desired oligosaccharide by weight. Purity is assessed by any known method, e.g., thin layer chromatography or other chromatographic techniques known in the art. The invention includes a method of purifying a fucosylated oligosaccharide produced by the genetically engineered bacterium described above, which method comprises separating the desired fucosylated oligosaccharide (e.g., 2'-FL) from contaminants in a bacterial cell lysate or bacterial cell culture supernatant of the bacterium.

The oligosaccharides are purified and used in a number of products for consumption by humans as well as animals, such as companion animals (dogs, cats) as well as livestock (bovine, equine, ovine, caprine, or porcine animals, as well as poultry). For example, a pharmaceutical composition comprises purified 2'-FL and a pharmaceutically-acceptable excipient that is suitable for oral administration. Large quantities of 2'-FL are produced in bacterial hosts, e.g., an E. coli bacterium comprising an exogenous α(1,2)fucosyltransferase gene.

An E. coli bacterium comprising an enhanced cytoplasmic pool of lactose and GDP-fucose is useful in such production systems. Endogenous E. coli metabolic pathways and genes are manipulated in ways that result in the generation of increased cytoplasmic concentrations of lactose and/or GDP-fucose, as compared to levels found in wild type E. coli. For example, the bacteria contain at least 10%, 20%, 50%, or 2×, 5×, 10× or more of the levels compared to a corresponding wild type bacteria that lacks the genetic modifications described above.

A method of producing a pharmaceutical composition comprising a purified human milk oligosaccharide (HMOS) is carried out by culturing the bacterium described above, purifying the HMOS produced by the bacterium, and combining the HMOS with an excipient or carrier to yield a dietary supplement for oral administration. These compositions are useful in methods of preventing or treating enteric and/or respiratory diseases in infants and adults. Accordingly, the compositions are administered to a subject suffering from or at risk of developing such a disease.

The invention also provides methods for increasing the intracellular concentration of lactose in E. coli, for cells grown in the presence of lactose, by using manipulations of endogenous E. coli genes involved in lactose import, export, and catabolism. In particular, described herein are methods of increasing intracellular lactose levels in E. coli genetically engineered to produce a human milk oligosaccharide by simultaneous deletion of the endogenous β-galactosidase gene (lacZ) and the lactose operon repressor gene (lacI During construction of this deletion, the lacIq promoter is placed immediately upstream of (contiguous with) the lactose permease gene, lacY, i.e., the sequence of the lacIq promoter is directly upstream and adjacent to the start of the sequence encoding the lacY gene, such that the lacY gene is under transcriptional regulation by the lacIq promoter. The modified strain maintains its ability to transport lactose from the culture medium (via LacY), but is deleted for the wild-type chromosomal copy of the lacZ (encoding β-galactosidase) gene responsible for lactose catabolism. Thus, an intracellular lactose pool is created when the modified strain is cultured in the presence of exogenous lactose. Another method for increasing the intracellular concentration of lactose in E. coli involves deletion of the lacA gene. The lacA mutation prevents the formation of intracellular acetyl-lactose, which not only removes this molecule as a contaminant from subsequent purifications, but also eliminates E. coli's ability to export excess lactose from its cytoplasm (Danchin A. Cells need safety valves. Bioessays 2009, July; 31(7):769-73.), thus greatly facilitating purposeful manipulations of the E. coli intracellular lactose pool.

The invention also provides methods for increasing intracellular levels of GDP-fucose in Escherichia coli by manipulating the organism's endogenous colanic acid biosynthesis pathway. This increase is achieved through a number of genetic modifications of endogenous E. coli genes involved either directly in colanic acid precursor biosynthesis, or in overall control of the colanic acid synthetic regulon. In particular, described herein are methods of increasing intracellular GDP-fucose levels in E. coli genetically engineered to produce a human milk oligosaccharide by deletion of the weal gene, encoding the UDP-glucose lipid carrier transferase. In a wcaJ null background, GDP-fucose accumulates in the E. coli cytoplasm.

In one aspect, the human milk oligosaccharide produced by engineered bacteria comprising an exogenous nucleic acid molecule encoding an α(1,2)fucosyltransferase is 2'-FL (2'-fucosyllactose). Preferably the α(1,2)fucosyltransferase utilized is any α(1,2)fucosyltransferase capable of using lactose as the sugar acceptor substrate for 2'-FL synthesis. Preferably, the exogenous α(1,2)fucosyltransferase gene comprises at least 10% identity at the amino acid level and less than about 40% to *Helicobacter pylori* 26695 alpha-(1,2)fucosyltransferase (FutC).

The invention also provides compositions comprising *E. coli* genetically engineered to produce the human milk tetrasaccharide lactodifucotetraose (LDFT). The *E. coli* in this instance comprise an exogenous nucleic acid molecule encoding an α(1,2)fucosyltransferase that also possesses α(1,3)fucosyltransferase activity.

The invention provides a method of treating, preventing, or reducing the risk of infection in a subject comprising administering to said subject a composition comprising a purified recombinant human milk oligosaccharide, wherein the HMOS binds to a pathogen and wherein the subject is infected with or at risk of infection with the pathogen. In one aspect, the infection is caused by a Norwalk-like virus or *Campylobacter jejuni*. The subject is preferably a mammal in need of such treatment. The mammal is, e.g., any mammal, e.g., a human, a primate, a mouse, a rat, a dog, a cat, a cow, a horse, or a pig. In a preferred embodiment, the mammal is a human. For example, the compositions are formulated into animal feed (e.g., pellets, kibble, mash) or animal food supplements for companion animals, e.g., dogs or cats, as well as livestock or animals grown for food consumption, e.g., cattle, sheep, pigs, chickens, and goats. Preferably, the purified HMOS is formulated into a powder (e.g., infant formula powder or adult nutritional supplement powder, each of which is mixed with a liquid such as water or juice prior to consumption) or in the form of tablets, capsules or pastes or is incorporated as a component in dairy products such as milk, cream, cheese, yogurt or kefir, or as a component in any beverage, or combined in a preparation containing live microbial cultures intended to serve as probiotics, or in prebiotic preparations to enhance the growth of beneficial microorganisms either in vitro or in vivo.

Polynucleotides, polypeptides, and oligosaccharides of the invention are purified and/or isolated. Purified defines a degree of sterility that is safe for administration to a human subject, e.g., lacking infectious or toxic agents. Specifically, as used herein, an "isolated" or "purified" nucleic acid molecule, polynucleotide, polypeptide, protein or oligosaccharide, is substantially free of other cellular material, or culture medium when produced by recombinant techniques, or chemical precursors or other chemicals when chemically synthesized. For example, purified HMOS compositions are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, thin layer chromatography, or high-performance liquid chromatography (HPLC) analysis. For example, a "purified protein" refers to a protein that has been separated from other proteins, lipids, and nucleic acids with which it is naturally associated. Preferably, the protein constitutes at least 10, 20, 50, 70, 80, 90, 95, 99-100% by dry weight of the purified preparation.

Similarly, by "substantially pure" is meant an oligosaccharide that has been separated from the components that naturally accompany it. Typically, the oligosaccharide is substantially pure when it is at least 60%, 70%, 80%, 90%, 95%, or even 99%, by weight, free from the proteins and naturally-occurring organic molecules with which it is naturally associated.

By "isolated nucleic acid" is meant a nucleic acid that is free of the genes which, in the naturally-occurring genome of the organism from which the DNA of the invention is derived, flank the gene. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones.

A "heterologous promoter" is a promoter which is different from the promoter to which a gene or nucleic acid sequence is operably linked in nature.

The term "overexpress" or "overexpression" refers to a situation in which more factor is expressed by a genetically-altered cell than would be, under the same conditions, by a wild type cell. Similarly, if an unaltered cell does not express a factor that it is genetically altered to produce, the term "express" (as distinguished from "overexpress") is used indicating the wild type cell did not express the factor at all prior to genetic manipulation.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a nontoxic but sufficient amount of the formulation or component to provide the desired effect.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The host organism used to express the non-FutC lactose-accepting fucosyltransferase gene product is typically the enterobacterium *Escherichia coli* K12 (*E. coli*). *E. coli* K-12 is not considered a human or animal pathogen nor is it toxicogenic. *E. coli* K-12 is a standard production strain of bacteria and is noted for its safety due to its poor ability to colonize the colon and establish infections (see, e.g., epa.gov/oppt/biotech/pubs/fra/fra004.htm). However, a variety of bacterial species may be used in the oligosaccharide biosynthesis methods, e.g., *Erwinia herbicola* (*Pantoea agglomerans*), *Citrobacter freundii*, *Pantoea citrea*, *Pectobacterium carotovorum*, or *Xanthomonas campestris*. Bacteria of the genus *Bacillus* may also be used, including *Bacillus subtilis*, *Bacillus licheniformis*, *Bacillus coagulans*, *Bacillus thermophilus*, *Bacillus laterosporus*, *Bacillus megaterium*, *Bacillus mycoides*, *Bacillus pumilus*, *Bacillus lentus*, *Bacillus cereus*, and *Bacillus circulans*. Similarly, bacteria of the genera *Lactobacillus* and *Lactococcus* may be modified using the methods of this invention, including but not limited to *Lactobacillus acidophilus*, *Lactobacillus salivarius*, *Lactobacillus plantarum*, *Lactobacillus helveticus*, *Lactobacillus delbrueckii*, *Lactobacillus rhamnosus*, *Lactobacillus bulgaricus*, *Lactobacillus crispatus*, *Lactobacillus gasseri*, *Lactobacillus casei*, *Lactobacillus reuteri*, *Lactobacillus jensenii*, and *Lactococcus lactis*. *Streptococcus thermophiles* and *Proprionibacterium freudenreichii* are also suitable bacterial species for the invention described herein. Also included as part of this invention are strains, modified as described here, from the genera *Enterococcus* (e.g., *Enterococcus faecium* and *Enterococcus thermophiles*), *Bifidobacterium* (e.g., *Bifidobacterium longum*, *Bifidobacterium infantis*, and *Bifidobacterium bifidum*), *Sporolactobacillus* spp., *Micromomospora* spp., *Micrococcus* spp., *Rhodococcus* spp., and *Pseudomonas* (e.g., *Pseudomonas fluorescens* and *Pseudomonas aeruginosa*). Bacteria comprising the characteristics described herein are cultured in the presence of lactose, and a fucosylated oligosaccharide is retrieved, either from the bacterium itself or from a culture supernatant of the bacterium. The fucosylated oligosaccharide is purified for use in therapeutic or nutritional products, or the bacteria are used directly in such products.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 3A shows significant production of 2'-FL by WbgL. FIG. 3B shows significant production of 2'-FL by FutL. FIG. 3C shows significant production of 2'-FL by FutN.

DETAILED DESCRIPTION OF THE INVENTION

Figure 1:
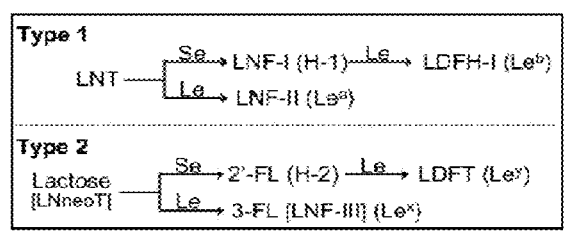
FIG. 1 is a schematic illustration showing the synthetic pathway of the fucosyl oligosaccharides of human milk. Se and Le indicate synthesis by fucosyltransferases of the secretor and Lewis genes, respectively. The abbreviated biochemical name [with alternate biochemical structure in brackets] is given (histo-blood group antigen analog in parentheses).

While some studies suggest that human milk glycans could be used as antimicrobial anti-adhesion agents, the difficulty and expense of producing adequate quantities of these agents of a quality suitable for human consumption has limited their full-scale testing and perceived utility. What has been needed is a suitable method for producing the appropriate glycans in sufficient quantities at reasonable cost. Prior to the invention described herein, there were attempts to use several distinct synthetic approaches for glycan synthesis. Some chemical approaches can synthesize oligosaccharides (Flowers, H. M. Methods Enzymol 50, 93-121 (1978); Seeberger, P. H. Chem Commun (Camb) 1115-1121 (2003)), but reactants for these methods are expensive and potentially toxic (Koeller, K. M. & Wong, C. H. Chem Rev 100, 4465-4494 (2000)). Enzymes expressed from engineered organisms (Albermann, C., Piepersberg, W. & Wehmeier, U. F. Carbohydr Res 334, 97-103 (2001); Bettler, E., Samain, E., Chazalet, V., Bosso, C., et al. Glycoconj J 16, 205-212 (1999); Johnson, K. F. Glycoconj J 16, 141-146 (1999); Palcic, M. M. Curr Opin Biotechnol 10, 616-624 (1999); Wymer, N. & Toone, E. J. Curr Opin Chem Biol 4, 110-119 (2000)) provide a precise and efficient synthesis (Palcic, M. M. Curr Opin Biotechnol 10, 616-624 (1999)); Crout, D. H. & Vic, G. Curr Opin Chem Biol 2, 98-111 (1998)), but the high cost of the reactants, especially the sugar nucleotides, limits their utility for low-cost, large-scale production. Microbes have been genetically engineered to express the glycosyltransferases needed to synthesize oligosaccharides from the bacteria's innate pool of nucleotide sugars (Endo, T., Koizumi, S., Tabata, K., Kakita, S. & Ozaki, A. Carbohydr Res 330, 439-443 (2001); Endo, T., Koizumi, S., Tabata, K. & Ozaki, A. Appl Microbiol Biotechnol 53, 257-261 (2000); Endo, T. & Koizumi, S. Curr Opin Struct Biol 10, 536-541 (2000); Endo, T., Koizumi, S., Tabata, K., Kakita, S. & Ozaki, A. Carbohydr Res 316, 179-183 (1999); Koizumi, S., Endo, T., Tabata, K. & Ozaki, A. Nat Biotechnol 16, 847-850 (1998)). However, prior to the invention described herein, there was a growing need to identify and characterize additional glycosyltransferases that are useful for the synthesis of HMOS in metabolically engineered bacterial hosts.

Not all α(1,2)fucosyltransferases can utilize lactose as an acceptor sugar. A desired enzyme utilizes GDP-fucose as a donor, and lactose is the acceptor for that donor. A method of identifying novel α(1,2)fucosyltransferase enzymes capable of utilizing lactose as an acceptor was carried out using the following steps:: 1) performing a computational search of sequence databases to define a broad group of simple sequence homologs of any known, lactose-utilizing α(1,2) fucosyltransferase; 2) using the list of homologs from step 1 to derive a search profile containing common sequence and/or structural motifs shared by the members of the broad group, e.g. by using computer programs such as MEME (Multiple Em for Motif Elicitation available at http://meme.sdsc.edu/meme/cgi-bin/meme.cgi) or PSI-BLAST (Position-Specific Iterated BLAST available at ncbi.nlm.nih.gov/blast with additional information at cnx.org/content/m11040/latest/); 3) searching sequence databases (e.g., using computer programs such as PSI-BLAST, or MAST (Motif Alignment Search Tool available at http://meme.sdsc.edu/meme/cgi-bin/mast.cgi); using this derived search profile as query, and identifying "candidate sequences" whose simple sequence homology to the original lactose-accepting α(1,2)fucosyltransferase is 40% or less; 4) scanning the scientific literature and developing a list of "candidate organisms" known to express α(1,2) fucosyl-glycans; 5) selecting only those "candidate sequences" that are derived from "candidate organisms" to generate a list of "candidate lactose-utilizing enzymes"; and 6) expressing each "candidate lactose-utilizing enzyme" and testing for lactose-utilizing α(1,2)fucosyltransferase activity.

The MEME suite of sequence analysis tools (meme.sdsc.edu/meme/cgi-bin/meme.cgi) can also be used as an alternative to PSI-BLAST. Sequence motifs are discovered using the program "MEME". These motifs can then be used to search sequence databases using the program "MAST". The BLAST and PHI-BLAST search algorithms are other well known alternatives.

To test for lactose-utilizing activity, the production of 2'-FL is evaluated in a host organism that expresses the candidate enzyme and which contains both cytoplasmic GDP-fucose and lactose pools. The production of 2'-FL indicates that the candidate enzyme-encoding sequence functions as a lactose-utilizing α(1,2)fucosyltransferase.

To find enzymes with similarity to FutC, entire amino acid of FutC was used as a query in PSI-BLAST. The results of the lactose-utilizing α(1,2)fucosyltransferase identification method of this invention are surprising, because the % identity of several of the lactose-utilizing α(1,2)fucosyltransferases identified are less than 40% of the reference FutC sequence. Another most surprising aspect of the study is that 8 of the 10 candidates tested were able to utilize lactose as an acceptor, 3 of which did so at levels very close to the "gold-standard" enzyme FutC. This was a higher "hit rate" was anticipated. While 6 out of 10 of the candidate enzymes are found in bacteria that incorporate α(1,2)fucose into their LPS structure, the oligosaccharides to which the fucose is attached are very different than the lactose each candidate enzyme is being asked to utilize in the query. Moreover, it was surprising that both WblA and WbgN could utilize lactose as an acceptor, because both of these enzymes are found in bacteria that do not incorporate fucose into their LPS structure. Rather, they utilize a related sugar called colitose.

Human Milk Glycans

Human milk contains a diverse and abundant set of neutral and acidic oligosaccharides (Kunz, C., Rudloff, S., Baier, W., Klein, N., and Strobel, S. (2000). Annu Rev Nutr 20, 699-722; Bode, L. (2006). J Nutr 136, 2127-130). More than 130 different complex oligosaccharides have been identified in human milk, and their structural diversity and abundance is unique to humans. Although these molecules may not be utilized directly by infants for nutrition, they nevertheless serve critical roles in the establishment of a healthy gut microbiome (Marcobal, A., Barboza, M., Froehlich, J. W., Block, D. E., et al. J Agric Food Chem 58, 5334-5340 (2010)), in the prevention of disease (Newburg, D. S., Ruiz-Palacios, G. M. & Morrow, A. L. Annu Rev Nutr 25, 37-58 (2005)), and in immune function (Newburg, D. S. & Walker, W. A. Pediatr Res 61, 2-8 (2007)). Despite millions of years of exposure to human milk oligosaccharides (HMOS), pathogens have yet to develop ways to circumvent the ability of HMOS to prevent adhesion to target cells and to inhibit infection. The ability to utilize HMOS as pathogen adherence inhibitors promises to address the current crisis of burgeoning antibiotic resistance. Human milk oligosaccharides produced by biosynthesis represent the lead compounds of a novel class of therapeutics against some of the most intractable scourges of society.

One alternative strategy for efficient, industrial-scale synthesis of HMOS is the metabolic engineering of bacteria. This approach involves the construction of microbial strains overexpressing heterologous glycosyltransferases, membrane transporters for the import of precursor sugars into the bacterial cytosol, and possessing enhanced pools of regenerating nucleotide sugars for use as biosynthetic precursors (Dumon, C., Samain, E., and Priem, B. (2004). Biotechnol Prog 20, 412-19; Ruffing, A., and Chen, R. R. (2006). Microb Cell Fact 5, 25). A key aspect of this approach is the heterologous glycosyltransferase selected for overexpression in the microbial host. The choice of glycosyltransferase can significantly affect the final yield of the desired synthesized oligosaccharide, given that enzymes can vary greatly in terms of kinetics, substrate specificity, affinity for donor and acceptor molecules, stability and solubility. A few glycosyltransferases derived from different bacterial species have been identified and characterized in terms of their ability to catalyze the biosynthesis of HMOS in E. coli host strains (Dumon, C., Bosso, C., Utille, J. P., Heyraud, A., and Samain, E. (2006). Chembiochem 7, 359-365; Dumon, C., Samain, E., and Priem, B. (2004). Biotechnol Prog 20, 412-19; Li, M., Liu, X. W., Shao, J., Shen, J., Jia, Q., Yi, W., Song, J. K., Woodward, R., Chow, C. S., and Wang, P. G. (2008). Biochemistry 47, 378-387). The identification of additional glycosyltransferases with faster kinetics, greater affinity for nucleotide sugar donors and/or acceptor molecules, or greater stability within the bacterial host significantly improves the yields of therapeutically useful HMOS. Prior to the invention described herein, chemical syntheses of HMOS were possible, but were limited by stereo-specificity issues, precursor availability, product impurities, and high overall cost (Flowers, H. M. Methods Enzymol 50, 93-121 (1978); Seeberger, P. H. Chem Commun (Camb) 1115-1121 (2003); Koeller, K. M. & Wong, C. H. Chem Rev 100, 4465-4494 (2000)). The invention overcomes the shortcomings of these previous attempts by providing new strategies to inexpensively manufacture large quantities of human milk oligosaccharides (HMOS) for use as dietary supplements. Advantages include efficient expression of the enzyme, improved stability and/or solubility of the gene product (2'-FL) and reduced toxicity to the host organism. For example, α(1,2)fucosyltransferases derived from E. coli strains (e.g. WbgL) are more stable and are expressed at higher levels within E. coli production hosts strains compared to FutC. In another example, highly active fucosyltransferase (futN) is derived from a commensal microbe (*Bacteroides*) rather than a pathogen. Since many engineered production strains use fucosyltransferase genes obtained from pathogens, safety and/or increased consumer acceptance are added advantages of this sequence/enzyme.

As described in detail below, E. coli (or other bacteria) is engineered to produce 2'-FL in commercially viable levels. For example, yields are >5 grams/liter in a bacterial fermentation process.

Role of Human Milk Glycans in Infectious Disease

Human milk glycans, which comprise both unbound oligosaccharides and their glycoconjugates, play a significant role in the protection and development of the infant gastrointestinal (GI) tract. Neutral fucosylated oligosaccharides, including 2'-fucosyllactose (2'-FL), protect infants against several important pathogens. Milk oligosaccharides found in various mammals differ greatly, and the composition in humans is unique (Hamosh M., 2001 Pediatr Clin North Am, 48:69-86; Newburg D. S., 2001 Adv Exp Med Biol, 501:3-10). Moreover, glycan levels in human milk change throughout lactation and also vary widely among individuals (Morrow A. L. et al., 2004 J Pediatr, 145:297-303; Chaturvedi P et al., 2001 Glycobiology, 11:365-372). Approximately 200 distinct human milk oligosaccharides have been identified and combinations of simple epitopes are responsible for this diversity (Newburg D. S., 1999 Curr_Med Chem, 6:117-127; Ninonuevo M. et al., 2006 J Agric Food Chem, 54:7471-74801).

Human milk oligosaccharides are composed of 5 monosaccharides: D-glucose (Glc), D-galactose (Gal), N-acetylglucosamine (GlcNAc), L-fucose (Fuc), and sialic acid (N-acetyl neuraminic acid, Neu5Ac, NANA). Human milk oligosaccharides are usually divided into two groups according to their chemical structures: neutral compounds containing Glc, Gal, GlcNAc, and Fuc, linked to a lactose (Galβ1-4Glc) core, and acidic compounds including the same sugars, and often the same core structures, plus NANA (Charlwood J. et al., 1999 Anal Biochem, 273:261-277; Martin-Sola et al., 2003 J Dairy Sci, 86:52-59; Parkkinen J. and Finne J., 1987 Methods Enzymol, 138:289-300; Shen Z. et al., 2001 J Chromatogr A, 921:315-321).

Approximately 70-80% of oligosaccharides in human milk are fucosylated, and their synthetic pathways are believed to proceed as shown in FIG. 1 (Type I and Type II pathways begin with different precursor molecules). A smaller proportion of the oligosaccharides are sialylated or both fucosylated and sialylated, but their synthetic pathways are not fully defined. Understanding of the acidic (sialylated) oligosaccharides is limited in part by the ability to measure these compounds. Sensitive and reproducible methods for the analysis of both neutral and acidic oligosaccharides have been designed. Human milk oligosaccharides as a class survive transit through the intestine of infants very efficiently, being essentially indigestible (Chaturvedi, P., Warren, C. D., Buescher, C. R., Pickering, L. K. & Newburg, D. S. Adv Exp Med Biol 501, 315-323 (2001)).

Human Milk Glycans Inhibit Binding of Enteropathogens to their Receptors

Human milk glycans have structural homology to cell receptors for enteropathogens and function as receptor decoys. For example, pathogenic strains of Campylobacter bind specifically to glycans containing H-2, i.e., 2'-fucosyl-N-acetyllactosamine or 2'-fucosyllactose (2'FL); Campylobacter binding and infectivity are inhibited by 2'-FL and other glycans containing this H-2 epitope. Similarly, some diarrheagenic E. coli pathogens are strongly inhibited in vivo by human milk oligosaccharides containing 2-linked fucose moieties. Several major strains of human caliciviruses, especially the noroviruses, also bind to 2-linked fucosylated glycans, and this binding is inhibited by human milk 2-linked fucosylated glycans. Consumption of human milk that has high levels of these 2-linked fucosyloligosaccharides was associated with lower risk of norovirus, Campylobacter, ST of E. coli-associated diarrhea, and moderate-to-severe diarrhea of all causes in a Mexican cohort of breastfeeding children (Newburg D. S. et al., 2004 Glycobiology, 14:253-263; Newburg D. S. et al., 1998 Lancet, 351:1160-1164). Several pathogens utilize sialylated glycans as their host receptors, such as influenza (Couceiro, J. N., Paulson, J. C. & Baum, L. G. Virus Res 29, 155-165 (1993)), parainfluenza (Amonsen, M., Smith, D. F., Cummings, R. D. & Air, G. M. J Virol 81, 8341-8345 (2007), and rotoviruses (Kuhlenschmidt, T. B., Hanafin, W. P., Gelberg, H. B. & Kuhlenschmidt, M. S. Adv Exp Med Biol 473, 309-317 (1999)). The sialyl-Lewis X epitope is used by Helicobacter pylori (Mandavi, J., Sonden, B., Hurtig, M., Olfat, F. O., et al. Science 297, 573-578 (2002)), Pseudomonas aeruginosa (Scharfman, A., Delmotte, P., Beau, J., Lamblin, G., et al. Glycoconj J 17, 735-740 (2000)), and some strains of noroviruses (Rydell, G. E., Nilsson, J., Rodriguez-Diaz, J., Ruvoen-Clouet, N., et al. Glycobiology 19, 309-320 (2009)).

Engineering of E. coli to Produce Human Milk Oligosaccharide 2'-FL

Described herein is a gene screening approach, which was used to identify new α(1,2)fucosyltransferases (α(1,2) FTs) for the synthesis of fucosyl-linked oligosaccharides in metabolically engineered E. coli. Of particular interest are α(1,2) FTs that are capable of the synthesis of the HMOS 2'-fucosyllactose (2'-FL). 2'-FL is the most abundant fucosylated oligosaccharide present in human milk, and this oligosaccharide provides protection to newborn infants against infectious diarrhea caused by bacterial pathogens such as Campylobacter jejuni (Ruiz-Palacios, G. M., et al. (2003). J Biol Chem 278, 14112-120; Morrow, A. L. et al. (2004). J Pediatr 145, 297-303; Newburg, D. S. et al. (2004). Glycobiology 14, 253-263).

The synthetic pathway of the fucosyl oligosaccharides of human milk is illustrated in FIG. 1. Structurally, 2'-FL consists of a fucose molecule α1,2 linked to the galactose portion of lactose (Fucα1-2Galβ1-4Glc). An α(1,2) FT from H. pylori strain 26695 termed FutC has been utilized to catalyze the synthesis of 2'-FL in metabolically engineered E. coli (Drouillard, S. et al. (2006). Angew Chem Int Ed Engl 45, 1778-780). Therefore, the amino acid sequence of FutC was used as a query in the search algorithm PSI-BLAST (Position Specific Iterated Basic Local Alignment Search Tool) to identify candidate novel α(1,2) FTs for the production of 2'-FL in E. coli. Using PSI-BLAST, a list of closely related protein sequences is created based on the query sequence. The algorithm then generates a profile sequence, which summarizes significant motifs present in these sequences. This profile is then used as a new query to identify a larger group of candidate sequences, and the process is iterated to generate an even larger group of candidates.

The FutC amino acid sequence was used as a query for 2 iterations of the PSI-BLAST search algorithm. This search yielded a group of 277 candidates with similarity to FutC, some of which were more closely related (shared amino acid identity greater than 25%) as well as a group that was more distantly related to FutC (shared amino acid identity less than 25%). Of the more closely related group, the predicted α(1,2) FTs from bacterial species that incorporate fucose into the O-antigen of their lipopolysaccharide (LPS) or into the polysaccharide subunits that compose the cell surface capsule were analyzed. α(1,2) FTs from these types of organisms are more likely to utilize fucose as a substrate, given the presence of fucose in their surface carbohydrate structures. α(1,2) FTs from known enteric bacterial species, either commensals or pathogens were also analyzed. Such organisms sometimes display carbohydrate structures on their cell-surface that contain fucose and mimic various 2'-fucosyl containing Lewis antigen structures found in higher organisms (Appelmelk, B. J. et al. (1998). Infect Immun 66, 70-76; Coyne, M. J. et al. (2005). Science 307, 1778-781). Candidate α(1,2) FTs from these types of organisms are more likely to utilize fucose as a substrate and also to catalyze the linkage of fucose to useful acceptor oligosaccharides.

Ten α(1,2) FTs with greater than 25% homology at the amino acid level to FutC identified from the screen were analyzed (Table 1).

TABLE 1

Summary of candidate α (1,2) fucosyltransferases tested for their ability to promote 2'-FL in engineered *E. coli* strains. The activity of each candidate was compared to FutC and described semi-quantitatively using the "+" symbol in the last column, where FutC is assessed the highest activity with 4 "+" symbols.

| Gene Name | Accession No. (NCBI) | Organism | % Identity w/FutC | Fucose in LPS or capsule? | 2'-FL Synthesis |
|---|---|---|---|---|---|
| futC | NP_206893 NP_206894 | *H. pylori* 26695 | — | Yes | ++++ |
| wblA | BAA33632 | *V. cholerae* O22 | 28% | No | + |
| wbgL | ADN43847 | *E. Coli* O126 | 25% | Yes | +++ |
| futD | ZP_04580654 | *H. bilis* ATCC 437879 | 39% | Yes | + |
| futE | ZP_07805473 | *H. cinaedi* CCUG 18818 | 44% | Unknown | − |
| futL | YP_003517185 | *H. mustelae* ATCC 43772 | 70% | Yes | +++ |
| futN | YP_001300461 | *B. vulgatus* ATCC 8482 | 27% | Unknown | ++ |
| futO | ZP_02065239 | *B. ovatus* ATCC 8483 | 27% | Unknown | − |
| wbgN | YP_003500093 | *E coli* O55:H7 | 28% | No | + |
| bft1 | CAH09369 | *B. fragilis* 9343 | 34% | Yes | − |
| bft3/wcfB | CAH06753 | *B. fragilis* 9343 | 28% | Yes | + |

The amino acid sequence of *Helicobacter pylori* 26695 alpha-(1,2)fucosyltransferase (FutC) is set forth below (SEQ ID NO: 2; GenBank Accession Number NP_206893 and NP_206894 (GI:15644723 and 15644724), incorporated herein by reference).

```
  1 mafkvvqicg glgnqmfqya fakslqkhln tpvllditsf dwsnrkmqle lfpidlpyas
 61 akeiaiakmq hlpklvrdtl kcmgfdrvsq eivfeyepgl lkpsrltyfy gyfqdpryfd
121 aisplikqtf tlpppengnn kkkeeeyhrk lalilaakns vfvhvrrgdy vgigcqlgid
181 yqkkaleyia krvpnmelfv fcedlkftqn ldlgypfmdm ttrdkeeeay wdmllmqsck
241 hgiianstys wwaaylinnp ekiiigpkhw lfghenilck ewvkieshfe vkskkyna
```

The amino acid sequence of *Vibrio cholera* O22 WblA is set forth below (SEQ ID NO: 3; GenBank Accession Number BAA33632 (GI:3721682), incorporated herein by reference).

```
  1 mivmkisggl gnqlfqyavg raiaiqygvp lkldvsaykn yklhngyrld qfninadian
 61 edeifhlkgs snrlsrilrr lgwlkkntyy aekgrtiydv svfmqapryl dgywgnegyf
121 sqiravllqe lwpnqplsin aqahqikiqq thavsihvrr gdylnhpeig vldidyykra
181 vdyikekiea pvffvfsndv awckdnfnfi dspvfiedtq teiddlmlmc qcqhnivans
241 sfswwaawln snvdkiviap ktwmaenpkg ykwvpdswre i
```

The amino acid sequence of *Escherichia coli* O126 WbgL is set forth below (SEQ ID NO: 4; GenBank Accession Number ADN43847 (GI:307340785), incorporated herein by reference).

```
  1 msiirlqggl gnqlfqfsfg yalskingtp lyfdishyae nddhggyrln nlqipeeylq
 61 yytpkinniy kflvrgsrly peiflflgfc nefhaygydf eyiaqkwksk kyigywqseh
121 ffhkhildlk effipknvse qanllaakil esqsslsihi rrgdyiknkt atlthgvcsl
```

```
181 eyykkalnki rdlamirdvf ifsddifwck enietllskk yniyysedls qeedlwlmsl 241 anhhiianss fswwgaylgt sasqiviypt pwyditpknt yipivnhwin vdkhssc
```

The amino acid sequence of *Helicobacter bilis* ATCC 437879 FutD is set forth below (SEQ ID NO: 5; GenBank Accession Number ZP_04580654 (GI: 237750174), incorporated herein by reference).

```
  1 mgdykivelt cglgnqmfqy afakalqkhl qvpvlldktw ydtqdnstqf sldifnvdle 61 yatntqieka karvsklpgl lrkmfglkkh niaysqsfdf hdeyllpndf tyfsgffqna 121 kylkgleqel ksifyydsnn fsnfgkqrle lilqaknsif ihirrgdyck igwelgmdyy 181 kraiqyimdr veepkffifg atdmsfteqf qknlglnenn sanlsektit qdnqhedmfl 241 mcyckhaila nssysfwsay lnndannivi aptpwlldnd niicddwiki ssk
```

The amino acid sequence of *Helicobacter cinaedi* CCUG 18818 alpha-1,2-fucosyltransferase (FutE) is set forth below (SEQ ID NO: 6; GenBank Accession Number ZP_07805473 (GI:313143280), incorporated herein by reference).

```
  1 mlfpfkfiyn rlrykairli rrrasyrpfy efyahivwge egvvndrimk hyressfkpy 61 afpyginmsf vysndvyall kddfrlkipl rydnamlkkq iqntdksvfl hirrgdylqs 121 eglyvvlgvt yyqkaleilk skitnphifv fsndmcwcke ylmryvdfsg ctidfiegnt 181 egnaveemel mrscqhaiia nstfswwaay lienpdkivi mpkeylndss rflpkqflal 241 knwflvdhiw gsvelan
```

The amino acid sequence of *Helicobacter mustelae* 12198 (ATCC 43772) alpha-1,2-fucosyltransferase (FutL) is set forth below (SEQ ID NO: 7; GenBank Accession Number YP_003517185 (GI:291277413), incorporated herein by reference).

```
  1 mdfkivqvhg glgnqmfqya fakslqthln ipvlldttwf dygnrelglh lfpidlqcas 61 aqqiaaahmq nlprlvrgal rrmglgrvsk eivfeympel fepsriayfh gyfqdpryfe 121 displikqtf tlphptehae qysrklsqil aaknsvfvhi rrgdymrlgw qldisyqlra 181 iaymakrvqn lelflfcedl efvqnldlgy pfvdmttrdg aahwdmmlmq sckhgiitns 241 tyswwaayli knpekiiigp shwiygneni lckdwvkies qfetks
```

Figure 3:
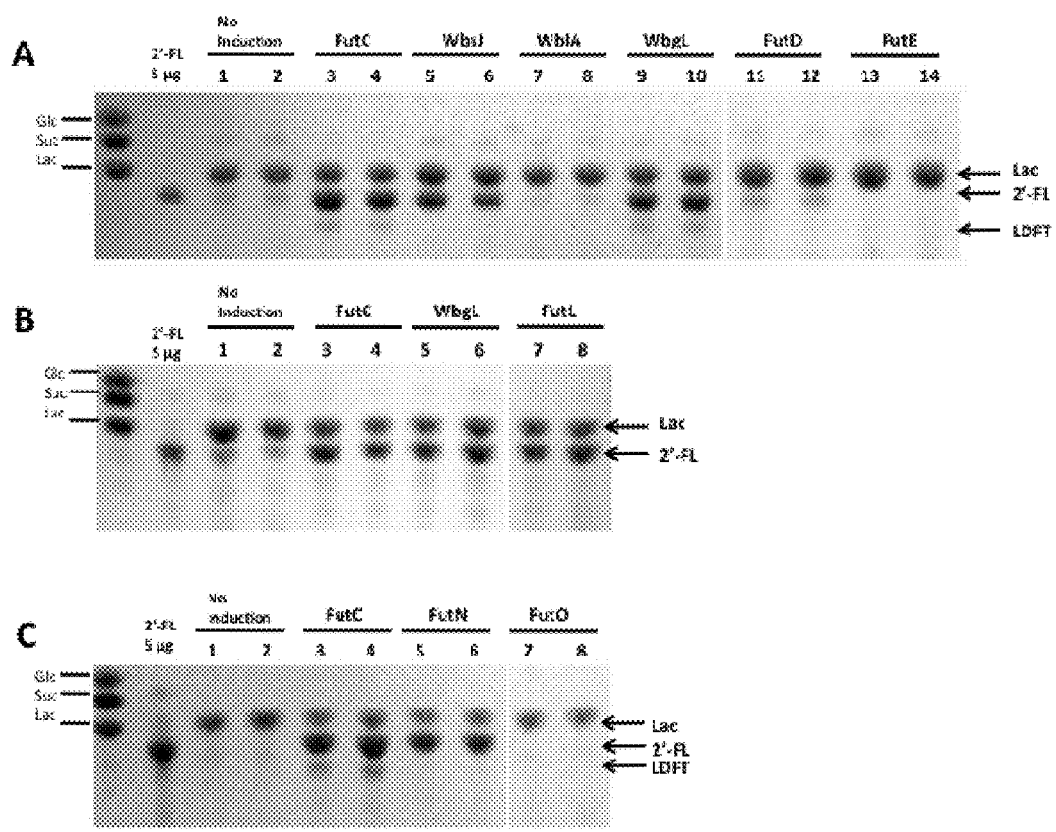
FIG. 3 is a series of photographs showing thin layer chromatography analysis of 2'-FL produced in *E. coli* strains by candidate α(1,2)fucosyltransferases.

One α(1,2)fucosyltransferase identified through the screen that possessed comparable enzymatic activity relative to FutC was termed FutL. FutL was found to direct the synthesis of 2'-FL at ~75% the level of FutC in the metabolically engineered *E. coli* production strain (Table 1 and FIG. 3). In addition, the data indicated that FutL is significantly less efficient at promoting the synthesis of LDFT, a byproduct that was observed with other α(1,2)FTs Therefore, FutL offers advantages over the others, e.g., the ability to robustly produce 2'-FL without the concern of concurrently producing other undesirable contaminating oligosaccharides. FutL is derived from *Helicobacter mustelae* and is 70% identical to FutC at the amino acid level.

The amino acid sequence of *Bacteroides vulgatus* ATCC 8482 glycosyl transferase family protein (FutN) is set forth below (SEQ ID NO: 8; GenBank Accession Number YP_001300461 (GI:150005717), incorporated herein by reference).

```
  1 mrlikvtggl gnqmfiyafy lrmkkyypkv ridlsdmmhy kvhygyemhr vfnlphtefc 61 inqplkkvie flfffkkiyer kqapnslraf ekkyfwplly fkgfyqserf fadikdevre 121 sftfdknkan srslnmleil dkdenayslh irrgdylqpk hwattgsvcq lpyyqnaiae 181 msrrvaspsy yifsddiawv kenlplqnav yidwntdeds wqdmmlmshc khhiicnstf 241 swwgawlnpn mdktvivpsr wfqhseapdi yptgwikvpv s
```

The amino acid sequence of *Bacteroides ovatus* ATCC 8483 FutO is set forth below (SEQ ID NO: 9; GenBank Accession Number ZP_02065239 (GI:160884236), incorporated herein by reference).

```
  1 mkivnilggl gnqmfvyamy lalkeahpee eillcrrsyk gyplhngyel erifgveape
 61 aalsqlarva ypffnykswq lmrhflplrk smasgttqip fdysevtrnd nvyydgywqn
121 eknflsirdk vikaftfpef rdeknkalsd klksvktasc hirrgdylkd piygvcnsdy
181 ytraitelnq svnpdmycif sddigwcken fkfligdkev vfvdwnkgqe sfydmqlmsl
241 chyniianss fswwgawlnn nddkvvvape rwmnktlend picdnwkrik ve
```

The amino acid sequence of *Escherichia coli* O55:H7 (str. CB9615) fucosyltransferase (WbgN) is set forth below (SEQ ID NO: 10; GenBank Accession Number YP_003500093 (GI:291283275), incorporated herein by reference).

```
  1 msivvarlag glgnqmfqya kgyaesvern sslkldlrgy knytlhggfr ldklnidntf
 61 vmskkemcif pnfivraink fpklslcskr feseqyskki ngsmkgsvef igfwqneryf
121 lehkeklrei ftpininlda kelsdvirct nsysvhirrg dyvsnvealk ihglcteryy
181 idsirylker fnnlvffvfs ddiewckkyk neifsrsddv kfiegntqev dmwlmsnaky
241 hiianssfsw wgawlknYdl gitiaptpwf ereelnsfdp cpekwvriek
```

The amino acid sequence of *Bacteroides fragilis* (NCTC) 9343 alpha-1,2-fucosyltransferase (Bft1) is set forth below (SEQ ID NO: 11, GenBank Accession Number CAH09369 (GI:60494568), incorporated herein by reference).

```
  1 mffrccmkiv qiigglgnqm fqfafylalk ekyvnvkldt ssfgaythng feldkvfhve
 61 ylkasireri klsyqgseiw irvlrkllkr kkteyvepyl cfdenaisls cdkyyigywq
121 sykyftniea airgqfhfsk vlsdknefik kqmqnsnsys lhvrlgdyvn npaysnicts
181 ayynkainii qskvsepkff vfsddtvwck dhlkipnchi idwnnkeesy wdmclmtyck
241 hniianssfs wwgawlntnp eriviapgkw inddrvqvsd iipsdwicv
```

The amino acid sequence of *Bacteroides fragilis* (NCTC) 9343 fucosyl transferase (Bft3/WcfB) is set forth below (SEQ ID NO: 12; GenBank Accession Number CAH06753 (GI:60491992), incorporated herein by reference).

```
  1 mlyvilrgrl gnnlfqiata asltqnfifc tvnkdqerqv llykdsffkn ikvmkgvpdg
 61 ipyykepfhe fsripyeegk dliidgyfqs ekyfkrsvvl dlyritdelr kkiwnicgni
121 lekgetvsih vrrgdylklp halpfcgksy yknaiqyige dkifiicsdd idwckknfig
181 kryyfientt plldlyiqsl cthniisnss fswwgawlne nsnkiviapq mwfgisvklg
241 vsdllpvswv rlpnnytlgr ycfalykvve dyllnilrli wkrkknm
```

Homology Comparison Matrix of Fucosyltransferases Examined in this Study:

| Homology comparison matrix of fucosyltransferases examined in this study: | | | | | | | | | | | |
|---|---|---|---|---|---|---|---|---|---|---|---|
| | FutC | WbsJ | WbgL | WblA | WbgN | Bft1 | Bft3 | FutD | FutE | FutL | FutN | FutO |
| FutC | — | 30% | 28% | 28% | 28% | 34% | 28% | 39% | 44% | 70% | 27% | 27% |
| WbsJ | 30% | — | 33% | 33% | 36% | 36% | 40% | 30% | 35% | 30% | 33% | 36% |
| WbgL | 28% | 33% | — | 33% | 37% | 32% | 39% | 31% | 32% | 25% | 32% | 33% |

Homology comparison matrix of fucosyltransferases examined in this study:

|      | FutC | WbsJ | WbgL | WbIA | WbgN | Bft1 | Bft3 | FutD | FutE | FutL | FutN | FutO |
|------|------|------|------|------|------|------|------|------|------|------|------|------|
| WbIA | 28%  | 33%  | 33%  | —    | 36%  | 37%  | 33%  | 31%  | 38%  | 29%  | 31%  | 35%  |
| WbgN | 28%  | 36%  | 37%  | 36%  | —    | 32%  | 37%  | 30%  | 38%  | 30%  | 32%  | 35%  |
| Bft1 | 34%  | 36%  | 32%  | 37%  | 32%  | —    | 30%  | 32%  | 37%  | 33%  | 35%  | 38%  |
| Bft3 | 28%  | 40%  | 39%  | 33%  | 37%  | 30%  | —    | 30%  | 33%  | 29%  | 34%  | 35%  |
| FutD | 39%  | 30%  | 31%  | 31%  | 30%  | 32%  | 30%  | —    | 34%  | 40%  | 28%  | 31%  |
| FutE | 44%  | 35%  | 32%  | 38%  | 38%  | 37%  | 33%  | 34%  | —    | 33%  | 33%  | 36%  |
| FutL | 70%  | 30%  | 25%  | 29%  | 30%  | 33%  | 29%  | 40%  | 33%  | —    | 30%  | 28%  |
| FutN | 27%  | 33%  | 32%  | 31%  | 32%  | 35%  | 34%  | 28%  | 34%  | 30%  | —    | 37%  |
| FutO | 27%  | 36%  | 33%  | 35%  | 35%  | 38%  | 35%  | 31%  | 36%  | 28%  | 37%  | —    |

All of these proteins are found in bacteria that interact with the gastrointestinal system of higher organisms. In addition, 6 of the 10 selected incorporate fucose into their cell surface glycans. Such genes were predicted to have the strongest activity in terms of fucosyl-oligosaccharide synthesis. In this group of 10 candidates, 2 enzymes found in bacterial strains that do not incorporate fucose into cell surface glycans (WblA and WbgN) were also included. It was predicted that these candidates would have little or no fucosyl-oligosaccharide synthesis activity, and therefore might serve as a useful negative control to validate the screening approach.

Candidate α(1,2) FTs were cloned by standard molecular biological techniques into an expression plasmid. This plasmid utilizes the strong leftwards promoter of bacteriophage λ, (termed $P_L$) to direct expression of the candidate genes (Sanger, F. et al. (1982). J Mol Biol 162, 729-773). The promoter is controllable, e.g., a trp-cI construct is stably integrated the into the E. coli host's genome (at the ampC locus), and control is implemented by adding tryptophan to the growth media. Gradual induction of protein expression is accomplished using a temperature sensitive cI repressor. Another similar control strategy (temperature independent expression system) has been described (Mieschendahl et al., 1986, Bio/Technology 4:802-808). The plasmid also carries the E. coli rcsA gene to up-regulate GDP-fucose synthesis, a critical precursor for the synthesis of fucosyl-linked oligosaccharides. In addition, the plasmid carries a β-lactamase (bla) gene for maintaining the plasmid in host strains by ampicillin selection (for convenience in the laboratory) and a native thyA (thymidylate synthase) gene as an alternative means of selection in thyA⁻ hosts. Alternative selectable markers include the proBA genes to complement proline auxotrophy (Stein et al., (1984), J Bacteriol 158:2, 696-700 (1984) or purC to complement adenine auxotrophy (Parker, J., (1984), J Bacteriol 157:3, 712-7). To act as plasmid selectable markers each of these genes are first inactivated in the host cell chromosome, then wild type copies of the genes are provided on the plasmid. Alternatively a drug resistance gene may be used on the plasmid, e.g. beta-lactamase (this gene is already on the expression plasmid described above, thereby permitting selection with ampicillin). Ampicilline selection is well known in the art and described in standard manuals such as Maniatis et al., (1982) Molecular cloning, a laboratory manual. Cold Spring Harbor Laboratory, Cold Spring, N.Y.

Figure 2:
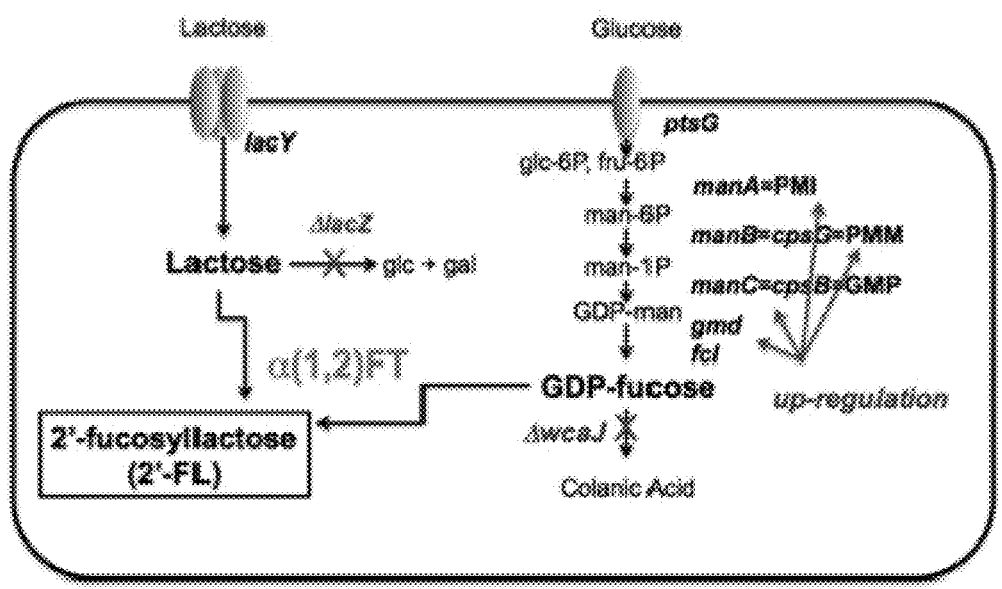
FIG. 2 is a schematic demonstrating metabolic pathways and the changes introduced into them to engineer 2'-fucosyllactose (2'-FL) synthesis in *Escherichia coli* (*E. coli*).

The expression constructs were transformed into a host strain useful for the production of 2'-FL. Biosynthesis of 2'-FL requires the generation of an enhanced cellular pool of both lactose and GDP-fucose (FIG. 2). The wild-type Escherica coli K12 prototrophic strain W3110 was selected as the parent background to test the ability of the candidates to catalyze 2'-FL production (Bachmann, B. J. (1972). Bacteriol Rev 36, 525-557). The particular W3110 derivative employed was one that previously had been modified by the introduction (at the ampC locus) of a tryptophan-inducible $P_{trpB}$ cI+ repressor cassette, generating an E. coli strain known as GI724 (LaVallie, E. R. et al. (2000). Methods Enzymol 326, 322-340). Other features of GI724 include lacIq and lacPL8 promoter mutations. E. coli strain GI724 affords economical production of recombinant proteins from the phage λ $P_L$ promoter following induction with low levels of exogenous tryptophan (LaVallie, E. R. et al. (1993). Biotechnology (NY) 11, 187-193; Mieschendahl, et al. (1986). Bio/Technology 4, 802-08). Additional genetic alterations were made to this strain to promote the biosynthesis of 2'-FL. This was achieved in strain GI724 through several manipulations of the chromosome using λ Red recombineering (Court, D. L. et al. (2002). Annu Rev Genet. 36, 361-388) and generalized P1 phage transduction.

Figure 6:
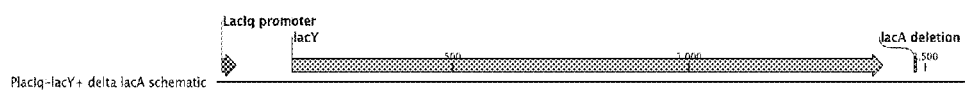
FIG. 6 is a diagram of a $P_{lacIq}$ lacY$^+$ chromosomal construct.

First, the ability of the E. coli host strain to accumulate intracellular lactose was engineered by simultaneous deletion of the endogenous β-galactosidase gene (lacZ) and the lactose operon repressor gene (lad). During construction of this deletion, the lacIq promoter was placed immediately upstream of the lactose permease gene, lacY. The modified strain maintains its ability to transport lactose from the culture medium (via LacY), but is deleted for the wild-type copy of the lacZ (β-galactosidase) gene responsible for lactose catabolism. Therefore, an intracellular lactose pool is created when the modified strain is cultured in the presence of exogenous lactose. A schematic of the $P_{lacIq}$ lacY⁺ chromosomal construct is shown in FIG. 6.

Genomic DNA sequence of the $P_{lacIq}$ lacY⁺ chromosomal construct is set forth below (SEQ ID NO: 13):

CACCATCGAATGGCGCAAAACCTTTCGCGGTATGGCATGATAGCGCCCG

GAAGAGAGTCAAGTGTAGGCTGGAGCTGCTTCGAAGTTCCTATACTTTC

TAGAGAATAGGAACTTCGGAATAGGAACTTCGGAATAGGAACTAAGGAG

GATATTCATATGTACTATTTAAAAAACACAAACTTTTGGATGTTCGGTT

TATTCTTTTTCTTTTACTTTTTTATCATGGGAGCCTACTTCCCGTTTTT

CCCGATTTGGCTACATGACATCAACCATATCAGCAAAAGTGATACGGGT

ATTATTTTTGCCGCTATTTCTCTGTTCTCGCTATTATTCCAACCGCTGT

TTGGTCTGCTTTCTGACAAACTCGGGCTGCGCAAATACCTGCTGTGGAT

TATTACCGGCATGTTAGTGATGTTTGCGCCGTTCTTTATTTTTATCTTC

GGGCCACTGTTACAATACAACATTTTAGTAGGATCGATTGTTGGTGGTA

TTTATCTAGGCTTTTGTTTTAACGCCGGTGCGCCAGCAGTAGAGGCATT

```
TATTGAGAAAGTCAGCCGTCGCAGTAATTTCGAATTTGGTCGCGCGCGG

ATGTTTGGCTGTGTTGGCTGGGCGCTGTGTGCCTCGATTGTCGGCATCA

TGTTCACCATCAATAATCAGTTTGTTTTCTGGCTGGGCTCTGGCTGTGC

ACTCATCCTCGCCGTTTTACTCTTTTTCGCCAAAACGGATGCGCCCTCT

TCTGCCACGGTTGCCAATGCGGTAGGTGCCAACCATTCGGCATTTAGCC

TTAAGCTGGCACTGGAACTGTTCAGACAGCCAAAACTGTGGTTTTTGTC

ACTGTATGTTATTGGCGTTTCCTGCACCTACGATGTTTTTGACCAACAG

TTTGCTAATTTCTTTACTTCGTTCTTTGCTACCGGTGAACAGGGTACGC

GGGTATTTGGCTACGTAACGACAATGGGCGAATTACTTAACGCCTCGAT

TATGTTCTTTGCGCCACTGATCATTAATCGCATCGGTGGGAAAAACGCC

CTGCTGCTGGCTGGCACTATTATGTCTGTACGTATTATTGGCTCATCGT

TCGCCACCTCAGCGCTGGAAGTGGTTATTCTGAAAACGCTGCATATGTT

TGAAGTACCGTTCCTGCTGGTGGGCTGCTTTAAATATATTACCAGCCAG

TTTGAAGTGCGTTTTTCAGCGACGATTTATCTGGTCTGTTTCTGCTTCT

TTAAGCAACTGGCGATGATTTTTATGTCTGTACTGGCGGGCAATATGTA

TGAAAGCATCGGTTTCCAGGGCGCTTATCTGGTGCTGGGTCTGGTGGCG

CTGGGCTTCACCTTAATTTCCGTGTTCACGCTTAGCGGCCCCGGCCCGC

TTTCCCTGCTGCGTCGTCAGGTGAATGAAGTCGCTTAAGCAATCAATGT

CGGATGCGGCGCGAGCGCCTTATCCGACCAACATATCATAACGGAGTGA

TCGCATTGTAAATTATAAAAATTGCCTGATACGCTGCGCTTATCAGGCC

TACAAGTTCAGCGATCTACATTAGCCGCATCCGGCATGAACAAAGCGCA

GGAACAAGCGTCGCA
```

Figure 7:
FIG. 7 is a diagram of the chromosomal deletion of wcaJ.

Second, the ability of the host *E. coli* strain to synthesize colanic acid, an extracellular capsular polysaccharide, was eliminated by the deletion of the wcaJ gene, encoding the UDP-glucose lipid carrier transferase (Stevenson, G. et al. (1996). J Bacteriol 178, 4885-893). In a wcaJ null background GDP-fucose accumulates in the *E. coli* cytoplasm (Dumon, C. et al. (2001). Glycoconj J 18, 465-474). A schematic of the chromosomal deletion of wcaJ is shown in FIG. 7.

The sequence of the chromosomal region bearing the ΔwcaJ::FRT mutation is set forth below (SEQ ID NO: 14):

```
GTTCGGTTATATCAATGTCAAAAACCTCACGCCGCTCAAGCTGGTGATC

AACTCCGGGAACGGCGCAGCGGGTCCGGTGGTGGACGCCATTGAAGCCC

GCTTTAAAGCCCTCGGCGCGCCCGTGGAATTAATCAAAGTGCACAACAC

GCCGGACGGCAATTTCCCCAACGGTATTCCTAACCCACTACTGCCGGAA

TGCCGCGACGACACCCGCAATGCGGTCATCAAACACGGCGCGGATATGG

GCATTGCTTTTGATGGCGATTTTGACCGCTGTTTCCTGTTTGACGAAAA

AGGGCAGTTTATTGAGGGCTACTACATTGTCGGCCTGTTGGCAGAAGCA

TTCCTCGAAAAAAATCCCGGCGCGAAGATCATCCACGATCCACGTCTCT

CCTGGAACACCGTTGATGTGGTGACTGCCGCAGGTGGCACGCCGGTAAT

GTCGAAAACCGGACACGCCTTTATTAAAGAACGTATGCGCAAGGAAGAC

GCCATCTATGGTGGCGAAATGAGCGCCCACCATTACTTCCGTGATTTCG

CTTACTGCGACAGCGGCATGATCCCGTGGCTGCTGGTCGCCGAACTGGT

GTGCCTGAAAGATAAAACGCTGGGCGAACTGGTACGCGACCGGATGGCG

GCGTTTCCGGCAAGCGGTGAGATCAACAGCAAACTGGCGCAACCCGTTG

AGGCGATTAACCGCGTGGAACAGCATTTTAGCCGTGAGGCGCTGGCGGT

GGATCGCACCGATGGCATCAGCATGACCTTTGCCGACTGGCGCTTTAAC

CTGCGCACCTCCAATACCGAACCGGTGGTGCGCCTGAATGTGGAATCGC

GCGGTGATGTGCCGCTGATGGAAGCGCGAACGCGAACTCTGCTGACGTT

GCTGAACGAGTAATGTCGGATCTTCCCTTACCCCACTGCGGGTAAGGGG

CTAATAACAGGAACAACGATGATTCCGGGGATCCGTCGACCTGCAGTTC

GAAGTTCCTATTCTCTAGAAAGTATAGGAACTTCGAAGCAGCTCCAGCC

TACAGTTAACAAAGCGGCATATTGATATGAGCTTACGTGAAAAAACCAT

CAGCGGCGCGAAGTGGTCGGCGATTGCCACGGTGATCATCATCGGCCTC

GGGCTGGTGCAGATGACCGTGCTGGCGCGGATTATCGACAACCACCAGT

TCGGCCTGCTTACCGTGTCGCTGGTGATTATCGCGCTGGCAGATACGCT

TTCTGACTTCGGTATCGCTAACTCGATTATTCAGCGAAAAGAAATCAGT

CACCTTGAACTCACCACGTTGTACTGGCTGAACGTCGGGCTGGGGATCG

TGGTGTGCGTGGCGGTGTTTTTGTTGAGTGATCTCATCGGCGACGTGCT

GAATAACCCGGACCTGGCACCGTTGATTAAAACATTATCGCTGGCGTTT

GTGGTAATCCCCCACGGGCAACAGTTCCGCGCGTTGATGCAAAAAGAGC

TGGAGTTCAACAAAATCGGCATGATCGAAACCAGCGCGGTGCTGGCGGG

CTTCACTTGTACGGTGGTTAGCGCCCATTTCTGGCCGCTGGCGATGACC

GCGATCCTCGGTTATCTGGTCAATAGTGCGGTGAGAACGCTGCTGTTTG

GCTACTTTGGCCGCAAAATTTATCGCCCCGGTCTGCATTTCTCGCTGGC

GTCGGTGGCACCGAACTTACGCTTTGGTGCCTGGCTGACGGCGGACAGC

ATCATCAACTATCTCAATACCAACCTTTCAACGCTCGTGCTGGCGCGTA

TTCTCGGCGCGGGCGTGGCAGGGGGATACAACCTGGCGTACAACGTGGC

CGTTGTGCCACCGATGAAGCTGAACCCAATCATCACCCGCGTGTTGTTT

CCGGCATTCGCCAAAATTCAGGACGATACCGAAAAGCTGCGTGTTAACT

TCTACAAGCTGCTGTCGGTAGTGGGGATTATCAACTTTCCGGCGCTGCT

CGGGCTAATGGTGGTGTCGAATAACTTTGTACCGCTGGTCTTTGGTGAG

AAGTGGAACAGCATTATTCCGGTGCTGCAATTGCTGTGTGTGGTGGGTC

TGCTGCGCTCCG
```

Figure 8:
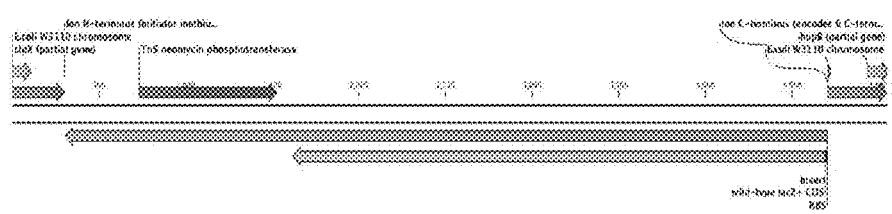
FIG. 8 is a diagram of the kan, lacZ$^+$ insertion into the ion locus.

Third, the magnitude of the cytoplasmic GDP-fucose pool was enhanced by the introduction of a null mutation into the lon gene. Lon is an ATP-dependant intracellular protease that is responsible for degrading RcsA, which is a positive transcriptional regulator of colanic acid biosynthesis in *E. coli* (Gottesman, S. & Stout, V. Mol Microbiol 5, 1599-1606 (1991)). In a lon null background, RcsA is stabilized, RcsA levels increase, the genes responsible for GDP-fucose synthesis in *E. coli* are up-regulated, and intracellular GDP-fucose concentrations are enhanced. The lon gene was almost entirely deleted and replaced by an inserted functional, wild-type, but promoter-less *E. coli* lacZ$^+$ gene (Δlon::(kan, lacZ$^+$).

λ Red recombineering was used to perform the construction. A schematic of the kan, lacZ⁺ insertion into the ion locus is shown in FIG. 8.

Genomic DNA sequence surrounding the lacZ+ insertion into the lon region in the *E. coli* strain is set forth below (SEQ ID NO: 15):

```
GTGGATGGAAGAGGTGGAAAAAGTGGTTATGGAGGAGTGGGTAATTGAT
GGTGAAAGGAAAGGGTTGGTGATTTATGGGAAGGGGGAAGGGGAAGAGG
GATGTGGTGAATAATTAAGGATTGGGATAGAATTAGTTAAGGAAAAAGG
GGGGATTTTATGTGGGGTTTAATTTTTGGTGTATTGTGGGGGTTGAATG
TGGGGGAAAGATGGGGATATAGTGAGGTAGATGTTAATAGATGGGGTGA
AGGAGAGTGGTGTGATGTGATTAGGTGGGGGAAATTAAAGTAAGAGAGA
GGTGTATGATTGGGGGGATGGGTGGAGGTGGAGTTGGAAGTTGGTATTG
TGTAGAAAGTATAGGAAGTTGAGAGGGGTTTTGAAGGTGAGGGTGGGGG
AAGGAGTGAGGGGGGAAGGGGTGGTAAAGGAAGGGGAAGAGGTAGAAAG
GGAGTGGGGAGAAAGGGTGGTGAGGGGGGATGAATGTGAGGTAGTGGGG
TATGTGGAGAAGGGAAAAGGGAAGGGGAAAGAGAAAGGAGGTAGGTTGG
AGTGGGGTTAGATGGGGATAGGTAGAGTGGGGGGTTTTATGGAGAGGAA
GGGAAGGGGAATTGGGAGGTGGGGGGGGGTGTGGTAAGGTTGGGAAGGG
GTGGAAAGTAAAGTGGATGGGTTTGTTGGGGGAAGGATGTGATGGGGG
AGGGGATGAAGATGTGATGAAGAGAGAGGATGAGGATGGTTTGGGATGA
TTGAAGAAGATGGATTGGAGGGAGGTTGTGGGGGGGGTTGGGTGGAGAG
GGTATTGGGGTATGAGTGGGGAGAAGAGAATGGGGTGGTGTGATGGG
GGGGTGTTGGGGGTGTGAGGGGAGGGGGGGGGGGTTGTTTTGTGAAGA
GGGAGGTGTGGGGTGGGGTGAATGAAGTGGAGGAGGAGGGAGGGGGGT
ATGGTGGGTGGGGAGGAGGGGGGTTGGTTGGGGAGGTGTGGTGGAGGTT
GTGAGTGAAGGGGGAAGGGAGTGGGTGGTATTGGGGAAGTGGGGGGGG
AGGATGTGGTGTGATGTGAGGTTGGTGGTGGGGAGAAAGTATGGATGAT
GGGTGATGGAATGGGGGGGGTGGATAGGGTTGATGGGGGTAGGTGGGGA
TTGGAGGAGGAAGGGAAAGATGGGATGGAGGGAGGAGGTAGTGGGATGG
AAGGGGGTGTTGTGGATGAGGATGATGTGGAGGAAGAGGATGAGGGGGT
GGGGGGAGGGGAAGTGTTGGGGAGGGTGAAGGGGGGATGGGGAGGGGG
AGGATGTGGTGGTGAGGGATGGGGATGGGTGGTTGGGGAATATGATGGT
GGAAAATGGGGGGTTTTGTGGATTGATGGAGTGTGGGGGGGTGGGTGTG
GGGGAGGGGTATGAGGAGATAGGGTTGGGTAGGGGTGATATTGGTGAAG
AGGTTGGGGGGGAATGGGGTGAGGGGTTGGTGGTGGTTTAGGGTATGGG
GGGTGGGGATTGGGAGGGGATGGGGTTGTATGGGGTTGTTGAGGAGTTG
TTGTAATAAGGGGATGTTGAAGTTGGTATTGGGAAGTTGGTATTGTGTA
GAAAGTATAGGAAGTTGGAAGGAGGTGGAGGGTAGATAAAGGGGGGGT
TATTTTTGAGAGGAGAGGAAGTGGTAATGGTAGGGAGGGGGGGTGAGGT
GGAATTGGGGGGATAGTGAGGGGGTGGAGGAGTGGTGGGGAGGAATGGG
GATATGGAAAGGGTGGATATTGAGGGATGTGGGTTGTTGGGGGTGGAGG
```

-continued
```
AGATGGGGATGGGTGGTTTGGATGAGTTGGTGTTGAGTGTAGGGGGTGA
TGTTGAAGTGGAAGTGGGGGGGGGAGTGGTGTGGGGGATAATTGAATTG
GGGGGTGGGGGAGGGGAGAGGGTTTTGGGTGGGGAAGAGGTAGGGGGTA
TAGATGTTGAGAATGGGAGATGGGAGGGGTGAAAAGAGGGGGGAGTAAG
GGGGTGGGGATAGTTTTGTTGGGGGGGTAATGGGAGGGAGTTTAGGGGG
TGTGGTAGGTGGGGGAGGTGGGAGTTGAGGGGAATGGGGGGGGGATGGG
GTGTATGGGTGGGGAGTTGAAGATGAAGGGTAATGGGGATTTGAGGAGT
AGGATGAATGGGGTAGGTTTTGGGGGTGATAAATAAGGTTTTGGGGTGA
TGGTGGGAGGGGTGAGGGGTGGTAATGAGGAGGGGATGAGGAAGTGTAT
GTGGGGTGGAGTGGAAGAAGGGTGGTTGGGGGTGGTAATGGGGGGGGGG
GTTGGAGGGTTGGAGGGAGGGGTTAGGGTGAATGGGGGTGGGTTGAGTT
AGGGGAATGTGGTTATGGAGGGGTGGAGGGGTGAAGTGATGGGGGAGGG
GGGTGAGGAGTTGTTTTTTATGGGGAATGGAGATGTGTGAAAGAAAGGG
TGAGTGGGGGTTAAATTGGGAAGGGTTATTAGGGAGGTGGATGGAAAAA
TGGATTTGGGTGGTGGTGAGATGGGGGATGGGGTGGGAGGGGGGGGGGA
GGGTGAGAGTGAGGTTTTGGGGGAGAGGGGAGTGGTGGGAGGGGGTGAT
GTGGGGGGGTTGTGAGGATGGGGTGGGGTTGGGTTGGAGTAGGGGTAGT
GTGAGGGAGAGTTGGGGGGGGGTGTGGGGGTGGGGTAGTTGAGGGAGTT
GAATGAAGTGTTTAGGTTGTGGAGGGAGATGGAGAGGGAGTTGAGGGGT
TGGGAGGGGGTTAGGATGGAGGGGGAGGATGGAGTGGAGGAGGTGGTTA
TGGGTATGAGGGAAGAGGTATTGGGTGGTGAGTTGGATGGTTTGGGGGG
ATAAAGGGAAGTGGAAAAAGTGGTGGTGGTGTTTTGGTTGGGTGAGGGG
TGGATGGGGGGTGGGTGGGAAAGAGGAGAGGGTTGATAGAGAAGTGG
GGATGGTTGGGGGTATGGGGAAAATGAGGGGGGTAAGGGGAGGAGGGGT
TGGGGTTTTGATGATATTTAATGAGGGAGTGATGGAGGGAGTGGGAGAG
GAAGGGGGGTGTAAAGGGGGATAGTGAGGAAAGGGGTGGGAGTATTTA
GGGAAAGGGGAAGAGTGTTAGGGATGGGGTGGGGTATTGGGAAGGA
TGAGGGGGGGGTGTGTGGAGGTAGGGAAAGGGATTTTTTGATGGAGGA
TTTGGGAGAGGGGGAAGGGGTGGTGTTGATGGAGGGGGGGTAGATG
GGGGAAATAATATGGGTGGGGGTGGTGTGGGGTGGGGGGGTTGATAGT
GGAGGGGGGGGAAGGATGGAGAGATTTGATGGAGGGATAGAGGGGGTG
GTGATTAGGGGGTGGGGTGATTGATTGGGGAGGGAGGAGATGATGAGA
GTGGGGTGATTAGGATGGGGGTGGAGGATTGGGGTTAGGGGTTGGGTGA
TGGGGGGTAGGGAGGGGGATGATGGGTGAGAGGATTGATTGGGAGGAT
GGGGTGGGTTTGAATATTGGGTTGATGGAGGAGATAGAGGGGGTAGGGG
TGGGAGAGGGTGTAGGAGAGGGGATGGTTGGGATAATGGGAAGAGGGGA
GGGGGTTAAAGTTGTTGTGGTTGATGAGGAGGATATGGTGGAGGATGGT
GTGGTGATGGATGAGGTGAGGATGGAGAGGATGATGGTGGTGAGGGTTA
AGGGGTGGAATGAGGAAGGGGTTGGGGTTGAGGAGGAGGAGAGGATTTT
GAATGGGGAGGTGGGGGAAAGGGAGATGGGAGGGTTGTGGTTGAATGAG
GGTGGGGTGGGGGGTGTGGAGTTGAAGGAGGGGAGGATAGAGATTGGGG
```

-continued

```
ATTTGGGGGTGGAGAGTTTGGGGTTTTGGAGGTTGAGAGGTAGTGTGA

GGGGATGGGGATAAGGAGGAGGGTGATGGATAATTTGAGGGGGAAAGG

GGGGGTGGGGGTGGGGAGGTGGGTTTGAGGGTGGGATAAAGAAAGTGTT

AGGGGTAGGTAGTGAGGGAAGTGGGGGGAGATGTGAAGTTGAGGGTGGA

GTAGAGGGGGGTGAAATGATGATTAAAGGGAGTGGGAAGATGGAAATG

GGTGATTTGTGTAGTGGGTTTATGGAGGAAGGAGAGGTGAGGGAAAATG

GGGGTGATGGGGGAGATATGGTGATGTTGGAGATAAGTGGGGTGAGTGG

AGGGGAGGAGGATGAGGGGGAGGGGGTTTTGTGGGGGGGTAAAAATGG

GGTGAGGTGAAATTGAGAGGGAAAGGAGTGTGGTGGGGTAAGGGAGG

GAGGGGGGGTTGGAGGAGAGATGAAAGGGGGAGTTAAGGGGATGAAAAA

TAATTGGGGTGTGGGGTTGGTGTAGGGAGGTTTGATGAAGATTAAATGT

GAGGGAGTAAGAAGGGGTGGGATTGTGGGTGGGAAGAAAGGGGGGATTG

AGGGTAATGGGATAGGTGAGGTTGGTGTAGATGGGGGATGGTAAGGGT

GGATGTGGGAGTTTGAGGGGAGGAGGAGAGTATGGGGGTGAGGAAGATG

GGAGGGAGGGAGGTTTGGGGGAGGGGTTGTGGTGGGGAAAGGAGGGAA

AGGGGGATTGGGGATTGAGGGTGGGGAAGTGTTGGGAAGGGGGATGGGT

GGGGGGGTGTTGGGTATTAGGGGAGGTGGGGAAAGGGGGATGTGGTGGA

AGGGGATTAAGTTGGGTAAGGGGAGGGTTTTGGGAGTGAGGAGGTTGTA

AAAGGAGGGGGAGTGAATGGGTAATGATGGTGATAGTAGGTTTGGTGAG

GTTGTGAGTGGAAAATAGTGAGGTGGGGGAAAATGGAGTAATAAAAAGA

GGGGTGGGAGGGTAATTGGGGGTTGGGAGGGTTTTTTGTGTGGGTAAG

TTAGATGGGGGATGGGGGTTGGGGTTATTAAGGGGTGTTGTAAGGGGAT

GGGTGGGGTGATATAAGTGGTGGGGGTTGGTAGGTTGAAGGATTGAAGT

GGGATATAAATTATAAAGAGGAAGAGAAGAGTGAATAAATGTGAATTGA

TGGAGAAGATTGGTGGAGGGGGTGATATGTGTAAAGGTGGGGGTGGGGG

TGGGTTAGATGGTATTATTGGTTGGGTAAGTGAATGTGTGAAAGAAGG
```

Fourth, a thyA (thymidylate synthase) mutation was introduced into the strain by P1 transduction. In the absence of exogenous thymidine, thyA strains are unable to make DNA and die. The defect can be complemented in trans by supplying a wild-type thyA gene on a multicopy plasmid (Belfort, M., Maley, G. F., and Maley, F. (1983). Proc Natl Acad Sci USA 80, 1858-861). This complementation was used here as a means of plasmid maintenance.

An additional modification that is useful for increasing the cytoplasmic pool of free lactose (and hence the final yield of 2'-FL) is the incorporation of a lacA mutation. LacA is a lactose acetyltransferase that is only active when high levels of lactose accumulate in the E. coli cytoplasm. High intracellular osmolarity (e.g., caused by a high intracellular lactose pool) can inhibit bacterial growth, and E. coli has evolved a mechanism for protecting itself from high intra cellular osmolarity caused by lactose by "tagging" excess intracellular lactose with an acetyl group using LacA, and then actively expelling the acetyl-lactose from the cell (Danchin, A. Bioessays 31, 769-773 (2009)). Production of acetyl-lactose in E. coli engineered to produce 2'-FL or other human milk oligosaccharides is therefore undesirable: it reduces overall yield. Moreover, acetyl-lactose is a side product that complicates oligosaccharide purification schemes. The incorporation of a lacA mutation resolves these problems. Sub-optimal production of fucosylated oligosaccharides occurs in strains lacking either or both of the mutations in the colanic acid pathway and the lon protease. Diversion of lactose into a side product (acetyl-lactose) occurs in strains that don't contain the lacA mutation. A schematic of the lacA deletion and corresponding genomic sequence is provided above (SEQ ID NO: 13).

The strain used to test the different α(1,2) FT candidates incorporates all the above genetic modifications and has the following genotype:
ΔampC::$P_{trp}^B$cI, Δ(lacI-lacZ)::FRT, $P_{lacIq}$lacY$^+$, ΔwcaJ::FRT, thyA::Tn10, Δlon:(npt3, lacZ$^+$), ΔlacA The E. coli strains harboring the different α(1,2) FT candidate expression plasmids were analyzed. Strains were grown in selective media (lacking thymidine) to early exponential phase. Lactose was then added to a final concentration of 1%, and tryptophan (200 μM) was added to induce expression of each candidate α(1,2) FT from the $P_L$ promoter. At the end of the induction period (~20 h) equivalent OD 600 units of each strain were harvested. Lysates were prepared and analyzed for the presence of 2'-FL by thin layer chromatography (TLC). As shown in FIG. 3A, a control strain producing FutC-Myc was efficient in the biosynthesis of 2'-FL and also produced a smaller amount of the tetrasaccharide lactodifucotetraose (LDFT). The previously characterized α(1,2) FT WbsJ from E. coli O128:B12 was also capable of catalyzing 2'-FL synthesis, although only at ~30% the level produced by FutC-Myc (FIG. 3A, lanes 5 and 6). WblA (derived from V. cholerae O22) was able to promote 2'-FL synthesis, although at a significantly lower level compared to FutC (FIG. 3A, lanes 7 and 8). This result was not unexpected, as V. cholerae O22 does not incorporate fucose into cell surface glycans (Cox, A. D. et al. (1997). Carbohydr Res 304, 191-208). The strain producing WbgL (derived from E. coli strain O126) from plasmid pG204 synthesized a significant amount of 2'-FL, approximately ~75% of the amount produced by FutC-Myc (FIG. 3A, lanes 9 and 10). WbgL was also capable of synthesizing LDFT. The strain producing FutL (derived from H. mustelae ATCC 43772) from plasmid pG216 was capable of directing the synthesis of robust amounts of 2'-FL, comparable to the levels obtained utilizing FutC-Myc and WbgL (FIG. 3B, lanes 7 and 8). Furthermore, a strain producing FutN (derived from B. vulgatus ATCC 8482) from plasmid pG217 also produced significant amounts of 2'-FL, approximately ~50% the amount produced by FutC-Myc (FIG. 3C, lanes 5 and 6). FutN is derived from the commensal bacterium B. vulgatus, and therefore may not be subject to the same concerns associated with utilization of an α(1,2) FT obtained from a pathogenic bacterium for the production of a food additive.

Figure 9:
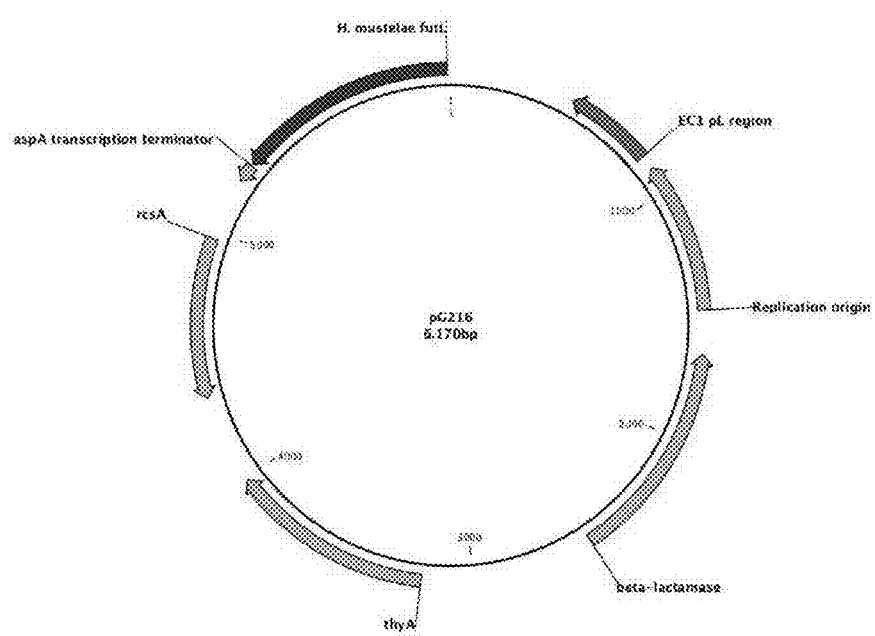
FIG. 9 is a diagram of plasmid pG204.

A map of plasmid pG204 is shown in FIG. 9. The sequence of plasmid pG204 is set forth below (SEQ ID NO: 16):

```
AATTCTAAAAATTGATTGAATGTATGCAAATAAATGCATACACCATAGG

TGTGGTTTAATTTGATGCCCTTTTTCAGGGCTGGAATGTGTAAGAGCGG

GGTTATTTATGCTGTTGTTTTTTTGTTACTCGGGAAGGGCTTTACCTCT

TCCGCATAAACGCTTCCATCAGCGTTTATAGTTAAAAAAATCTTTCGGA

ACTGGTTTTGCGCTTACCCCAACCAACAGGGGATTTGCTGCTTTCCATT

GAGCCTGTTTCTCTGCGCGACGTTCGCGGCGGCGTGTTTGTGCATCCAT
```

```
CTGGATTCTCCTGTCAGTTAGCTTTGGTGGTGTGTGGCAGTTGTAGTCC
TGAACGAAAACCCCCCGCGATTGGCACATTGGCAGCTAATCCGGAATCG
CACTTACGGCCAATGCTTCGTTTCGTATCACACACCCCAAAGCCTTCTG
CTTTGAATGCTGCCCTTCTTCAGGGCTTAATTTTTAAGAGCGTCACCTT
CATGGTGGTCAGTGCGTCCTGCTGATGTGCTCAGTATCACCGCCAGTGG
TATTTATGTCAACACCGCCAGAGATAATTTATCACCGCAGATGGTTATC
TGTATGTTTTTTATATGAATTTATTTTTTGCAGGGGGGCATTGTTTGGT
AGGTGAGAGATCAATTCTGCATTAATGAATCGGCCAACGCGCGGGGAGA
GGCGGTTTGCGTATTGGGCGCTCTTCCGCTTCCTCGCTCACTGACTCGC
TGCGCTCGGTCGTTCGGCTGCGGCGAGCGGTATCAGCTCACTCAAAGGC
GGTAATACGGTTATCCACAGAATCAGGGGATAACGCAGGAAAGAACATG
TGAGCAAAAGGCCAGCAAAAGGCCAGGAACCGTAAAAAGGCCGCGTTGC
TGGCGTTTTTCCATAGGCTCCGCCCCCCTGACGAGCATCACAAAAATCG
ACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCT
TTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCG
CCTTATCCGGTAACTATCGTCTTGAGTCCAACCCGGTAAGACACGACTT
ATCGCCACTGGCAGCAGCCACTGGTAACAGGATTAGCAGAGCGAGGTAT
GTAGGCGGTGCTACAGAGTTCTTGAAGTGGTGGCCTAACTACGGCTACA
CTAGAAGGACAGTATTTGGTATCTGCGCTCTGCTGAAGCCAGTTACCTT
CGGAAAAAGAGTTGGTAGCTCTTGATCCGGCAAACAAACCACCGCTGGT
AGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTG
GAACGAAAACTCACGTTAAGGGATTTTGGTCATGAGATTATCAAAAAGG
ATCTTCACCTAGATCCTTTTAAATTAAAAATGAAGTTTTAAATCAATCT
AAAGTATATATGAGTAAACTTGGTCTGACAGTTACCAATGCTTAATCAG
TGAGGCACCTATCTCAGCGATCTGTCTATTTCGTTCATCCATAGTTGCC
TGACTCCCCGTCGTGTAGATAACTACGATACGGGAGGGCTTACCATCTG
GCCCCAGTGCTGCAATGATACCGCGAGACCCACGCTCACCGGCTCCAGA
TTTATCAGCAATAAACCAGCCAGCCGGAAGGGCCGAGCGCAGAAGTGGT
CCTGCAACTTTATCCGCCTCCATCCAGTCTATTAATTGTTGCCGGGAAG
CTAGAGTAAGTAGTTCGCCAGTTAATAGTTTGCGCAACGTTGTTGCCAT
TGCTACAGGCATCGTGGTGTCACGCTCGTCGTTTGGTATGGCTTCATTC
AGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAA
GTTGGCCGCAGTGTTATCACTCATGGTTATGGCAGCACTGCATAATTCT
CTTACTGTCATGCCATCCGTAAGATGCTTTTCTGTGACTGGTGAGTACT
CAACCAAGTCATTCTGAGAATAGTGTATGCGGCGACCGAGTTGCTCTTG
CCCGGCGTCAATACGGGATAATACCGCGCCACATAGCAGAACTTTAAAA
GTGCTCATCATTGGAAAACGTTCTTCGGGGCGAAAACTCTCAAGGATCT
TACCGCTGTTGAGATCCAGTTCGATGTAACCCACTCGTGCACCCAACTG
ATCTTCAGCATCTTTTACTTTCACCAGCGTTTCTGGGTGAGCAAAAACA
GGAAGGCAAATGCCGCAAAAAAGGGAATAAGGGCGACACGGAAATGTT
GAATACTCATACTCTTCCTTTTTCAATATTATTGAAGCATTTATCAGGG
TTATTGTCTCATGAGCGGATACATATTTGAATGTATTTAGAAAAATAAA
CAAATAGGGGTTCCGCGCACATTTCCCCGAAAAGTGCCACCTGACGTCT
AAGAAACCATTATTATCATGACATTAACCTATAAAAATAGGCGTATCAC
GAGGCCCTTTCGTCTCGCGCGTTTCGGTGATGACGGTGAAAACCTCTGA
CACATGCAGCTCCCGGAGACGGTCACAGCTTGTCTGTAAGCGGATGCCG
GGAGCAGACAAGCCCGTCAGGGCGCGTCAGCGGGTGTTGGCGGGTGTCG
GGGCTGGCTTAACTATGCGGCATCAGAGCAGATTGTACTGAGAGTGCAC
CATATATGCGGTGTGAAATACCGCACAGATGCGTAAGGAGAAAATACCG
CATCAGGCGCCTCCTCAACCTGTATATTCGTAAACCACGCCCAATGGGA
GCTGTCTCAGGTTTGTTCCTGATTGGTTACGGCGCGTTTCGCATCATTG
TTGAGTTTTTCCGCCAGCCCGACGCGCAGTTTACCGGTGCCTGGGTGCA
GTACATCAGCATGGGCAAATTCTTTCCATCCCGATGATTGTCGCGGGT
GTGATCATGATGGTCTGGGCATATCGTCGCAGCCCACAGCAACACGTTT
CCTGAGGAACCATGAAACAGTATTTAGAACTGATGCAAAAAGTGCTCGA
CGAAGGCACACAGAAAAACGACCGTACCGGAACCGGAACGCTTTCCATT
TTTGGTCATCAGATGCGTTTTAACCTGCAAGATGGATTCCCGCTGGTGA
CAACTAAACGTTGCCACCTGCGTTCCATCATCCATGAACTGCTGTGGTT
TCTGCAGGGCGACACTAACATTGCTTATCTACACGAAAACAATGTCACC
ATCTGGGACGAATGGGCCGATGAAAACGGCGACCTCGGGCCAGTGTATG
GTAAACAGTGGCGCGCCTGGCCAACGCCAGATGGTCGTCATATTGACCA
GATCACTACGGTACTGAACCAGCTGAAAAACGACCCGGATTCGCGCCGC
ATTATTGTTTCAGCGTGGAACGTAGGCGAACTGGATAAAATGGCGCTGG
CACCGTGCCATGCATTCTTCCAGTTCTATGTGGCAGACGGCAAACTCTC
TTGCCAGCTTTATCAGCGCTCCTGTGACGTCTTCCTCGGCCTGCCGTTC
AACATTGCCAGCTACGCGTTATTGGTGCATATGATGGCGCAGCAGTGCG
ATCTGGAAGTGGGTGATTTTGTCTGGACCGGTGGCGACACGCATCTGTA
CAGCAACCATATGGATCAAACTCATCTGCAATTAAGCCGCGAACCGCGT
CCGCTGCCGAAGTTGATTATCAAACGTAAACCCGAATCCATCTTCGACT
ACCGTTTCGAAGACTTTGAGATTGAAGGCTACGATCCGCATCCGGGCAT
TAAAGCGCCGGTGGCTATCTAATTACGAAACATCCTGCCAGAGCCGACG
CCAGTGTGCGTCGGTTTTTTACCCTCCGTTAAATTCTTCGAGACGCCT
TCCCGAAGGCGCCATTCGCCATTCAGGCTGCGCAACTGTTGGGAAGGGC
GATCGGTGCGGGCCTCTTCGCTATTACGCCAGCTGGCGAAAGGGGGATG
TGCTGCAAGGCGATTAAGTTGGGTAACGCCAGGGTTTTCCCAGTCACGA
CGTTGTAAAACGACGGCCAGTGCCAAGCTTTCTTTAATGAAGCAGGGCA
```

-continued
```
TCAGGACGGTATCTTTGTGGAGAAAGCAGAGTAATCTTATTCAGCCTGA
CTGGTGGGAAACCACCAGTCAGAATGTGTTAGCGCATGTTGACAAAAAT
ACCATTAGTCACATTATCCGTCAGTCGGACGACATGGTAGATAACCTGT
TTATTATGCGTTTTGATCTTACGTTTAATATTACCTTTATGCGATGAAA
CGGTCTTGGCTTTGATATTCATTTGGTCAGAGATTTGAATGGTTCCCTG
ACCTGCCATCCACATTCGCAACATACTCGATTCGGTTCGGCTCAATGAT
AACGTCGGCATATTTAAAAACGAGGTTATCGTTGTCTCTTTTTTCAGAA
TATCGCCAAGGATATCGTCGAGAGATTCCGGTTTAATCGATTTAGAACT
GATCAATAAATTTTTTCTGACCAATAGATATTCATCAAAATGAACATTG
GCAATTGCCATAAAAACGATAAATAACGTATTGGGATGTTGATTAATGA
TGAGCTTGATACGCTGACTGTTAGAAGCATCGTGGATGAAACAGTCCTC
ATTAATAAACACCACTGAAGGGCGCTGTGAATCACAAGCTATGGCAAGG
TCATCAACGGTTTCAATGTCGTTGATTTCTCTTTTTTTAACCCCTCTAC
TCAACAGATACCCGGTTAAACCTAGTCGGGTGTAACTACATAAATCCAT
AATAATCGTTGACATGGCATACCCTCACTCAATGCGTAACGATAATTCC
CCTTACCTGAATATTTCATCATGACTAAACGGAACAACATGGGTCACCT
AATGCGCCACTCTCGCGATTTTTCAGGCGGACTTACTATCCCGTAAAGT
GTTGTATAATTTGCCTGGAATTGTCTTAAAGTAAAGTAAATGTTGCGAT
ATGTGAGTGAGCTTAAAACAAATATTTCGCTGCAGGAGTATCCTGGAAG
ATGTTCGTgAGAAGCTTACTGCTCACAAGAAAAAAGGCACGTCATCTGA
CGTGCCTTTTTTATTTGTACTACCCTGTACGATTACTGCAGCTCGAGCT
AACACGAGCTATGTTTATCCACGTTTATCCAGTGATTGACTATGGGGAT
ATAAGTATTTTTGGAGTTATATCGTACCAAGGAGTAGGATAAATAACA
ATCTGTGACGCTGATGTACCTAAATAAGCCCCCCACCAACTAAAACTAC
TATTCGCTATAATATGATGGTTAGCTAAGCTCATTAACCATAAATCTTC
TTCTTGTGATAAATCTTCTGAATAATATATATTATATTTTTTACTGAGT
AATGTTTCGATATTTCTTTACACCAAAAAATATCATCACTGAAAATAA
ACACGTCACGTATCATTGCCAAATCGCGTATTTTATTTAAAGCTTTTTT
GTAATACTCTAACGAACAAACGCCATGAGTTAAAGTAGCTGTTTTGTTT
TTTATATAATCTCCTCTTCTTATATGAATAGAAAGTGATGATTGAGATT
CAAGAATTTTTGCTGCAAGTAAATTTGCTTGTTCAGACACATTCTTTGG
AATAAAAATTCTTTTAGATCTAATATATGTTTATGGAAAAAGTGCTCA
GATTGCCAATACCCTATATATTTTTTGGATTTCCATTTTTGCGCTATAT
ATTCAAAATCATAACCATAGGCATGAAATTCATTGCAAAAACCTAAAAA
AAGAAAGATTTCAGGATATAATCTTGACCCACGAACCAAAAATTTATAA
ATATTATTAATTTTGGTGTGTAATACTGTAAATATTCCTCTGGAATTT
GTAGATTGTTTAGCCTGTAACCACCATGATCATCATTTTCAGCATAATG
ACTTATATCAAAATATAATGGTGTCCCATTAATTTTGGAAAGCGCATAC
CCAAATGAGAACTGAAAAAGTTGATTTCCAAGTCCGCCTTGTAATCTTA
TAATAGACATTATATCTCCTTCTTG
```

Figure 10:
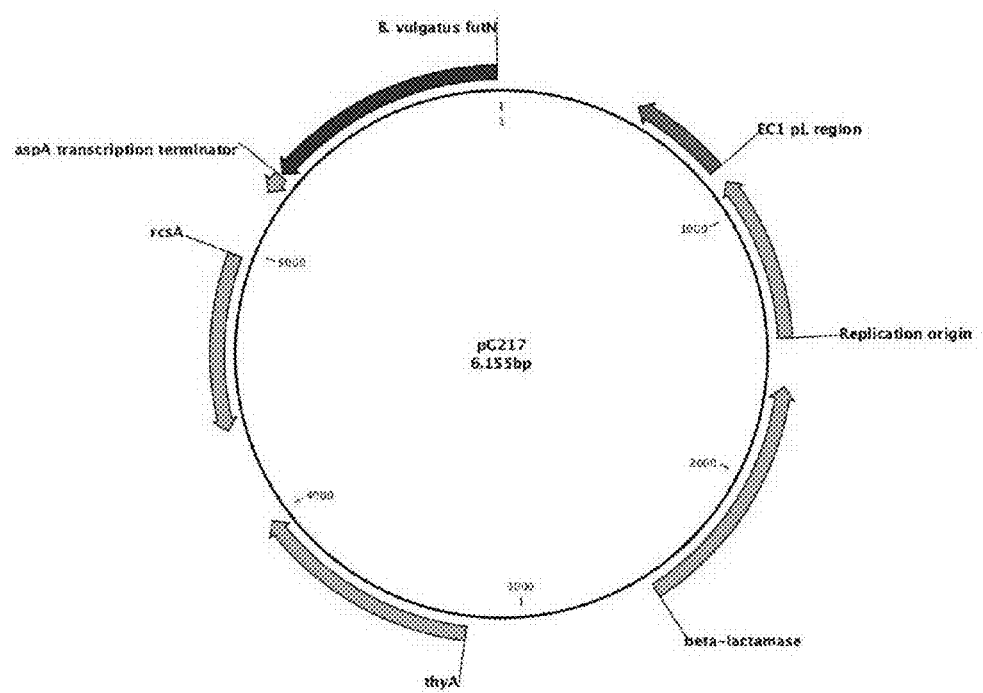
FIG. 10 is a diagram of plasmid pG216.

A map of plasmid pG216 is shown in FIG. 10. The sequence of plasmid pG216 is set forth below (SEQ ID NO: 17):

```
TCTAGAATTCTAAAAATTGATTGAATGTATGCAAATAAATGCATACACC
ATAGGTGTGGTTTAATTTGATGCCCTTTTTCAGGGCTGGAATGTGTAAG
AGCGGGGTTATTTATGCTGTTGTTTTTTTGTTACTCGGGAAGGGCTTTA
CCTCTTCCGCATAAACGCTTCCATCAGCGTTTATAGTTAAAAAAATCTT
TCGGAACTGGTTTTGCGCTTACCCCAACCAACAGGGGATTTGCTGCTTT
CCATTGAGCCTGTTTCTCTGCGCGACGTTCGCGGCGGCGTGTTTGTGCA
TCCATCTGGATTCTCCTGTCAGTTAGCTTTGGTGGTGTGTGGCAGTTGT
AGTCCTGAACGAAAACCCCCCGCGATTGGCACATTGGCAGCTAATCCGG
AATCGCACTTACGGCCAATGCTTCGTTTCGTATCACACACCCCAAAGCC
TTCTGCTTTGAATGCTGCCCTTCTTCAGGGCTTAATTTTTAAGAGCGTC
ACCTTCATGGTGGTCAGTGCGTCCTGCTGATGTGCTCAGTATCACCGCC
AGTGGTATTTATGTCAACACCGCCAGAGATAATTTATCACCGCAGATGG
TTATCTGTATGTTTTTTATATGAATTTATTTTTTGCAGGGGGGCATTGT
TTGGTAGGTGAGAGATCAATTCTGCATTAATGAATCGGCCAACGCGCGG
GGAGAGGCGGTTTGCGTATTGGGCGCTCTTCCGCTTCCTCGCTCACTGA
CTCGCTGCGCTCGGTCGTTCGGCTGCGGCGAGCGGTATCAGCTCACTCA
AAGGCGGTAATACGGTTATCCACAGAATCAGGGGATAACGCAGGAAAGA
ACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAA
AATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGAC
CCTGCCGCTTACCGGATACCTGTCCGCCTTTCTCCCTTCGGGAAGCGTG
GCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCG
CTGCGCCTTATCCGGTAACTATCGTCTTGAGTCCAACCCGGTAAGACAC
GACTTATCGCCACTGGCAGCAGCCACTGGTAACAGGATTAGCAGAGCGA
GGTATGTAGGCGGTGCTACAGAGTTCTTGAAGTGGTGGCCTAACTACGG
CTACACTAGAAGGACAGTATTTGGTATCTGCGCTCTGCTGAAGCCAGTT
ACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCT
CAGTGGAACGAAAACTCACGTTAAGGGATTTTGGTCATGAGATTATCAA
AAAGGATCTTCACCTAGATCCTTTTAAATTAAAAATGAAGTTTTAAATC
AATCTAAAGTATATATGAGTAAACTTGGTCTGACAGTTACCAATGCTTA
ATCAGTGAGGCACCTATCTCAGCGATCTGTCTATTTCGTTCATCCATAG
TTGCCTGACTCCCCGTCGTGTAGATAACTACGATACGGGAGGGCTTACC
ATCTGGCCCCAGTGCTGCAATGATACCGCGAGACCCACGCTCACCGGCT
CCAGATTTATCAGCAATAAACCAGCCAGCCGGAAGGGCCGAGCGCAGAA
GTGGTCCTGCAACTTTATCCGCCTCCATCCAGTCTATTAATTGTTGCCG
```

-continued

```
GGAAGCTAGAGTAAGTAGTTCGCCAGTTAATAGTTTGCGCAACGTTGTT
GCCATTGCTACAGGCATCGTGGTGTCACGCTCGTCGTTTGGTATGGCTT
CATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGA
AGTAAGTTGGCCGCAGTGTTATCACTCATGGTTATGGCAGCACTGCATA
ATTCTCTTACTGTCATGCCATCCGTAAGATGCTTTTCTGTGACTGGTGA
GTACTCAACCAAGTCATTCTGAGAATAGTGTATGCGGCGACCGAGTTGC
TCTTGCCCGGCGTCAATACGGGATAATACCGCGCCACATAGCAGAACTT
TAAAAGTGCTCATCATTGGAAAACGTTCTTCGGGGCGAAAACTCTCAAG
GATCTTACCGCTGTTGAGATCCAGTTCGATGTAACCCACTCGTGCACCC
AACTGATCTTCAGCATCTTTTACTTTCACCAGCGTTTCTGGGTGAGCAA
AAACAGGAAGGCAAAATGCCGCAAAAAAGGGAATAAGGGCGACACGGAA
ATGTTGAATACTCATACTCTTCCTTTTTCAATATTATTGAAGCATTTAT
CAGGGTTATTGTCTCATGAGCGGATACATATTTGAATGTATTTAGAAAA
ATAAACAAATAGGGGTTCCGCGCACATTTCCCCGAAAAGTGCCACCTGA
CGTCTAAGAAACCATTATTATCATGACATTAACCTATAAAAATAGGCGT
ATCACGAGGCCCTTTCGTCTCGCGCGTTTCGGTGATGACGGTGAAAACC
TCTGACACATGCAGCTCCCGGAGACGGTCACAGCTTGTCTGTAAGCGGA
TGCCGGGAGCAGACAAGCCCGTCAGGGCGCGTCAGCGGGTGTTGGCGGG
TGTCGGGGCTGGCTTAACTATGCGGCATCAGAGCAGATTGTACTGAGAG
TGCACCATATATGCGGTGTGAAATACCGCACAGATGCGTAAGGAGAAAA
TACCGCATCAGGCGCCTCCTCAACCTGTATATTCGTAAACCACGCCCAA
TGGGAGCTGTCTCAGGTTTGTTCCTGATTGGTTACGGCGCGTTTCGCAT
CATTGTTGAGTMTCCGCCAGCCCGACGCGCAGTTTACCGGTGCCTGGGT
GCAGTACATCAGCATGGGGCAAATTCTTTCCATCCCGATGATTGTCGCG
GGTGTGATCATGATGGTCTGGGCATATCGTCGCAGCCCACAGCAACACG
TTTCCTGAGGAACCATGAAACAGTATTTAGAACTGATGCAAAAAGTGCT
CGACGAAGGCACACAGAAAAACGACCGTACCGGAACCGGAACGCTTTCC
ATTTTTGGTCATCAGATGCGTTTTAACCTGCAAGATGGATTCCCGCTGG
TGACAACTAAACGTTGCCACCTGCGTTCCATCATCCATGAACTGCTGTG
GTTTCTGCAGGGCGACACTAACATTGCTTATCTACACGAAAACAATGTC
ACCATCTGGGACGAATGGGCCGATGAAAACGGCGACCTCGGGCCAGTGT
ATGGTAAACAGTGGCGCGCCTGGCCAACGCCAGATGGTCGTCATATTGA
CCAGATCACTACGGTACTGAACCAGCTGAAAAACGACCCGGATTCGCGC
CGCATTATTGTTTCAGCGTGGAACGTAGGCGAACTGGATAAAATGGCGC
TGGCACCGTGCCATGCATTCTTCCAGTTCTATGTGGCAGACGGCAAACT
CTCTTGCCAGCTTTATCAGCGCTCCTGTGACGTCTTCCTCGGCCTGCCG
TTCAACATTGCCAGCTACGCGTTATTGGTGCATATGATGGCGCAGCAGT
GCGATCTGGAAGTGGGTGATTTTGTCTGGACCGGTGGCGACACGCATCT
GTACAGCAACCATATGGATCAAACTCATCTGCAATTAAGCCGCGAACCG
```

```
CGTCCGCTGCCGAAGTTGATTATCAAACGTAAACCCGAATCCATCTTCG
ACTACCGTTTCGAAGACTTTGAGATTGAAGGCTACGATCCGCATCCGGG
CATTAAAGCGCCGGTGGCTATCTAATTACGAAACATCCTGCCAGAGCCG
ACGCCAGTGTGCGTCGGTTTTTTTACCCTCCGTTAAATTCTTCGAGACG
CCTTCCCGAAGGCGCCATTCGCCATTCAGGCTGCGCAACTGTTGGGAAG
GGCGATCGGTGCGGGCCTCTTCGCTATTACGCCAGCTGGCGAAAGGGGG
ATGTGCTGCAAGGCGATTAAGTTGGGTAACGCCAGGGTTTTCCCAGTCA
CGACGTTGTAAAACGACGGCCAGTGCCAAGCTTTCTTTAATGAAGCAGG
GCATCAGGACGGTATCTTTGTGGAGAAAGCAGAGTAATCTTATTCAGCC
TGACTGGTGGGAAACCACCAGTCAGAATGTGTTAGCGCATGTTGACAAA
AATACCATTAGTCACATTATCCGTCAGTCGGACGACATGGTAGATAACC
TGTTTATTATGCGTTTTGATCTTACGTTAATATTACCTTTATGCGATG
AAACGGTCTTGGCTTTGATATTCATTTGGTCAGAGATTTGAATGGTTCC
CTGACCTGCCATCCACATTCGCAACATACTCGATTCGGTTCGGCTCAAT
GATAACGTCGGCATATTTAAAAACGAGGTTATCGTTGTCTCTTTTTTCA
GAATATCGCCAAGGATATCGTCGAGAGATTCCGGTTTAATCGATTTAGA
ACTGATCAATAAATTTTTTCTGACCAATAGATATTCATCAAAATGAACA
TTGGCAATTGCCATAAAAACGATAAATAACGTATTGGGATGTTGATTAA
TGATGAGCTTGATACGCTGACTGTTAGAAGCATCGTGGATGAAACAGTC
CTCATTAATAAACACCACTGAAGGGCGCTGTGAATCACAAGCTATGGCA
AGGTCATCAACGGTTTCAATGTCGTTGATTTCTCTTTTTTTAACCCCTC
TACTCAACAGATACCCGGTTAAACCTAGTCGGGTGTAACTACATAAATC
CATAATAATCGTTGACATGGCATACCCTCACTCAATGCGTAACGATAAT
TCCCCTTACCTGAATATTTCATCATGACTAAACGGAACAACATGGGTCA
CCTAATGCGCCACTCTCGCGATTTTTCAGGCGGACTTACTATCCCGTAA
AGTGTTGTATAATTTGCCTGGAATTGTCTTAAAGTAAAGTAAATGTTGC
GATATGTGAGTGAGCTTAAAACAAATATTTCGCTGCAGGAGTATCCTGG
AAGATGTTCGTAGAAGCTTACTGCTCACAAGAAAAAAGGCACGTCATCT
GACGTGCCTTTTTTATTTGTACTACCCTGTACGATTACTGCAGCTCGAG
TTAGGATTTCGTTTCGAATTGGGATTCGATTTTAACCCAGTCTTTGCAC
AGGATGTTTTCGTTACCGTAAATCCAGTGGGACGGACCAATGATAATTT
TTTCCGGATTTTTGATCAGGTAGGCTGCCCACCAGGAGTAAGTGCTGTT
AGTGATGATACCGTGTTTGCAAGACTGCATCAGCATCATGTCCCAGTGG
GCTGCACCATCACGCGTCGTCATGTCAACAAACGGGTAACCCAGATCCA
GGTTCTGTACGAATTCCAGATCCTCGCAGAACAGGAACAGTTCCAGATT
TTGAACACGTTTTGCCATATACGCAATGGCGCGCAGCTGGTAGGAGATG
TCCAGCTGCCAGCCCAGGCGCATGTAATCGCCACGCGGATGTGAACGA
ACACAGAGTTTTTCGCAGCCAGGATCTGGGACAGTTTACGAGAGTACTG
TTCCGCGTGTTCGGTCGGGTGAGGCAGGGTGAAAGTTTGTTTGATCAGA
GGGGAGATATCTTCGAAATAGCGCGGGTCCTGAAAGTAGCCATGGAAAT
ACGCAATGCGGCTCGGTTCAAACAGTTCCGGCATGTACTCGAATACAAT
```

-continued

TTCTTTGCTAACGCGGCCCAGACCCATACGACGCAGTGCACCACGCACC

AGACGCGGCAGGTTCTGCATGTGTGCCGCGGCGATCTGCTGGGCGGACG

CACACTGCAGGTCGATCGGGAACAGGTGCAGGCCCAGTTCACGGTTACC

GTAATCGAACCAAGTGGTATCCAGCAGTACCGGAATGTTCAGGTGAGTC

TGCAGAGATTTAGCGAATGCGTACTGGAACATCTGGTTACCCAGGCCGC

CGTGCACCTGAACGATTTTGAAATCCATTATATCTCCTTCTTG

Figure 11:
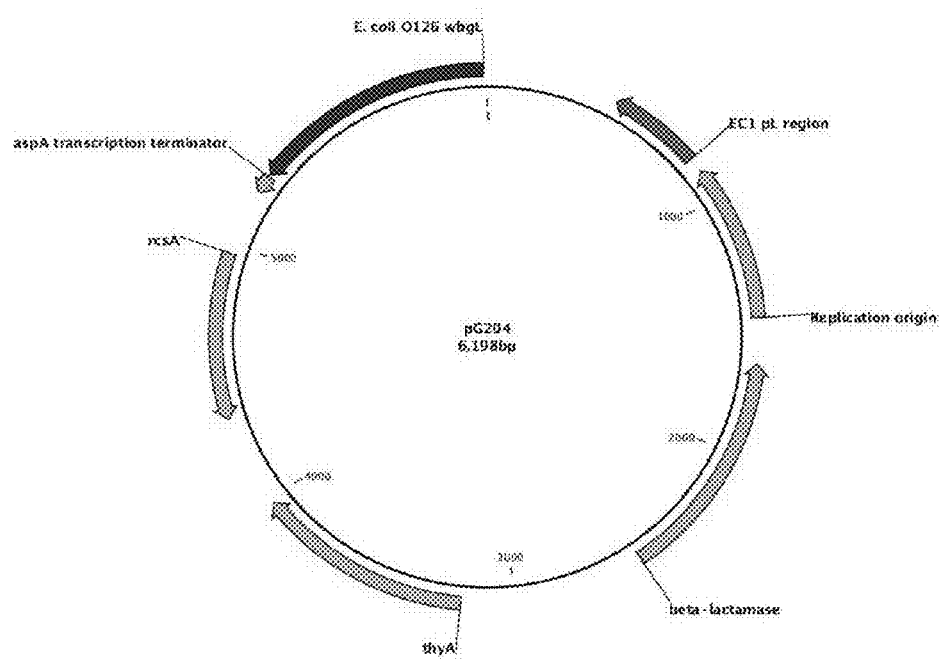
FIG. 11 is a diagram of plasmid pG217.

A map of plasmid pG217 is shown in FIG. 11. The sequence of plasmid pG217 is set forth below (SEQ ID NO: 18):

TCTAGAATTCTAAAAATTGATTGAATGTATGCAAATAAATGCATACACC

ATAGGTGTGGTTTAATTTGATGCCCTTTTTCAGGGCTGGAATGTGTAAG

AGCGGGGTTATTTATGCTGTTGTTTTTTGTTACTCGGGAAGGGCTTTA

CCTCTTCCGCATAAACGCTTCCATCAGCGTTTATAGTTAAAAAAATCTT

TCGGAACTGGTTTTGCGCTTACCCCAACCAACAGGGGATTTGCTGCTTT

CCATTGAGCCTGTTTCTCTGCGCGACGTTCGCGGCGGCGTGTTTGTGCA

TCCATCTGGATTCTCCTGTCAGTTAGCTTTGGTGGTGTGTGGCAGTTGT

AGTCCTGAACGAAAACCCCCCGCGATTGGCACATTGGCAGCTAATCCGG

AATCGCACTTACGGCCAATGCTTCGTTTCGTATCACACACCCCAAAGCC

TTCTGCTTTGAATGCTGCCCTTCTTCAGGGCTTAATTTTTAAGAGCGTC

ACCTTCATGGTGGTCAGTGCGTCCTGCTGATGTGCTCAGTATCACCGCC

AGTGGTATTTATGTCAACACCGCCAGAGATAATTTATCACCGCAGATGG

TTATCTGTATGTTTTTTATATGAATTTATTTTTTGCAGGGGGGCATTGT

TTGGTAGGTGAGAGATCAATTCTGCATTAATGAATCGGCCAACGCGCGG

GGAGAGGCGGTTTGCGTATTGGGCGCTCTTCCGCTTCCTCGCTCACTGA

CTCGCTGCGCTCGGTCGTTCGGCTGCGGCGAGCGGTATCAGCTCACTCA

AAGGCGGTAATACGGTTATCCACAGAATCAGGGGATAACGCAGGAAAGA

ACATGTGAGCAAAAGGCCAGCAAAAGGCCAGGAACCGTAAAAAGGCCGC

GTTGCTGGCGTTTTTCCATAGGCTCCGCCCCCCTGACGAGCATCACAAA

AATCGACGCTCAAGTCAGAGGTGGCGAAACCCGACAGGACTATAAAGAT

ACCAGGCGTTTCCCCCTGGAAGCTCCCTCGTGCGCTCTCCTGTTCCGAC

CCTGCCGCTTACCGGATACCTGTCCGCCTTTCTCCCTTCGGGAAGCGTG

GCGCTTTCTCATAGCTCACGCTGTAGGTATCTCAGTTCGGTGTAGGTCG

TTCGCTCCAAGCTGGGCTGTGTGCACGAACCCCCCGTTCAGCCCGACCG

CTGCGCCTTATCCGGTAACTATCGTCTTGAGTCCAACCCGGTAAGACAC

GACTTATCGCCACTGGCAGCAGCCACTGGTAACAGGATTAGCAGAGCGA

GGTATGTAGGCGGTGCTACAGAGTTCTTGAAGTGGTGGCCTAACTACGG

CTACACTAGAAGGACAGTATTTGGTATCTGCGCTCTGCTGAAGCCAGTT

ACCTTCGGAAAAAGAGTTGGTAGCTCTTGATCCGGCAAACAAACCACCG

CTGGTAGCGGTGGTTTTTTTGTTTGCAAGCAGCAGATTACGCGCAGAAA

AAAAGGATCTCAAGAAGATCCTTTGATCTTTTCTACGGGGTCTGACGCT

CAGTGGAACGAAAACTCACGTTAAGGGATTTTGGTCATGAGATTATCAA

AAAGGATCTTCACCTAGATCCTTTTAAATTAAAAATGAAGTTTTAAATC

AATCTAAAGTATATATGAGTAAACTTGGTCTGACAGTTACCAATGCTTA

ATCAGTGAGGCACCTATCTCAGCGATCTGTCTATTTCGTTCATCCATAG

TTGCCTGACTCCCCGTCGTGTAGATAACTACGATACGGGAGGGCTTACC

ATCTGGCCCCAGTGCTGCAATGATACCGCGAGACCCACGCTCACCGGCT

CCAGATTTATCAGCAATAAACCAGCCAGCCGGAAGGGCCGAGCGCAGAA

GTGGTCCTGCAACTTTATCCGCCTCCATCCAGTCTATTAATTGTTGCCG

GGAAGCTAGAGTAAGTAGTTCGCCAGTTAATAGTTTGCGCAACGTTGTT

GCCATTGCTACAGGCATCGTGGTGTCACGCTCGTCGTTTGGTATGGCTT

CATTCAGCTCCGGTTCCCAACGATCAAGGCGAGTTACATGATCCCCCAT

GTTGTGCAAAAAAGCGGTTAGCTCCTTCGGTCCTCCGATCGTTGTCAGA

AGTAAGTTGGCCGCAGTGTTATCACTCATGGTTATGGCAGCACTGCATA

ATTCTCTTACTGTCATGCCATCCGTAAGATGCTTTTCTGTGACTGGTGA

GTACTCAACCAAGTCATTCTGAGAATAGTGTATGCGGCGACCGAGTTGC

TCTTGCCCGGCGTCAATACGGGATAATACCGCGCCACATAGCAGAACTT

TAAAAGTGCTCATCATTGGAAAACGTTCTTCGGGGCGAAAACTCTCAAG

GATCTTACCGCTGTTGAGATCCAGTTCGATGTAACCCACTCGTGCACCC

AACTGATCTTCAGCATCTTTTACTTTCACCAGCGTTTCTGGGTGAGCAA

AAACAGGAAGGCAAAATGCCGCAAAAAAGGGAATAAGGGCGACACGGAA

ATGTTGAATACTCATACTCTTCCTTTTTCAATATTATTGAAGCATTTAT

CAGGGTTATTGTCTCATGAGCGGATACATATTTGAATGTATTTAGAAAA

ATAAACAAATAGGGGTTCCGCGCACATTTCCCCGAAAAGTGCCACCTGA

CGTCTAAGAAACCATTATTATCATGACATTAACCTATAAAAATAGGCGT

ATCACGAGGCCCTTTCGTCTCGCGCGTTTCGGTGATGACGGTGAAAACC

TCTGACACATGCAGCTCCCGGAGACGGTCACAGCTTGTCTGTAAGCGGA

TGCCGGGAGCAGACAAGCCCGTCAGGGCGCGTCAGCGGGTGTTGGCGGG

TGTCGGGGCTGGCTTAACTATGCGGCATCAGAGCAGATTGTACTGAGAG

TGCACCATATATGCGGTGTGAAATACCGCACAGATGCGTAAGGAGAAAA

TACCGCATCAGGCGCCTCCTCAACCTGTATATTCGTAAACCACGCCCAA

TGGGAGCTGTCTCAGGTTTGTTCCTGATTGGTTACGGCGCGTTTCGCAT

CATTGTTGAGTTTTTCCGCCAGCCCGACGCGCAGTTTACCGGTGCCTGG

GTGCAGTACATCAGCATGGGCAAATTCTTTCCATCCCGATGATTGTCG

CGGGTGTGATCATGATGGTCTGGGCATATCGTCGCAGCCCACAGCAACA

CGTTTCCTGAGGAACCATGAAACAGTATTTAGAACTGATGCAAAAAGTG

CTCGACGAAGGCACACAGAAAAACGACCGTACCGGAACCGGAACGCTTT

CCATTTTTGGTCATCAGATGCGTTTTAACCTGCAAGATGGATTCCCGCT

GGTGACAACTAAACGTTGCCACCTGCGTTCCATCATCCATGAACTGCTG

TGGTTTCTGCAGGGCGACACTAACATTGCTTATCTACACGAAAACAATG

TCACCATCTGGGACGAATGGGCCGATGAAAACGGCGACCTCGGGCCAGT

GTATGGTAAACAGTGGCGCGCCTGGCCAACGCCAGATGGTCGTCATATT

```
GACCAGATCACTACGGTACTGAACCAGCTGAAAAACGACCCGGATTCGC
GCCGCATTATTGTTTCAGCGTGGAACGTAGGCGAACTGGATAAAATGGC
GCTGGCACCGTGCCATGCATTCTTCCAGTTCTATGTGGCAGACGGCAAA
CTCTCTTGCCAGCTTTATCAGCGCTCCTGTGACGTCTTCCTCGGCCTGC
CGTTCAACATTGCCAGCTACGCGTTATTGGTGCATATGATGGCGCAGCA
GTGCGATCTGGAAGTGGGTGATTTTGTCTGGACCGGTGGCGACACGCAT
CTGTACAGCAACCATATGGATCAAACTCATCTGCAATTAAGCCGCGAAC
CGCGTCCGCTGCCGAAGTTGATTATCAAACGTAAACCCGAATCCATCTT
CGACTACCGTTTCGAAGACTTTGAGATTGAAGGCTACGATCCGCATCCG
GGCATTAAAGCGCCGGTGGCTATCTAATTACGAAACATCCTGCCAGAGC
CGACGCCAGTGTGCGTCGGTTTTTTTACCCTCCGTTAAATTCTTCGAGA
CGCCTTCCCGAAGGCGCCATTCGCCATTCAGGCTGCGCAACTGTTGGGA
AGGGCGATCGGTGCGGGCCTCTTCGCTATTACGCCAGCTGGCGAAAGGG
GGATGTGCTGCAAGGCGATTAAGTTGGGTAACGCCAGGGTTTTCCCAGT
CACGACGTTGTAAAACGACGGCCAGTGCCAAGCTTTCTTTAATGAAGCA
GGGCATCAGGACGGTATCTTTGTGGAGAAAGCAGAGTAATCTTATTCAG
CCTGACTGGTGGGAAACCACCAGTCAGAATGTGTTAGCGCATGTTGACA
AAAATACCATTAGTCACATTATCCGTCAGTCGGACGACATGGTAGATAA
CCTGTTTATTATGCGTTTTGATCTTACGTTTAATATTACCTTTATGCGA
TGAAACGGTCTTGGCTTTGATATTCATTTGGTCAGAGATTTGAATGGTT
CCCTGACCTGCCATCCACATTCGCAACATACTCGATTCGGTTCGGCTCA
ATGATAACGTCGGCATATTTAAAAACGAGGTTATCGTTGTCTCTTTTTT
CAGAATATCGCCAAGGATATCGTCGAGAGATTCCGGTTTAATCGATTTA
GAACTGATCAATAAATTTTTTCTGACCAATAGATATTCATCAAAATGAA
CATTGGCAATTGCCATAAAAACGATAAATAACGTATTGGGATGTTGATT
AATGATGAGCTTGATACGCTGACTGTTAGAAGCATCGTGGATGAAACAG
TCCTCATTAATAAACACCACTGAAGGGCGCTGTGAATCACAAGCTATGG
CAAGGTCATCAACGGTTTCAATGTCGTTGATTTCTCTTTTTTAACCCC
TCTACTCAACAGATACCCGGTTAAACCTAGTCGGGTGTAACTACATAAA
TCCATAATAATCGTTGACATGGCATACCCTCACTCAATGCGTAACGATA
ATTCCCCTTACCTGAATATTTCATCATGACTAAACGGAACAACATGGGT
CACCTAATGCGCCACTCTCGCGATTTTTCAGGCGGACTTACTATCCCGT
AAAGTGTTGTATAATTTGCCTGGAATTGTCTTAAAGTAAAGTAAATGTT
GCGATATGTGAGTGAGCTTAAAACAAATATTTCGCTGCAGGAGTATCCT
GGAAGATGTTCGTAGAAGCTTACTGCTCACAAGAAAAAAGGCACGTCAT
CTGACGTGCCTTTTTATTTGTACTACCCTGTACGATTACTGCAGCTCG
AGTTAGGATACCGGCACTTTGATCCAACCAGTCGGGTAGATATCCGGTG
CTTCGGAGTGCTGGAACCAACGGCTCGGCACAATAACAGTCTTATCCAT
ATTAGGGTTCAGCCAGGCACCCCACCAAGAAAACGTGCTGTTACAAATG
ATGTGATGTTTGCAATGAGACATCAGCATCATATCCTGCCAGGAGTCTT
CATCAGTGTTCCAGTCAATATAAACCGCATTCTGCAGTGGCAGATTTTC
TTTAACCCACGCGATATCGTCGGAGAAGATATAGTAAGATGGGCTAGCA
ACACGACGGGACATTTCCGCGATAGCATTCTGGTAATACGGCAGCTGGC
ACACGGAACCGGTAGTAGCCCAGTGTTTCGGCTGCAGATAGTCACCACG
ACGAATGTGCAGGGAAACCGCGTTTTCATCTTTGTCCAGGATTTCCAGC
ATGTTCAGGCTGCGGGAATTTGCTTTGTTCTTATCAAAGGTGAAGGATT
CACGCACTTCGTCTTTGATATCAGCGAAGAAACGCTCGCTCTGATAGAA
ACCTTTAAAGTACAGCAGCGGCCAGAAATACTTCTTCTCGAACGCACGC
AGAGAGTTCGGCGCCTGCTTGCGTTCGTAGATTTTTTAAAAAACAGGA
ATTCGATAACTTTTTTCAGCGGTTGGTTGATGCAGAATTCGGTGTGCGG
CAGGTTGAACACGCGGTGCATTTCGTAACCGTAATGGACTTTGTAATGC
ATCATGTCGCTCAGGTCGATACGGACCTTCGGGTAATACTTTTTCATAC
GCAGATAGAAAGCATAGATAAACATCTGGTTGCCCAGACCGCCAGTCAC
TTTGATCAGACGCATTATATCTCCTTCTTG
```

Fucosylated oligosaccharides produced by metabolically engineered *E. coli* cells are purified from culture broth post-fermentation. An exemplary procedure comprises five steps. (1) Clarification: Fermentation broth is harvested and cells removed by sedimentation in a preparative centrifuge at 6000×g for 30 min. Each bioreactor run yields about 5-7 L of partially clarified supernatant. (2) Product capture on coarse carbon: A column packed with coarse carbon (Calgon 12×40 TR) of ~1000 ml volume (dimension 5 cm diameter×60 cm length) is equilibrated with 1 column volume (CV) of water and loaded with clarified culture supernatant at a flow rate of 40 ml/min. This column has a total capacity of about 120 g of sugar. Following loading and sugar capture, the column is washed with 1.5 CV of water, then eluted with 2.5 CV of 50% ethanol or 25% isopropanol (lower concentrations of ethanol at this step (25-30%) may be sufficient for product elution.) This solvent elution step releases about 95% of the total bound sugars on the column and a small portion of the color bodies. In this first step capture of the maximal amount of sugar is the primary objective. Resolution of contaminants is not an objective. (3) Evaporation: A volume of 2.5 L of ethanol or isopropanol eluate from the capture column is rotary-evaporated at 56 C.° and a sugar syrup in water is generated. Alternative methods that could be used for this step include lyophilization or spray-drying. (4) Flash chromatography on fine carbon and ion exchange media: A column (GE Healthcare HiScale50/40, 5×40 cm, max pressure 20 bar) connected to a Biotage Isolera One FLASH Chromatography System is packed with 750 ml of a Darco Activated Carbon G60 (100-mesh): Celite 535 (coarse) 1:1 mixture (both column packings were obtained from Sigma). The column is equilibrated with 5 CV of water and loaded with sugar from step 3 (10-50 g, depending on the ratio of 2'-FL to contaminating lactose), using either a celite loading cartridge or direct injection. The column is connected to an evaporative light scattering (ELSD) detector to detect peaks of eluting sugars during the chromatography. A four-step gradient of isopropanol, ethanol or methanol is run in order to separate 2'-FL from monosaccharides (if present), lactose and color bodies. Fractions corresponding to sugar peaks are collected automatically in 120-ml bottles, pooled and directed to step 5. In certain purification runs from longer-than-normal fermentations, passage of the 2'-FL-containing fraction through anionexchange and cation exchange columns can remove excess protein/DNA/caramel body contaminants. Resins tested successfully for this purpose are Dowex 22

Figure 4:
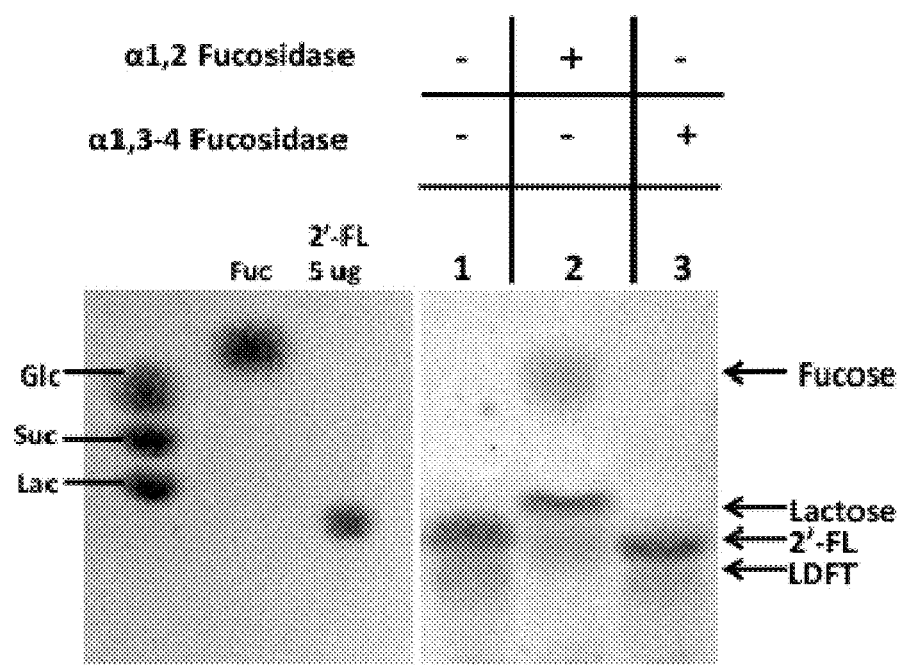
FIG. 4 is a chart and a photograph of thin layer chromatography analysis showing that fucosidase digestion confirms synthesis of bona fide 2'-FL by WbgL. Oligosaccharides produced by an *E. coli* strain expressing wbgL were isolated and subjected to overnight digestion with different fucosidases. Reaction products were analyzed by TLC. The production of fucose and lactose by treatment with α(1,2)fucosidase is illustrated in lane 2.
Figure 5:
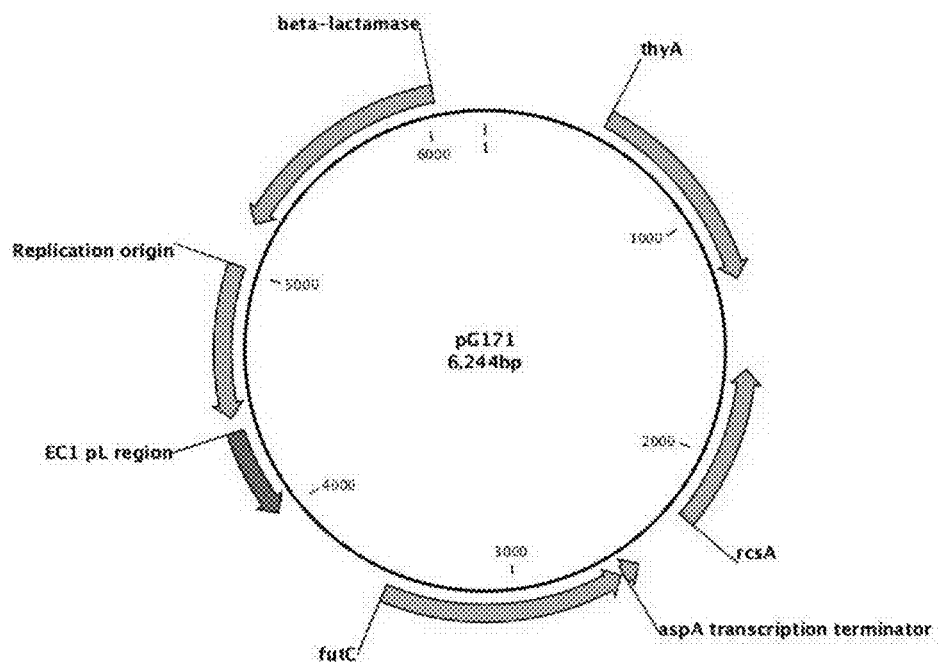
FIG. 5 is a diagram of plasmid pG171.

The identity of the major oligosaccharide synthesized by WbgL was tested and confirmed to be bona fide 2'-FL. Oligosaccharides synthesized in the WbgL strain were immobilized on a carbon column, eluted and resuspended in distilled water. This material was subjected to overnight digestion with fucosidases of different specificities, and the reactions were analyzed by TLC. As shown in FIG. 4, the untreated material consisted primarily of an oligosaccharide with the same mobility as the 2'-FL standard (lane 1). Treatment with α1,2 fucosidase yielded both lactose and fucose, while the presumptive 2'-FL spot was significantly diminished in staining intensity (lane 2). Treatment of the oligosaccharides with an α1,3-4 fucosidase had no effect. These results demonstrate that WbgL is capable of the biosynthesis of bona fide 2'-FL in metabolically engineered E. coli.

The gene screening approach was successfully utilized to identify new α(1,2) FTs for the efficient biosynthesis of 2'-FL in metabolically engineered E. coli host strains. The results of the screen are summarized in Table 1. Specifically, WbgL and FutL both direct the synthesis of 2'-FL at approximately 75% the levels attained by the previously characterized α(1,2) FT FutC. In addition, WbgL was also capable of synthesizing LDFT, which is another therapeutically useful HMO. Furthermore, FutN from the commensal enteric bacterium B. vulgatus was identified as another α(1,2) FT useful for the synthesis of fucosylated oligosaccharides. The approach described herein is useful in the analysis of additional candidate α(1,2) FTs and identifies additional enzymes that are useful for the large-scale production of HMOS.

Production Host Strains

E. coli K-12 is a well-studied bacterium which has been the subject of extensive research in microbial physiology and genetics and commercially exploited for a variety of industrial uses. The natural habitat of the parent species, E. coli, is the large bowel of mammals. E. coli K-12 has a history of safe use, and its derivatives are used in a large number of industrial applications, including the production of chemicals and drugs for human administration and consumption. E. coli K-12 was originally isolated from a convalescent diphtheria patient in 1922. Because it lacks virulence characteristics, grows readily on common laboratory media, and has been used extensively for microbial physiology and genetics research, it has become the standard bacteriological strain used in microbiological research, teaching, and production of products for industry and medicine. E. coli K-12 is now considered an enfeebled organism as a result of being maintained in the laboratory environment for over 70 years. As a result, K-12 strains are unable to colonize the intestines of humans and other animals under normal conditions. Additional information on this well known strain is available at http://epa.gov/oppt/biotech/pubs/fra/fra004.htm. In addition to E. coli K12, other bacterial strains are used as production host strains, e.g., a variety of bacterial species may be used in the oligosaccharide biosynthesis methods, e.g., Erwinia herbicola (Pantoea agglomerans), Citrobacter freundii, Pantoea citrea, Pectobacterium carotovorum, or Xanthomonas campestris. Bacteria of the genus Bacillus may also be used, including Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus, and Bacillus circulans. Similarly, bacteria of the genera Lactobacillus and Lactococcus may be modified using the methods of this invention, including but not limited to Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii, and Lactococcus lactis. Streptococcus thermophiles and Proprionibacterium freudenreichii are also suitable bacterial species for the invention described herein. Also included as part of this invention are strains, modified as described here, from the genera Enterococcus (e.g., Enterococcus faecium and Enterococcus thermophiles), Bifidobacterium (e.g., Bifidobacterium longum, Bifidobacterium infantis, and Bifidobacterium bifidum), Sporolactobacillus spp., Micromomospora spp., Micrococcus spp., Rhodococcus spp., and Pseudomonas (e.g., Pseudomonas fluorescens and Pseudomonas aeruginosa).

Suitable host strains are amenable to genetic manipulation, e.g., they maintain expression constructs, accumulate precursors of the desired end product, e.g., they maintain pools of lactose and GDP-fucose, and accumulate endproduct, e.g., 2'-FL. Such strains grow well on defined minimal media that contains simple salts and generally a single carbon source. The strains engineered as described above to produce the desired fucosylated oligosaccharide(s) are grown in a minimal media. An exemplary minimal medium used in a bioreactor, minimal "FERM" medium, is detailed below.

Ferm (10 liters): Minimal medium comprising:
  40 g $(NH_4)_2HPO_4$
  100 g $KH_2PO_4$
  10 g $MgSO_4.7H_2O$
  40 g NaOH
  Trace elements:
  1.3 g NTA (nitrilotriacetic acid)
  0.5 g $FeSO_4.7H_2O$
  0.09 g $MnCl_2.4H_2O$
  0.09 g $ZnSO_4.7H_2O$
  0.01 g $CoCl_2.6H_2O$
  0.01 g $CuCl_2.2H_2O$
  0.02 g $H_3BO_3$
  0.01 g $Na_2MoO_4.2H_2O$ (pH 6.8)
  Water to 10 liters
  DF204 antifoam (0.1 ml/L)
150 g glycerol (initial batch growth), followed by fed batch mode with a 90% glycerol-1% $MgSO_4$-1× trace elements feed, at various rates for various times.

A suitable production host strain is one that is not the same bacterial strain as the source bacterial strain from which the fucosyltransferase-encoding nucleic acid sequence was identified. For example, the fucosyltransferase-encoding nucleic acid sequence FutL was identified in Helicobacter mustelae and a suitable host strain is a bacteria other than Helicobacter mustelae, e.g., FutL is produced in production host strain E. coli K12 or any of the other strains described above.

Bacteria comprising the characteristics described herein are cultured in the presence of lactose, and a fucosylated oligosaccharide is retrieved, either from the bacterium itself or from a culture supernatant of the bacterium. The fucosylated oligosaccharide is purified for use in therapeutic or nutritional products, or the bacteria are used directly in such products.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for producing a fucosylated oligosaccharide in a bacterium comprising providing the bacterium comprising an exogenous lactose-utilizing α(1,2) fucosyltransferase enzyme, wherein an amino acid sequence of said enzyme comprises SEQ ID NO:8 and wherein said bacterium produces 2'fucosyllactose (2'-FL).

2. The method of claim 1, further comprising retrieving the fucosylated oligosaccharide from said bacterium or from a culture supernatant of said bacterium.

3. The method of claim 1, wherein said bacterium comprises a nucleic acid construct comprising an isolated nucleic acid encoding said α(1,2) fucosyltransferase enzyme.

4. The method of claim 3, wherein said nucleic acid encoding said α(1,2) fucosyltransferase enzyme is operably linked to one or more heterologous control sequences that direct the production of the α(1,2) fucosyltransferase enzyme in the bacterium.

5. The method of claim 4, wherein said heterologous control sequence comprises a bacterial promoter and operator, a bacterial ribosome binding site, a bacterial transcriptional terminator, or a plasmid selectable marker.

6. The method of claim 1, wherein said fucosylated oligosaccharide comprises 2'-fucosyllactose (2'-FL) or lactodifucotetraose (LDFT), Lacto-N-fucopentaose I (LNF I), or lacto-N-difucohexaose I (LDFH I).

7. The method of claim 1, wherein said bacterium further comprises a reduced level of β-galactosidase activity, a defective colonic acid synthesis pathway, a mutation in an ATP dependent intracellular protease, a mutation in a thyA gene, or a combination thereof.

8. The method of claim 1, wherein said method further comprises culturing said bacterium in the presence of tryptophan and in the absence of thymidine.

9. The method of claim 1, wherein an endogenous lacZ gene and an endogenous lacI gene of said bacterium are deleted.

10. The method of claim 1, wherein said bacterium comprises a lacIq gene promoter immediately upstream of a lacY gene.

11. The method of claim 1, wherein an endogenous wcaJ gene of said bacterium is deleted.

12. The method of claim 7, wherein said mutation in said ATP-dependent intracellular protease is a null mutation in a lon gene.

13. The method of claim 1, wherein said bacterium accumulates intracellular lactose in the presence of exogenous lactose.

14. The method of claim 1, wherein said bacterium accumulates intracellular GDP-fucose.

15. The method of claim 1, wherein said bacterium is a member of Streptococcus, Proprionibacterium, Enterococcus, Bifidobacterium, Sporolactobacillus, Micromomospora, Micrococcus, Rhodococcus, or Pseudomonas genus.

16. The method of claim 1, wherein said bacterium is E. coli.

17. The method of claim 1, wherein said bacterium is selected from the group consisting of Bacillus licheniformis, Bacillus subtilis, Bacillus coagulans, Bacillus thermophiles, Bacillus laterosporus, Bacillus megaterium, Bacillus mycoides, Bacillus pumilus, Bacillus lentus, Bacillus cereus, Bacillus circulans, Escherichia coli K12, Erwinia herbicola (Pantoea agglomerans), Citrobacter freundii, Pantoea citrea, Pectobacterium carotovorum, Xanthomonas campestris Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii, Lactococcus lactis, Streptococcus thermophiles, Proprionibacterium freudenreichii, Enterococcus faecium, Enterococcus thermophiles, Bifidobacterium longum, Bifidobacterium infantis, Bifidobacterium bifidum, Pseudomonas fluorescens and Pseudomonas aeruginosa.

18. A method for producing a fucosylated oligosaccharide in a bacterium comprising providing the bacterium comprising an exogenous lactose-utilizing α(1,2) fucosyltransferase enzyme, wherein an amino acid sequence of said enzyme comprises SEQ ID NO:8 and wherein said fucosylated oligosaccharide comprises a fucose group linked to a galactose group through an alpha(1,2) linkage.

* * * * *

UNITED STATES PATENT AND TRADEMARK OFFICE
CERTIFICATE OF CORRECTION

PATENT NO. : 9,029,136 B2
APPLICATION NO. : 13/557655
DATED : May 12, 2015
INVENTOR(S) : Matthew Ian Heidtman et al.

It is certified that error appears in the above-identified patent and that said Letters Patent is hereby corrected as shown below:

In the Claims:

At column 99, line 42 claim 7, "thyA" should read --*thyA*--.

At column 99, line 47-48 claim 9, "lacZ" should read --*lacZ*-- and "lacI" should read --*lacI*--.

At column 99, line 50 claim 10, "The method of claim 1," should read --"The method of claim 9,"-- and "lacIq" should read --*lacIq*-- and "lacY" should read --*lacY*--.

At column 99, line 53 claim 11, "wcaJ" should read --*wcaJ*--.

At column 100, line 15 claim 12, "lon" should read --*lon*--.

Signed and Sealed this
Twenty-seventh Day of October, 2015

Michelle K. Lee
*Director of the United States Patent and Trademark Office*

SEQUENCE LISTING

```
<160> NUMBER OF SEQ ID NOS: 18

<210> SEQ ID NO 1
<211> LENGTH: 6244
<212> TYPE: DNA
<213> ORGANISM: Artificial Sequence
<220> FEATURE:
<223> OTHER INFORMATION: plasmid pG171

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatatg cggtgtgaaa taccgcacag atgcgtaagg agaaaatacc gcatcaggcg     240
cctcctcaac ctgtatattc gtaaaccacg cccaatggga gctgtctcag gtttgttcct     300
gattggttac ggcgcgtttc gcatcattgt tgagtttttc cgccagcccg acgcgcagtt     360
taccggtgcc tgggtgcagt acatcagcat ggggcaaatt ctttccatcc cgatgattgt     420
cgcgggtgtg atcatgatgg tctgggcata tcgtcgcagc ccacagcaac acgtttcctg     480
aggaaccatg aaacagtatt tagaactgat gcaaaaagtg ctcgacgaag gcacacagaa     540
aaacgaccgt accggaaccg gaacgctttc cattttggt catcagatgc gttttaacct     600
gcaagatgga ttcccgctgg tgacaactaa acgttgccac ctgcgttcca tcatccatga     660
actgctgtgg tttctgcagg gcgacactaa cattgcttat ctacacgaaa acaatgtcac     720
catctgggac gaatgggccg atgaaaacgg cgacctcggg ccagtgtatg gtaaacagtg     780
gcgcgcctgg ccaacgccag atggtcgtca tattgaccag atcactacgg tactgaacca     840
gctgaaaaac gacccggatt cgcgccgcat tattgtttca gcgtggaacg taggcgaact     900
ggataaaatg gcgctggcac cgtgccatgc attcttccag ttctatgtgg cagacggcaa     960
actctcttgc cagctttatc agcgctcctg tgacgtcttc ctcggcctgc cgttcaacat    1020
tgccagctac gcgttattgg tgcatatgat ggcgcagcag tgcgatctgg aagtgggtga    1080
ttttgtctgg accggtggcg acacgcatct gtacagcaac catatggatc aaactcatct    1140
gcaattaagc cgcgaaccgc gtccgctgcc gaagttgatt atcaaacgta aacccgaatc    1200
catcttcgac taccgtttcg aagactttga gattgaaggc tacgatccgc atccgggcat    1260
taaagcgccg gtggctatct aattacgaaa catcctgcca gagccgacgc cagtgtgcgt    1320 cggtttttt  accctccgtt aaattcttcg agacgccttc ccgaaggcgc cattcgccat    1380
tcaggctgcg caactgttgg gaagggcgat cggtgcgggc ctcttcgcta ttacgccagc    1440
tggcgaaagg gggatgtgct gcaaggcgat taagttgggt aacgccaggg ttttcccagt    1500
cacgacgttg taaaacgacg gccagtgcca agctttcttt aatgaagcag ggcatcagga    1560
cggtatcttt gtggagaaag cagagtaatc ttattcagcc tgactggtgg gaaaccacca    1620
```

```
gtcagaatgt gttagcgcat gttgacaaaa ataccattag tcacattatc cgtcagtcgg    1680
acgacatggt agataacctg tttattatgc gttttgatct tacgtttaat attaccttta    1740
tgcgatgaaa cggtcttggc tttgatattc atttggtcag agatttgaat ggttccctga    1800
cctgccatcc acattcgcaa catactcgat tcggttcggc tcaatgataa cgtcggcata    1860
tttaaaaacg aggttatcgt tgtctctttt ttcagaatat cgccaaggat atcgtcgaga    1920
gattccggtt taatcgattt agaactgatc aataaatttt ttctgaccaa tagatattca    1980
tcaaaatgaa cattggcaat tgccataaaa acgataaata acgtattggg atgttgatta    2040
atgatgagct tgatacgctg actgttagaa gcatcgtgga tgaaacagtc ctcattaata    2100
aacaccactg aagggcgctg tgaatcacaa gctatggcaa ggtcatcaac ggtttcaatg    2160
tcgttgattt ctcttttttt aacccctcta ctcaacagat acccggttaa acctagtcgg    2220
gtgtaactac ataaatccat aataatcgtt gacatggcat accctcactc aatgcgtaac    2280
gataattccc cttacctgaa tatttcatca tgactaaacg gaacaacatg ggtcacctaa    2340
tgcgccactc tcgcgatttt tcaggcggac ttactatccc gtaaagtgtt gtataatttg    2400
cctggaattg tcttaaagta aagtaaatgt tgcgatatgt gagtgagctt aaaacaaata    2460
tttcgctgca ggagtatcct ggaagatgtt cgtagaagct tactgctcac aagaaaaaag    2520
gcacgtcatc tgacgtgcct tttttatttg tactaccctg tacgattact gcagctcgag    2580
tttaattcaa atcttcttca gaaatcaatt tttgttcagc gttatacttt tgggatttta    2640
cctcaaaatg ggattctatt ttcacccact ccttacaaag gatattctca tgcccaaaaa    2700
gccagtgttt ggggccaata atgatttttt ctggattttc tatcaaatag gccgccacc     2760 agctataagt gctattagcg ataatgccat gctgacaaga ttgcatgagc agcatgtccc    2820
aatacgcctc ttcttcttta tccctagtgg tcatgtccat aaaagggtag ccaagatcaa    2880
gattttgcgt gaattctaag tcttcgcaaa acacaaaaag ctccatgttt ggcacgcgct    2940
ttgccatata ctcaagcgcc ttttttttgat agtcaatacc aagctgacag ccaatccccca   3000 cataatcccc tcttcttata tgcacaaaca cgctgttttt agcggctaaa atcaaagaaa    3060
gcttgcactg atattcttcc tctttttttat tattattctt attattttcg ggtggtggtg    3120
gtagagtgaa ggtttgcttg attaaagggg atatagcatc aaagtatcgt ggatcttgga    3180
aatagccaaa aaaataagtc aagcggcttg gctttagcaa tttaggctcg tattcaaaaa    3240
cgatttcttg actcacccta tcaaatccca tgcatttgag cgcgtctctt actagcttgg    3300
ggaggtgttg cattttagct atagcgattt ctttcgcgct cgcatagggc aaatcaatag    3360
ggaaaagttc taattgcatt ttcctatcgc tccaatcaaa agaagtgata tctaacagca    3420
caggcgtatt agagtgtttt tgcaaacttt tagcgaaagc gtattgaaac atttgattcc    3480
caagccctcc gcaaatttgc accaccttaa aagccatatg tatatctcct tcttgaattc    3540
taaaaattga ttgaatgtat gcaaataaat gcatacacca taggtgtggt ttaatttgat    3600
gccctttttc agggctggaa tgtgtaagag cggggttatt tatgctgttg ttttttttgtt    3660 actcgggaag ggctttacct cttccgcata aacgcttcca tcagcgttta tagttaaaaa    3720 aatcttcgg aactggtttt gcgcttaccc caaccaacag gggatttgct gctttccatt    3780
gagcctgttt ctctgcgcga cgttcgcggc ggcgtgtttg tgcatccatc tggattctcc    3840
tgtcagttag ctttggtggt gtgtggcagt tgtagtcctg aacgaaaacc ccccgcgatt    3900
ggcacattgg cagctaatcc ggaatcgcac ttacggccaa tgcttcgttt cgtatcacac    3960 acccccaaagc cttctgcttt gaatgctgcc cttcttcagg gcttaatttt taagagcgtc    4020
```

```
accttcatgg tggtcagtgc gtcctgctga tgtgctcagt atcaccgcca gtggtattta    4080
tgtcaacacc gccagagata atttatcacc gcagatggtt atctgtatgt tttttatatg    4140
aatttatttt ttgcagggggg gcattgtttg gtaggtgaga gatcaattct gcattaatga    4200
atcggccaac gcgcggggag aggcggtttg cgtattgggc gctcttccgc ttcctcgctc    4260
actgactcgc tgcgctcggt cgttcggctg cggcgagcgg tatcagctca ctcaaaggcg    4320
gtaatacggt tatccacaga atcaggggat aacgcaggaa agaacatgtg agcaaaaggc    4380
cagcaaaagg ccaggaaccg taaaaaggcc gcgttgctgg cgtttttcca taggctccgc    4440
cccccctgacg agcatcacaa aaatcgacgc tcaagtcaga ggtggcgaaa cccgacagga    4500
ctataaagat accaggcgtt tccccctgga agctccctcg tgcgctctcc tgttccgacc    4560
ctgccgctta ccggatacct gtccgccttt ctcccttcgg gaagcgtggc gctttctcat    4620
agctcacgct gtaggtatct cagttcggtg taggtcgttc gctccaagct gggctgtgtg    4680
cacgaacccc ccgttcagcc cgaccgctgc gccttatccg gtaactatcg tcttgagtcc    4740
aacccggtaa gacacgactt atcgccactg gcagcagcca ctggtaacag gattagcaga    4800
gcgaggtatg taggcggtgc tacagagttc ttgaagtggt ggcctaacta cggctacact    4860
agaaggacag tatttggtat ctgcgctctg ctgaagccag ttaccttcgg aaaaagagtt    4920
ggtagctctt gatccggcaa acaaaccacc gctggtagcg gtggtttttt tgtttgcaag    4980
cagcagatta cgcgcagaaa aaaggatct caagaagatc ctttgatctt ttctacgggg    5040
tctgacgctc agtggaacga aaactcacgt taagggattt tggtcatgag attatcaaaa    5100
aggatcttca cctagatcct tttaaattaa aatgaagtt ttaaatcaat ctaaagtata    5160
tatgagtaaa cttggtctga cagttaccaa tgcttaatca gtgaggcacc tatctcagcg    5220
atctgtctat ttcgttcatc catagttgcc tgactccccg tcgtgtagat aactacgata    5280
cgggagggct taccatctgg ccccagtgct gcaatgatac cgcgagaccc acgctcaccg    5340
gctccagatt tatcagcaat aaaccagcca gccggaaggg ccgagcgcag aagtggtcct    5400
gcaactttat ccgcctccat ccagtctatt aattgttgcc gggaagctag agtaagtagt    5460
tcgccagtta atagtttgcg caacgttgtt gccattgcta caggcatcgt ggtgtcacgc    5520
tcgtcgtttg gtatggcttc attcagctcc ggttcccaac gatcaaggcg agttacatga    5580
tcccccatgt tgtgcaaaaa agcggttagc tccttcggtc ctccgatcgt tgtcagaagt    5640
aagttggccg cagtgttatc actcatggtt atggcagcac tgcataattc tcttactgtc    5700
atgccatccg taagatgctt ttctgtgact ggtgagtact caaccaagtc attctgagaa    5760
tagtgtatgc ggcgaccgag ttgctcttgc ccggcgtcaa tacgggataa taccgcgcca    5820
catagcagaa ctttaaaagt gctcatcatt ggaaaacgtt cttcggggcg aaaactctca    5880
aggatcttac cgctgttgag atccagttcg atgtaaccca ctcgtgcacc caactgatct    5940
tcagcatctt ttactttcac cagcgtttct gggtgagcaa aaacaggaag gcaaaatgcc    6000
gcaaaaaagg gaataagggc gacacggaaa tgttgaatac tcatactctt ccttttttcaa    6060
tattattgaa gcatttatca gggttattgt ctcatgagcg gatacatatt tgaatgtatt    6120
tagaaaaata aacaaatagg ggttccgcgc acatttcccc gaaaagtgcc acctgacgtc    6180
taagaaacca ttattatcat gacattaacc tataaaaata ggcgtatcac gaggcccttt    6240
cgtc                                                                 6244
```

<210> SEQ ID NO 2

<211> LENGTH: 298
<212> TYPE: PRT
<213> ORGANISM: Helicobacter pylori

<400> SEQUENCE: 2

Met Ala Phe Lys Val Val Gln Ile Cys Gly Gly Leu Gly Asn Gln Met
1               5                   10                  15

Phe Gln Tyr Ala Phe Ala Lys Ser Leu Gln Lys His Leu Asn Thr Pro
            20                  25                  30

Val Leu Leu Asp Ile Thr Ser Phe Asp Trp Ser Asn Arg Lys Met Gln
        35                  40                  45

Leu Glu Leu Phe Pro Ile Asp Leu Pro Tyr Ala Ser Ala Lys Glu Ile
    50                  55                  60

Ala Ile Ala Lys Met Gln His Leu Pro Lys Leu Val Arg Asp Thr Leu
65                  70                  75                  80

Lys Cys Met Gly Phe Asp Arg Val Ser Gln Glu Ile Val Phe Glu Tyr
                85                  90                  95

Glu Pro Gly Leu Leu Lys Pro Ser Arg Leu Thr Tyr Phe Tyr Gly Tyr
            100                 105                 110

Phe Gln Asp Pro Arg Tyr Phe Asp Ala Ile Ser Pro Leu Ile Lys Gln
        115                 120                 125

Thr Phe Thr Leu Pro Pro Glu Asn Gly Asn Asn Lys Lys Lys Glu
    130                 135                 140

Glu Glu Tyr His Arg Lys Leu Ala Leu Ile Leu Ala Ala Lys Asn Ser
145                 150                 155                 160

Val Phe Val His Val Arg Arg Gly Asp Tyr Val Gly Ile Gly Cys Gln
                165                 170                 175

Leu Gly Ile Asp Tyr Gln Lys Lys Ala Leu Glu Tyr Ile Ala Lys Arg
            180                 185                 190

Val Pro Asn Met Glu Leu Phe Val Phe Cys Glu Asp Leu Lys Phe Thr
        195                 200                 205

Gln Asn Leu Asp Leu Gly Tyr Pro Phe Met Asp Met Thr Thr Arg Asp
    210                 215                 220

Lys Glu Glu Glu Ala Tyr Trp Asp Met Leu Leu Met Gln Ser Cys Lys
225                 230                 235                 240

His Gly Ile Ile Ala Asn Ser Thr Tyr Ser Trp Trp Ala Ala Tyr Leu
                245                 250                 255

Ile Asn Asn Pro Glu Lys Ile Ile Gly Pro Lys His Trp Leu Phe
            260                 265                 270

Gly His Glu Asn Ile Leu Cys Lys Glu Trp Val Lys Ile Glu Ser His
        275                 280                 285

Phe Glu Val Lys Ser Lys Lys Tyr Asn Ala
    290                 295

<210> SEQ ID NO 3
<211> LENGTH: 281
<212> TYPE: PRT
<213> ORGANISM: Vibrio cholerae

<400> SEQUENCE: 3

Met Ile Val Met Lys Ile Ser Gly Gly Leu Gly Asn Gln Leu Phe Gln
1               5                   10                  15

Tyr Ala Val Gly Arg Ala Ile Ala Ile Gln Tyr Gly Val Pro Leu Lys
            20                  25                  30

Leu Asp Val Ser Ala Tyr Lys Asn Tyr Lys Leu His Asn Gly Tyr Arg
        35                  40                  45

Leu Asp Gln Phe Asn Ile Asn Ala Asp Ile Ala Asn Glu Asp Glu Ile
    50                  55                  60

Phe His Leu Lys Gly Ser Ser Asn Arg Leu Ser Arg Ile Leu Arg Arg
65                  70                  75                  80

Leu Gly Trp Leu Lys Lys Asn Thr Tyr Tyr Ala Glu Lys Gln Arg Thr
                85                  90                  95

Ile Tyr Asp Val Ser Val Phe Met Gln Ala Pro Arg Tyr Leu Asp Gly
            100                 105                 110

Tyr Trp Gln Asn Glu Gln Tyr Phe Ser Gln Ile Arg Ala Val Leu Leu
        115                 120                 125

Gln Glu Leu Trp Pro Asn Gln Pro Leu Ser Ile Asn Ala Gln Ala His
130                 135                 140

Gln Ile Lys Ile Gln Gln Thr His Ala Val Ser Ile His Val Arg Arg
145                 150                 155                 160

Gly Asp Tyr Leu Asn His Pro Glu Ile Gly Val Leu Asp Ile Asp Tyr
                165                 170                 175

Tyr Lys Arg Ala Val Asp Tyr Ile Lys Glu Lys Ile Glu Ala Pro Val
            180                 185                 190

Phe Phe Val Phe Ser Asn Asp Val Ala Trp Cys Lys Asp Asn Phe Asn
        195                 200                 205

Phe Ile Asp Ser Pro Val Phe Ile Glu Asp Thr Gln Thr Glu Ile Asp
210                 215                 220

Asp Leu Met Leu Met Cys Gln Cys Gln His Asn Ile Val Ala Asn Ser
225                 230                 235                 240

Ser Phe Ser Trp Trp Ala Ala Trp Leu Asn Ser Asn Val Asp Lys Ile
                245                 250                 255

Val Ile Ala Pro Lys Thr Trp Met Ala Glu Asn Pro Lys Gly Tyr Lys
            260                 265                 270

Trp Val Pro Asp Ser Trp Arg Glu Ile
        275                 280

<210> SEQ ID NO 4
<211> LENGTH: 297
<212> TYPE: PRT
<213> ORGANISM: Escherichia coli

<400> SEQUENCE: 4

Met Ser Ile Ile Arg Leu Gln Gly Gly Leu Gly Asn Gln Leu Phe Gln
1               5                   10                  15

Phe Ser Phe Gly Tyr Ala Leu Ser Lys Ile Asn Gly Thr Pro Leu Tyr
            20                  25                  30

Phe Asp Ile Ser His Tyr Ala Glu Asn Asp Asp His Gly Gly Tyr Arg
        35                  40                  45

Leu Asn Asn Leu Gln Ile Pro Glu Glu Tyr Leu Gln Tyr Tyr Thr Pro
    50                  55                  60

Lys Ile Asn Asn Ile Tyr Lys Phe Leu Val Arg Gly Ser Arg Leu Tyr
65                  70                  75                  80

Pro Glu Ile Phe Leu Phe Leu Gly Phe Cys Asn Glu Phe His Ala Tyr
                85                  90                  95

Gly Tyr Asp Phe Glu Tyr Ile Ala Gln Lys Trp Lys Ser Lys Lys Tyr
            100                 105                 110

Ile Gly Tyr Trp Gln Ser Glu His Phe Phe His Lys His Ile Leu Asp
        115                 120                 125

Leu Lys Glu Phe Phe Ile Pro Lys Asn Val Ser Glu Gln Ala Asn Leu

```
            130                 135                 140
Leu Ala Ala Lys Ile Leu Glu Ser Gln Ser Ser Leu Ser Ile His Ile
145                 150                 155                 160

Arg Arg Gly Asp Tyr Ile Lys Asn Lys Thr Ala Thr Leu Thr His Gly
                165                 170                 175

Val Cys Ser Leu Glu Tyr Tyr Lys Lys Ala Leu Asn Lys Ile Arg Asp
                180                 185                 190

Leu Ala Met Ile Arg Asp Val Phe Ile Phe Ser Asp Asp Ile Phe Trp
                195                 200                 205

Cys Lys Glu Asn Ile Glu Thr Leu Leu Ser Lys Lys Tyr Asn Ile Tyr
            210                 215                 220

Tyr Ser Glu Asp Leu Ser Gln Glu Glu Asp Leu Trp Leu Met Ser Leu
225                 230                 235                 240

Ala Asn His His Ile Ile Ala Asn Ser Ser Phe Ser Trp Trp Gly Ala
                245                 250                 255

Tyr Leu Gly Thr Ser Ala Ser Gln Ile Val Ile Tyr Pro Thr Pro Trp
                260                 265                 270

Tyr Asp Ile Thr Pro Lys Asn Thr Tyr Ile Pro Ile Val Asn His Trp
                275                 280                 285

Ile Asn Val Asp Lys His Ser Ser Cys
            290                 295

<210> SEQ ID NO 5
<211> LENGTH: 293
<212> TYPE: PRT
<213> ORGANISM: Helicobacter bilis

<400> SEQUENCE: 5

Met Gly Asp Tyr Lys Ile Val Glu Leu Thr Cys Gly Leu Gly Asn Gln
1               5                   10                  15

Met Phe Gln Tyr Ala Phe Ala Lys Ala Leu Gln Lys His Leu Gln Val
                20                  25                  30

Pro Val Leu Leu Asp Lys Thr Trp Tyr Asp Thr Gln Asp Asn Ser Thr
            35                  40                  45

Gln Phe Ser Leu Asp Ile Phe Asn Val Asp Leu Glu Tyr Ala Thr Asn
        50                  55                  60

Thr Gln Ile Glu Lys Ala Lys Ala Arg Val Ser Lys Leu Pro Gly Leu
65                  70                  75                  80

Leu Arg Lys Met Phe Gly Leu Lys Lys His Asn Ile Ala Tyr Ser Gln
                85                  90                  95

Ser Phe Asp Phe His Asp Glu Tyr Leu Leu Pro Asn Asp Phe Thr Tyr
                100                 105                 110

Phe Ser Gly Phe Phe Gln Asn Ala Lys Tyr Leu Lys Gly Leu Glu Gln
            115                 120                 125

Glu Leu Lys Ser Ile Phe Tyr Tyr Asp Ser Asn Asn Phe Ser Asn Phe
130                 135                 140

Gly Lys Gln Arg Leu Glu Leu Ile Leu Gln Ala Lys Asn Ser Ile Phe
145                 150                 155                 160

Ile His Ile Arg Arg Gly Asp Tyr Cys Lys Ile Gly Trp Glu Leu Gly
                165                 170                 175

Met Asp Tyr Tyr Lys Arg Ala Ile Gln Tyr Ile Met Asp Arg Val Glu
                180                 185                 190

Glu Pro Lys Phe Phe Ile Phe Gly Ala Thr Asp Met Ser Phe Thr Glu
            195                 200                 205
```

```
Gln Phe Gln Lys Asn Leu Gly Leu Asn Glu Asn Asn Ser Ala Asn Leu
    210                 215                 220

Ser Glu Lys Thr Ile Thr Gln Asp Asn Gln His Glu Asp Met Phe Leu
225                 230                 235                 240

Met Cys Tyr Cys Lys His Ala Ile Leu Ala Asn Ser Ser Tyr Ser Phe
                245                 250                 255

Trp Ser Ala Tyr Leu Asn Asn Asp Ala Asn Asn Ile Val Ile Ala Pro
                260                 265                 270

Thr Pro Trp Leu Leu Asp Asn Asp Asn Ile Ile Cys Asp Asp Trp Ile
            275                 280                 285

Lys Ile Ser Ser Lys
    290

<210> SEQ ID NO 6
<211> LENGTH: 257
<212> TYPE: PRT
<213> ORGANISM: Helicobacter cinaedi

<400> SEQUENCE: 6

Met Leu Phe Pro Phe Lys Phe Ile Tyr Asn Arg Leu Arg Tyr Lys Ala
1               5                   10                  15

Ile Arg Leu Ile Arg Arg Arg Ala Ser Tyr Arg Pro Phe Tyr Glu Phe
                20                  25                  30

Tyr Ala His Ile Val Trp Gly Glu Gly Val Val Asn Asp Arg Ile
            35                  40                  45

Met Lys His Tyr Arg Glu Ser Ser Phe Lys Pro Tyr Ala Phe Pro Tyr
    50                  55                  60

Gly Ile Asn Met Ser Phe Val Tyr Ser Asn Asp Val Tyr Ala Leu Leu
65                  70                  75                  80

Lys Asp Asp Phe Arg Leu Lys Ile Pro Leu Arg Tyr Asp Asn Ala Met
                85                  90                  95

Leu Lys Lys Gln Ile Gln Asn Thr Asp Lys Ser Val Phe Leu His Ile
            100                 105                 110

Arg Arg Gly Asp Tyr Leu Gln Ser Glu Gly Leu Tyr Val Val Leu Gly
        115                 120                 125

Val Thr Tyr Tyr Gln Lys Ala Leu Glu Ile Leu Lys Ser Lys Ile Thr
    130                 135                 140

Asn Pro His Ile Phe Val Phe Ser Asn Asp Met Cys Trp Cys Lys Glu
145                 150                 155                 160

Tyr Leu Met Arg Tyr Val Asp Phe Ser Gly Cys Thr Ile Asp Phe Ile
                165                 170                 175

Glu Gly Asn Thr Glu Gly Asn Ala Val Glu Glu Met Glu Leu Met Arg
            180                 185                 190

Ser Cys Gln His Ala Ile Ile Ala Asn Ser Thr Phe Ser Trp Trp Ala
        195                 200                 205

Ala Tyr Leu Ile Glu Asn Pro Asp Lys Ile Val Ile Met Pro Lys Glu
    210                 215                 220

Tyr Leu Asn Asp Ser Ser Arg Phe Leu Pro Lys Gln Phe Leu Ala Leu
225                 230                 235                 240

Lys Asn Trp Phe Leu Val Asp His Ile Trp Gly Ser Val Glu Leu Ala
                245                 250                 255

Asn

<210> SEQ ID NO 7
<211> LENGTH: 286
```

<212> TYPE: PRT
<213> ORGANISM: Helicobacter mustelae

<400> SEQUENCE: 7

```
Met Asp Phe Lys Ile Val Gln Val His Gly Gly Leu Gly Asn Gln Met
1               5                   10                  15

Phe Gln Tyr Ala Phe Ala Lys Ser Leu Gln Thr His Leu Asn Ile Pro
            20                  25                  30

Val Leu Leu Asp Thr Thr Trp Phe Asp Tyr Gly Asn Arg Glu Leu Gly
        35                  40                  45

Leu His Leu Phe Pro Ile Asp Leu Gln Cys Ala Ser Ala Gln Gln Ile
    50                  55                  60

Ala Ala Ala His Met Gln Asn Leu Pro Arg Leu Val Arg Gly Ala Leu
65                  70                  75                  80

Arg Arg Met Gly Leu Gly Arg Val Ser Lys Glu Ile Val Phe Glu Tyr
                85                  90                  95

Met Pro Glu Leu Phe Glu Pro Ser Arg Ile Ala Tyr Phe His Gly Tyr
            100                 105                 110

Phe Gln Asp Pro Arg Tyr Phe Glu Asp Ile Ser Pro Leu Ile Lys Gln
        115                 120                 125

Thr Phe Thr Leu Pro His Pro Thr Glu His Ala Glu Gln Tyr Ser Arg
    130                 135                 140

Lys Leu Ser Gln Ile Leu Ala Ala Lys Asn Ser Val Phe Val His Ile
145                 150                 155                 160

Arg Arg Gly Asp Tyr Met Arg Leu Gly Trp Gln Leu Asp Ile Ser Tyr
                165                 170                 175

Gln Leu Arg Ala Ile Ala Tyr Met Ala Lys Arg Val Gln Asn Leu Glu
            180                 185                 190

Leu Phe Leu Phe Cys Glu Asp Leu Glu Phe Val Gln Asn Leu Asp Leu
        195                 200                 205

Gly Tyr Pro Phe Val Asp Met Thr Thr Arg Asp Gly Ala Ala His Trp
    210                 215                 220

Asp Met Met Leu Met Gln Ser Cys Lys His Gly Ile Ile Thr Asn Ser
225                 230                 235                 240

Thr Tyr Ser Trp Trp Ala Ala Tyr Leu Ile Lys Asn Pro Glu Lys Ile
                245                 250                 255

Ile Ile Gly Pro Ser His Trp Ile Tyr Gly Asn Glu Asn Ile Leu Cys
            260                 265                 270

Lys Asp Trp Val Lys Ile Glu Ser Gln Phe Glu Thr Lys Ser
        275                 280                 285
```

<210> SEQ ID NO 8
<211> LENGTH: 281
<212> TYPE: PRT
<213> ORGANISM: Bacteroides vulgatus

<400> SEQUENCE: 8

```
Met Arg Leu Ile Lys Val Thr Gly Gly Leu Gly Asn Gln Met Phe Ile
1               5                   10                  15

Tyr Ala Phe Tyr Leu Arg Met Lys Lys Tyr Tyr Pro Lys Val Arg Ile
            20                  25                  30

Asp Leu Ser Asp Met Met His Tyr Lys Val His Tyr Gly Tyr Glu Met
        35                  40                  45

His Arg Val Phe Asn Leu Pro Thr Glu Phe Cys Ile Asn Gln Pro
    50                  55                  60
```

```
Leu Lys Lys Val Ile Glu Phe Leu Phe Phe Lys Ile Tyr Glu Arg
 65                  70                  75                  80

Lys Gln Ala Pro Asn Ser Leu Arg Ala Phe Glu Lys Lys Tyr Phe Trp
                 85                  90                  95

Pro Leu Leu Tyr Phe Lys Gly Phe Tyr Gln Ser Glu Arg Phe Phe Ala
            100                 105                 110

Asp Ile Lys Asp Glu Val Arg Glu Ser Phe Thr Phe Asp Lys Asn Lys
            115                 120                 125

Ala Asn Ser Arg Ser Leu Asn Met Leu Glu Ile Leu Asp Lys Asp Glu
            130                 135                 140

Asn Ala Val Ser Leu His Ile Arg Arg Gly Asp Tyr Leu Gln Pro Lys
145                 150                 155                 160

His Trp Ala Thr Thr Gly Ser Val Cys Gln Leu Pro Tyr Tyr Gln Asn
                165                 170                 175

Ala Ile Ala Glu Met Ser Arg Arg Val Ala Ser Pro Ser Tyr Tyr Ile
            180                 185                 190

Phe Ser Asp Asp Ile Ala Trp Val Lys Glu Asn Leu Pro Leu Gln Asn
            195                 200                 205

Ala Val Tyr Ile Asp Trp Asn Thr Asp Glu Asp Ser Trp Gln Asp Met
            210                 215                 220

Met Leu Met Ser His Cys Lys His His Ile Ile Cys Asn Ser Thr Phe
225                 230                 235                 240

Ser Trp Trp Gly Ala Trp Leu Asn Pro Asn Met Asp Lys Thr Val Ile
                245                 250                 255

Val Pro Ser Arg Trp Phe Gln His Ser Glu Ala Pro Asp Ile Tyr Pro
            260                 265                 270

Thr Gly Trp Ile Lys Val Pro Val Ser
            275                 280

<210> SEQ ID NO 9
<211> LENGTH: 292
<212> TYPE: PRT
<213> ORGANISM: Bacteroides ovatus

<400> SEQUENCE: 9

Met Lys Ile Val Asn Ile Leu Gly Gly Leu Gly Asn Gln Met Phe Val
 1                   5                  10                  15

Tyr Ala Met Tyr Leu Ala Leu Lys Glu Ala His Pro Glu Glu Glu Ile
                 20                  25                  30

Leu Leu Cys Arg Arg Ser Tyr Lys Gly Tyr Pro Leu His Asn Gly Tyr
             35                  40                  45

Glu Leu Glu Arg Ile Phe Gly Val Glu Ala Pro Glu Ala Ala Leu Ser
 50                  55                  60

Gln Leu Ala Arg Val Ala Tyr Pro Phe Phe Asn Tyr Lys Ser Trp Gln
 65                  70                  75                  80

Leu Met Arg His Phe Leu Pro Leu Arg Lys Ser Met Ala Ser Gly Thr
                 85                  90                  95

Thr Gln Ile Pro Phe Asp Tyr Ser Glu Val Thr Arg Asn Asp Asn Val
            100                 105                 110

Tyr Tyr Asp Gly Tyr Trp Gln Asn Glu Lys Asn Phe Leu Ser Ile Arg
            115                 120                 125

Asp Lys Val Ile Lys Ala Phe Thr Phe Pro Glu Phe Arg Asp Glu Lys
            130                 135                 140

Asn Lys Ala Leu Ser Asp Lys Leu Lys Ser Val Lys Thr Ala Ser Cys
145                 150                 155                 160
```

```
His Ile Arg Arg Gly Asp Tyr Leu Lys Asp Pro Ile Tyr Gly Val Cys
                165                 170                 175

Asn Ser Asp Tyr Tyr Thr Arg Ala Ile Thr Glu Leu Asn Gln Ser Val
            180                 185                 190

Asn Pro Asp Met Tyr Cys Ile Phe Ser Asp Ile Gly Trp Cys Lys
        195                 200                 205

Glu Asn Phe Lys Phe Leu Ile Gly Asp Lys Glu Val Val Phe Val Asp
    210                 215                 220

Trp Asn Lys Gly Gln Glu Ser Phe Tyr Asp Met Gln Leu Met Ser Leu
225                 230                 235                 240

Cys His Tyr Asn Ile Ile Ala Asn Ser Ser Phe Ser Trp Trp Gly Ala
                245                 250                 255

Trp Leu Asn Asn Asn Asp Asp Lys Val Val Ala Pro Glu Arg Trp
            260                 265                 270

Met Asn Lys Thr Leu Glu Asn Asp Pro Ile Cys Asp Asn Trp Lys Arg
        275                 280                 285

Ile Lys Val Glu
    290

<210> SEQ ID NO 10
<211> LENGTH: 290
<212> TYPE: PRT
<213> ORGANISM: Escherichia coli

<400> SEQUENCE: 10

Met Ser Ile Val Val Ala Arg Leu Ala Gly Gly Leu Gly Asn Gln Met
1               5                   10                  15

Phe Gln Tyr Ala Lys Gly Tyr Ala Glu Ser Val Glu Arg Asn Ser Ser
                20                  25                  30

Leu Lys Leu Asp Leu Arg Gly Tyr Lys Asn Tyr Thr Leu His Gly Gly
            35                  40                  45

Phe Arg Leu Asp Lys Leu Asn Ile Asp Asn Thr Phe Val Met Ser Lys
50                  55                  60

Lys Glu Met Cys Ile Phe Pro Asn Phe Ile Val Arg Ala Ile Asn Lys
65                  70                  75                  80

Phe Pro Lys Leu Ser Leu Cys Ser Lys Arg Phe Glu Ser Glu Gln Tyr
                85                  90                  95

Ser Lys Lys Ile Asn Gly Ser Met Lys Gly Ser Val Glu Phe Ile Gly
            100                 105                 110

Phe Trp Gln Asn Glu Arg Tyr Phe Leu Glu His Lys Glu Lys Leu Arg
        115                 120                 125

Glu Ile Phe Thr Pro Ile Asn Ile Asn Leu Asp Ala Lys Glu Leu Ser
    130                 135                 140

Asp Val Ile Arg Cys Thr Asn Ser Val Ser Val His Ile Arg Arg Gly
145                 150                 155                 160

Asp Tyr Val Ser Asn Val Glu Ala Leu Lys Ile His Gly Leu Cys Thr
                165                 170                 175

Glu Arg Tyr Tyr Ile Asp Ser Ile Arg Tyr Leu Lys Glu Arg Phe Asn
            180                 185                 190

Asn Leu Val Phe Phe Val Phe Ser Asp Asp Ile Glu Trp Cys Lys Lys
        195                 200                 205

Tyr Lys Asn Glu Ile Phe Ser Arg Ser Asp Val Lys Phe Ile Glu
    210                 215                 220

Gly Asn Thr Gln Glu Val Asp Met Trp Leu Met Ser Asn Ala Lys Tyr
```

```
            225                 230                 235                 240

His Ile Ile Ala Asn Ser Ser Phe Ser Trp Trp Gly Ala Trp Leu Lys
                        245                 250                 255

Asn Tyr Asp Leu Gly Ile Thr Ile Ala Pro Thr Pro Trp Phe Glu Arg
                        260                 265                 270

Glu Glu Leu Asn Ser Phe Asp Pro Cys Pro Lys Trp Val Arg Ile
                275                 280                 285

Glu Lys
            290

<210> SEQ ID NO 11
<211> LENGTH: 289
<212> TYPE: PRT
<213> ORGANISM: Bacteroides fragilis

<400> SEQUENCE: 11

Met Phe Phe Arg Cys Cys Met Lys Ile Val Gln Ile Ile Gly Gly Leu
        1               5                   10                  15

Gly Asn Gln Met Phe Gln Phe Ala Phe Tyr Leu Ala Leu Lys Glu Lys
                        20                  25                  30

Tyr Val Asn Val Lys Leu Asp Thr Ser Ser Phe Gly Ala Tyr Thr His
                    35                  40                  45

Asn Gly Phe Glu Leu Asp Lys Val Phe His Val Glu Tyr Leu Lys Ala
        50                  55                  60

Ser Ile Arg Glu Arg Ile Lys Leu Ser Tyr Gln Gly Ser Glu Ile Trp
        65                  70                  75                  80

Ile Arg Val Leu Arg Lys Leu Leu Lys Arg Lys Lys Thr Glu Tyr Val
                        85                  90                  95

Glu Pro Tyr Leu Cys Phe Asp Glu Asn Ala Ile Ser Leu Ser Cys Asp
                    100                 105                 110

Lys Tyr Tyr Ile Gly Tyr Trp Gln Ser Tyr Lys Tyr Phe Thr Asn Ile
                    115                 120                 125

Glu Ala Ala Ile Arg Gly Gln Phe His Phe Ser Lys Val Leu Ser Asp
                130                 135                 140

Lys Asn Glu Phe Ile Lys Lys Gln Met Gln Asn Ser Asn Ser Val Ser
        145                 150                 155                 160

Leu His Val Arg Leu Gly Asp Tyr Val Asn Asn Pro Ala Tyr Ser Asn
                        165                 170                 175

Ile Cys Thr Ser Ala Tyr Tyr Asn Lys Ala Ile Asn Ile Gln Ser
                    180                 185                 190

Lys Val Ser Glu Pro Lys Phe Phe Val Phe Ser Asp Thr Val Trp
                    195                 200                 205

Cys Lys Asp His Leu Lys Ile Pro Asn Cys His Ile Ile Asp Trp Asn
                210                 215                 220

Asn Lys Glu Glu Ser Tyr Trp Asp Met Cys Leu Met Thr Tyr Cys Lys
        225                 230                 235                 240

His Asn Ile Ile Ala Asn Ser Ser Phe Ser Trp Trp Gly Ala Trp Leu
                        245                 250                 255

Asn Thr Asn Pro Glu Arg Ile Val Ile Ala Pro Gly Lys Trp Ile Asn
                        260                 265                 270

Asp Asp Arg Val Gln Val Ser Asp Ile Ile Pro Ser Asp Trp Ile Cys
                275                 280                 285

Val
```

<210> SEQ ID NO 12
<211> LENGTH: 287
<212> TYPE: PRT
<213> ORGANISM: Bacteroides fragilis

<400> SEQUENCE: 12

Met Leu Tyr Val Ile Leu Arg Gly Arg Leu Gly Asn Asn Leu Phe Gln
1               5                   10                  15

Ile Ala Thr Ala Ala Ser Leu Thr Gln Asn Phe Ile Phe Cys Thr Val
            20                  25                  30

Asn Lys Asp Gln Glu Arg Gln Val Leu Leu Tyr Lys Asp Ser Phe Phe
        35                  40                  45

Lys Asn Ile Lys Val Met Lys Gly Val Pro Asp Gly Ile Pro Tyr Tyr
50                  55                  60

Lys Glu Pro Phe His Glu Phe Ser Arg Ile Pro Tyr Glu Gly Lys
65                  70                  75                  80

Asp Leu Ile Ile Asp Gly Tyr Phe Gln Ser Glu Lys Tyr Phe Lys Arg
                85                  90                  95

Ser Val Val Leu Asp Leu Tyr Arg Ile Thr Asp Glu Leu Arg Lys Lys
            100                 105                 110

Ile Trp Asn Ile Cys Gly Asn Ile Leu Glu Lys Gly Thr Val Ser
        115                 120                 125

Ile His Val Arg Arg Gly Asp Tyr Leu Lys Leu Pro His Ala Leu Pro
130                 135                 140

Phe Cys Gly Lys Ser Tyr Tyr Lys Asn Ala Ile Gln Tyr Ile Gly Glu
145                 150                 155                 160

Asp Lys Ile Phe Ile Ile Cys Ser Asp Asp Ile Asp Trp Cys Lys Lys
                165                 170                 175

Asn Phe Ile Gly Lys Arg Tyr Tyr Phe Ile Glu Asn Thr Thr Pro Leu
            180                 185                 190

Leu Asp Leu Tyr Ile Gln Ser Leu Cys Thr His Asn Ile Ile Ser Asn
        195                 200                 205

Ser Ser Phe Ser Trp Trp Gly Ala Trp Leu Asn Glu Asn Ser Asn Lys
210                 215                 220

Ile Val Ile Ala Pro Gln Met Trp Phe Gly Ile Ser Val Lys Leu Gly
225                 230                 235                 240

Val Ser Asp Leu Leu Pro Val Ser Trp Val Arg Leu Pro Asn Asn Tyr
                245                 250                 255

Thr Leu Gly Arg Tyr Cys Phe Ala Leu Tyr Lys Val Val Glu Asp Tyr
            260                 265                 270

Leu Leu Asn Ile Leu Arg Leu Ile Trp Lys Arg Lys Lys Asn Met
        275                 280                 285

<210> SEQ ID NO 13
<211> LENGTH: 1583
<212> TYPE: DNA
<213> ORGANISM: Artificial Sequence
<220> FEATURE:
<223> OTHER INFORMATION: Genomic DNA sequence of the PlacIq lacY+
      chromosomal construct derived from Escherichia coli

<400> SEQUENCE: 13
caccatcgaa tggcgcaaaa cctttcgcgg tatggcatga tagcgcccgg aagagagtca      60
agtgtaggct ggagctgctt cgaagttcct atactttcta gagaatagga acttcggaat     120
aggaacttcg gaataggaac taaggaggat attcatatgt actatttaaa aaacacaaac     180
ttttggatgt tcggtttatt cttttttctt tacttttta tcatgggagc ctacttcccg     240

```
tttttcccga tttggctaca tgacatcaac catatcagca aaagtgatac gggtattatt      300
tttgccgcta tttctctgtt ctcgctatta ttccaaccgc tgtttggtct gctttctgac      360
aaactcgggc tgcgcaaata cctgctgtgg attattaccg gcatgttagt gatgtttgcg      420
ccgttcttta tttttatctt cgggccactg ttacaataca acattttagt aggatcgatt      480
gttggtggta tttatctagg cttttgtttt aacgccggtg cgccagcagt agaggcattt      540
attgagaaag tcagccgtcg cagtaatttc gaatttggtc gcgcgcggat gtttggctgt      600
gttggctggg cgctgtgtgc ctcgattgtc ggcatcatgt tcaccatcaa taatcagttt      660
gttttctggc tgggctctgg ctgtgcactc atcctcgccg ttttactctt tttcgccaaa      720
acggatgcgc cctcttctgc cacggttgcc aatgcggtag gtgccaacca ttcggcattt      780
agccttaagc tggcactgga actgttcaga cagccaaaac tgtggttttt gtcactgtat      840
gttattggcg tttcctgcac ctacgatgtt tttgaccaac agtttgctaa tttctttact      900
tcgttctttg ctaccggtga acagggtacg cgggtatttg gctacgtaac gacaatgggc      960
gaattactta acgcctcgat tatgttcttt gcgccactga tcattaatcg catcggtggg     1020
aaaaacgccc tgctgctggc tggcactatt atgtctgtac gtattattgg ctcatcgttc     1080
gccacctcag cgctggaagt ggttattctg aaaacgctgc atatgtttga agtaccgttc     1140
ctgctggtgg gctgctttaa atatattacc agccagtttg aagtgcgttt ttcagcgacg     1200
atttatctgg tctgtttctg cttctttaag caactggcga tgatttttat gtctgtactg     1260
gcgggcaata tgtatgaaag catcggtttc cagggcgctt atctggtgct gggtctggtg     1320
gcgctgggct tcaccttaat ttccgtgttc acgcttagcg gccccggccc gctttccctg     1380
ctgcgtcgtc aggtgaatga agtcgcttaa gcaatcaatg tcggatgcgg cgcgagcgcc     1440
ttatccgacc aacatatcat aacggagtga tcgcattgta aattataaaa attgcctgat     1500
acgctgcgct tatcaggcct acaagttcag cgatctacat tagccgcatc cggcatgaac     1560
aaagcgcagg aacaagcgtc gca                                              1583
```

<210> SEQ ID NO 14
<211> LENGTH: 2070
<212> TYPE: DNA
<213> ORGANISM: Artificial Sequence
<220> FEATURE:
<223> OTHER INFORMATION: Sequence of the chromosomal region derived from
      Escherichia coli bearing the (delta)wcaJ::FRT mutation

<400> SEQUENCE: 14

```
gttcggttat atcaatgtca aaaacctcac gccgctcaag ctggtgatca actccgggaa       60
cggcgcagcg ggtccggtgg tggacgccat gaagcccgc tttaaagccc tcggcgcgcc      120
cgtggaatta atcaaagtgc acaacacgcc ggacggcaat ttccccaacg gtattcctaa      180
cccactactg ccggaatgcc gcgacgacac ccgcaatgcg gtcatcaaac acggcgcgga      240
tatgggcatt gcttttgatg gcgattttga ccgctgtttc ctgtttgacg aaaaagggca      300
gtttattgag ggctactaca ttgtcggcct gttggcagaa gcattcctcg aaaaaaatcc      360
cggcgcgaag atcatccacg atccacgtct ctcctggaac accgttgatg tggtgactgc      420
cgcaggtggc acgccggtaa tgtcgaaaac cggacacgcc tttattaaag aacgtatgcg      480
caaggaagac gccatctatg gtggcgaaat gagcgcccac cattacttcc gtgatttcgc      540
ttactgcgac agcggcatga tcccgtggct gctggtcgcc gaactggtgt gcctgaaaga      600
taaaacgctg ggcgaactgg tacgcgaccg gatggcggcg tttccggcaa gcggtgagat      660
```

```
caacagcaaa ctggcgcaac ccgttgaggc gattaaccgc gtggaacagc attttagccg      720
tgaggcgctg gcggtggatc gcaccgatgg catcagcatg acctttgccg actggcgctt      780
taacctgcgc acctccaata ccgaaccggt ggtgcgcctg aatgtggaat cgcgcggtga      840
tgtgccgctg atggaagcgc gaacgcgaac tctgctgacg ttgctgaacg agtaatgtcg      900
gatcttccct taccccactg cgggtaaggg gctaataaca ggaacaacga tgattccggg      960
gatccgtcga cctgcagttc gaagttccta ttctctagaa agtataggaa cttcgaagca     1020
gctccagcct acagttaaca agcggcata ttgatatgag cttacgtgaa aaaaccatca      1080
gcggcgcgaa gtggtcggcg attgccacgg tgatcatcat cggcctcggg ctggtgcaga     1140
tgaccgtgct ggcgcggatt atcgacaacc accagttcgg cctgcttacc gtgtcgctgg     1200
tgattatcgc gctggcagat acgctttctg acttcggtat cgctaactcg attattcagc     1260
gaaaagaaat cagtcacctt gaactcacca cgttgtactg gctgaacgtc gggctgggga     1320
tcgtggtgtg cgtggcggtg tttttgttga gtgatctcat cggcgacgtg ctgaataacc     1380
cggacctggc accgttgatt aaaacattat cgctggcgtt tgtggtaatc ccccacgggc     1440
aacagttccg cgcgttgatg caaaaagagc tggagttcaa caaaatcggc atgatcgaaa     1500
ccagcgcggt gctggcgggc ttcacttgta cggtggttag cgcccatttc tggccgctgg     1560
cgatgaccgc gatcctcggt tatctggtca atagtgcggt gagaacgctg ctgtttggct     1620
actttggccg caaaatttat cgccccggtc tgcatttctc gctggcgtcg gtggcaccga     1680
acttacgctt tggtgcctgg ctgacggcgg acagcatcat caactatctc aataccaacc     1740
tttcaacgct cgtgctggcg cgtattctcg gcgcgggcgt ggcaggggga tacaacctgg     1800
cgtacaacgt ggccgttgtg ccaccgatga agctgaaccc aatcatcacc cgcgtgttgt     1860
ttccggcatt cgccaaaatt caggacgata ccgaaaagct gcgtgttaac ttctacaagc     1920
tgctgtcggt agtggggatt atcaactttc cggcgctgct cgggctaatg gtggtgtcga     1980
ataactttgt accgctggtc tttggtgaga agtggaacag cattattccg gtgctgcaat     2040
tgctgtgtgt ggtgggtctg ctgcgctccg                                      2070
```

<210> SEQ ID NO 15  
<211> LENGTH: 5046  
<212> TYPE: DNA  
<213> ORGANISM: Artificial Sequence  
<220> FEATURE:  
<223> OTHER INFORMATION: Genomic DNA sequence surrounding the lacZ+ insertion into the lon region derived from Escherichia coli

<400> SEQUENCE: 15

```
gtggatggaa gaggtggaaa aagtggttat ggaggagtgg gtaattgatg gtgaaaggaa       60
agggttggtg atttatggga aggggaagg ggaagaggga tgtggtgaat aattaaggat      120
tgggatagaa ttagttaagg aaaaaggggg gatttatgt ggggtttaat ttttggtgta      180 ttgtggggt tgaatgtggg ggaaagatgg ggatatagtg aggtagatgt taatagatgg      240
ggtgaaggag agtggtgtga tgtgattagg tgggggaaat taaagtaaga gagaggtgta     300 tgattgggg gatgggtgga ggtggagttg gaagttggta ttgtgtagaa agtataggaa      360
gttgagaggg gttttgaagg tgagggtggg ggaaggagtg aggggggaag gggtggtaaa     420 ggaagggaa gaggtagaaa gggagtgggg agaaagggtg gtgaggggg atgaatgtga      480 ggtagtgggg tatgtggaga agggaaaagg gaagggaa gagaaaggag gtaggttgga      540
gtggggttag atggggatag gtagagtggg ggtttatg gagaggaagg gaaggggaat      600
```

```
tgggaggtgg ggggggggtgt ggtaaggttg ggaaggggtg gaaagtaaag tggatgggtt    660 tgttggggggg aaggatgtga tggggggaggg gatgaagatg tgatgaagag agaggatgag   720
gatggtttgg gatgattgaa gaagatggat tggagggagg ttgtgggggg ggttgggtgg    780
agagggtatt ggggtatgag tggggagaag agagaatggg gtggtgtgat gggggggtgt    840
tgggggtgtg agggagggg gggggggttg tttttgtgaa gagggaggtg tggggtgggg    900
tgaatgaagt ggaggaggag ggaggggggg tatggtgggt ggggaggagg gggttggtt    960 ggggaggtgt ggtggaggtt gtgagtgaag gggaaggga gtggtgggta ttgggggaag   1020
tgggggggga ggatgtggtg tgatgtgagg ttggtggtgg ggagaaagta tggatgatgg   1080
gtgatggaat ggggggggtg gatagggttg atggggggtag gtgggattg gaggaggaag   1140 ggaaagatgg gatggaggga ggaggtagtg ggatggaagg gggtgttgtg gatgaggatg   1200
atgtggagga agaggatgag ggggtggggg gaggggaagt gttggggagg gtgaagggg   1260 gatgggggag ggggaggatg tggtggtgag ggatggggat gggtggttgg ggaatatgat   1320
ggtggaaaat gggggggtttt gtggattgat ggagtgtggg ggggtgggtg tggggagggg   1380
gtatgaggag atagggttgg gtaggggtga tattggtgaa gaggttgggg gggaatgggg   1440 tgagggggttg gtggtggttt agggtatggg gggtggggat tggagggga tggggttgta   1500 tggggttgtt gaggagttgt tgtaataagg ggatgttgaa gttggtattg ggaagttggt   1560
attgtgtaga aagtatagga agttggaagg aggtggaggg tagataaagg ggggggttat   1620
ttttgagagg agaggaagtg gtaatggtag ggagggggg tgaggtggaa ttggggggat   1680 agtgagggggg tggaggagtg gtggggagga atggggatat ggaaagggtg gatattgagg   1740
gatgtgggtt gttgggggtg gaggagatgg ggatgggtgg tttggatgag ttggtgttga   1800 gtgtagggggg tgatgttgaa gtggaagtgg ggggggagt ggtgtgggg ataattgaat   1860 tgggggggtgg gggaggggag agggttttgg gtgggggaaga ggtagggggt atagatgttg   1920
agaatgggag atgggagggg tgaaaagagg ggggagtaag ggggtgggga tagttttgtt   1980
gggggggtaa tggagggagg tttaggggggt gtggtaggtg ggggaggtgg gagttgaggg   2040
gaatgggggg gggatggggt gtatggtgg ggagttgaag atgaagggta atgggggattt   2100 gaggagtagg atgaatgggg taggttttgg gggtgataaa taaggttttg gggtgatggt   2160 gggagggggtg aggggtggta atgaggaggg gatgaggaag tgtatgtggg gtggagtgga   2220
agaagggtgg ttggggggtgg taatggggggg ggggggttgga ggggttggagg gaggggttag   2280 ggtgaatggg ggtgggttga gttagggggaa tgtggttatg gaggggtgga ggggtgaagt   2340
gatgggggag gggggtgagg agttgttttt tatggggaat ggagatgtgt gaaagaaagg   2400
gtgagtgggg gttaaattgg gaaggttat tagggaggtg gatggaaaaa tggattttggg   2460 tggtggtgag atggggggatg gggtgggagg gggggggggag ggtgagagtg aggttttggg   2520 ggagaggga gtggtgggag gggtgatgt ggggggggttg tgaggatggg gtgggttgg    2580 gttggagtag gggtagtgtg agggagagtt gggggggggt gtggggtgg ggtagttgag   2640 ggagttgaat gaagtgttta ggttgtggag ggagatggag agggagttga ggggttggga   2700 ggggggttagg atgaggggg aggatggagt ggaggaggtt gttatgggta tgagggaaga   2760
ggtattgggt ggtgagttgg atggtttggg gggataaagg gaagtggaaa aagtggtggt   2820 ggtgttttg ttgggtgagg ggtggatggg ggtgggggtg gggaaagagg agagggttga   2880
tagagaagtg gggatggttg gggtatggg gaaaatgagg ggggtaaggg gaggagggt   2940
```

```
tggggttttg atgatatttta atgagggagt gatggaggga gtgggagagg aagggggggt    3000
gtaaaggggg atagtgagga aagggtgggg agtatttagg gaaaggggga agagtgttag    3060
ggatggggtg ggggtattgg gaaaggatga ggggggggggt gtgtggaggt agggaaaggg    3120 atttttttgat ggaggatttg gggagagggg ggaaggggtg gtgttgatgg agggggggggt  3180 agatggggga aataatatgg gtgggggtgg tgtggggtgg ggggggttga tagtggaggg    3240 gggggggaagg atggagagat ttgatggagg gatagagggg gtggtgatta ggggggtggg   3300
gtgattgatt gggagggag gagatgatga gagtgggtg attaggatgg gggtggagga     3360
ttggggttag ggtttgggtg atgggggta gggagggggg atgatgggtg agaggattga    3420
ttgggaggat ggggtggggtt tgaatattgg gttgatggag gagatagagg gggtaggggt  3480
gggagagggt gtaggagagg ggatggttgg gataatggga agagggggagg gggttaaagt  3540 tgttgtggtt gatgaggagg atatggtgga ggatggtgtg gtgatggatg aggtgaggat    3600
ggagaggatg atggtggtga gggttaaggg gtggaatgag gaaggggttg ggttgaggga    3660
ggaggagagg atttttgaatg gggaggtggg ggaaagggag atgggagggt tgtggttgaa   3720
tgagggtggg gtgggggtg tggagttgaa ggagggggagg atagagattg gggatttggg   3780
gggtggagag tttggggttt tggaggttga gaggtagtgt gaggggatgg ggataaggag    3840
gagggtgatg gataatttga ggggggaaag gggggggtggg ggtggggagg tgggtttgag   3900
ggtgggataa agaagtgtt agggtaggt agtgagggaa gtgggggggag atgtgaagtt    3960 gagggtggag tagagggggg gtgaaatgat gattaaaggg agtgggaaga tggaaatggg    4020
tgatttgtgt agtgggttta tggaggaagg agaggtgagg gaaaatgggg gtgatggggg   4080
agatatggtg atgttggaga taagtgggggt gagtggaggg gaggaggatg aggggaggg   4140 ggttttgtgg gggggggtaaa aatgggtgga ggtgaaattg agagggggaaa ggagtgtggt 4200 gggggtaagg gagggagggg gggttggagg agagatgaaa ggggggagtta agggatgaa   4260 aaataattgg ggtgtggggt tggtgtaggg aggtttgatg aagattaaat gtgaggagt    4320 aagaagggt gggattgtgg gtgggaagaa agggggggatt gagggtaatg ggataggtga   4380
ggttggtgta gatggggga tggtaagggt ggatgtggga gtttgagggg aggaggagag    4440 tatggggtg aggaagatgg gagggagggga ggtttggggg agggggttgtg gtgggggaaa  4500 ggagggaaag ggggattggg gattgagggt ggggaagtgt tggaaggggg gatggtgggg   4560
ggggtgttgg gtattagggg aggtgggggaa aggggggatgt ggtggaaggg gattaagttg  4620 ggtaaggggga gggttttggg agtgaggagg ttgtaaaagg agggggagtg aatgggtaat   4680
gatggtgata gtaggtttgg tgaggttgtg agtggaaaat agtgaggtgg gggaaaatgg   4740
agtaataaaa agaggggtgg gagggtaatt gggggttggg agggtttttt tgtgtgggta    4800
agttagatgg gggatggggg ttgggggttat aagggggtgt tgtaagggga tgggtggggt  4860
gatataagtg gtgggggttg gtaggttgaa ggattgaagt gggatataaa ttataaagag   4920
gaagagaaga gtgaataaat gtgaattgat ggagaagatt ggtggagggg gtgatatgtg   4980
taaaggtggg ggtgggggtg ggttagatgg tattattggt tgggtaagtg aatgtgtgaa    5040
agaagg                                                              5046
```

<210> SEQ ID NO 16
<211> LENGTH: 6199
<212> TYPE: DNA
<213> ORGANISM: Artificial Sequence
<220> FEATURE:
<223> OTHER INFORMATION: plasmid pG204

<400> SEQUENCE: 16

```
aattctaaaa attgattgaa tgtatgcaaa taaatgcata caccataggt gtggtttaat    60
ttgatgccct ttttcagggc tggaatgtgt aagagcgggg ttatttatgc tgttgttttt   120
ttgttactcg ggaagggctt tacctcttcc gcataaacgc ttccatcagc gtttatagtt   180
aaaaaaatct ttcggaactg gttttgcgct taccccaacc aacaggggat tgctgctttt   240
ccattgagcc tgtttctctg cgcgacgttc gcggcggcgt gtttgtgcat ccatctggat   300
tctcctgtca gttagctttg tggtgtgtg gcagttgtag tcctgaacga aaaccccccg    360
cgattggcac attggcagct aatccggaat cgcacttacg gccaatgctt cgtttcgtat   420
cacacacccc aaagccttct gctttgaatg ctgcccttct tcagggctta attttaaga    480
gcgtcacctt catggtggtc agtgcgtcct gctgatgtgc tcagtatcac cgccagtggt   540
atttatgtca acaccgccag agataattta tcaccgcaga tggttatctg tatgtttttt   600
atatgaattt attttttgca gggggcatt gtttggtagg tgagagatca attctgcatt   660
aatgaatcgg ccaacgcgcg gggagaggcg gtttgcgtat tgggcgctct tccgcttcct   720
cgctcactga ctcgctgcgc tcggtcgttc ggctgcggcg agcggtatca gctcactcaa   780
aggcggtaat acggttatcc acagaatcag gggataacgc aggaaagaac atgtgagcaa   840
aaggccagca aaaggccagg aaccgtaaaa aggccgcgtt gctggcgttt ttccataggc   900
tccgcccccc tgacgagcat cacaaaaatc gacgctcaag tcagaggtgg cgaaacccga   960
caggactata aagataccag gcgtttcccc ctggaagctc cctcgtgcgc tctcctgttc  1020
cgaccctgcc gcttaccgga tacctgtccg cctttctccc ttcgggaagc gtggcgcttt  1080
ctcatagctc acgctgtagg tatctcagtt cggtgtaggt cgttcgctcc aagctgggct  1140
gtgtgcacga accccccgtt cagcccgacc gctgcgcctt atccggtaac tatcgtcttg  1200
agtccaaccc ggtaagacac gacttatcgc cactggcagc agccactggt aacaggatta  1260
gcagagcgag gtatgtaggc ggtgctacag agttcttgaa gtggtggcct aactacggct  1320
acactagaag gacagtattt ggtatctgcg ctctgctgaa gccagttacc ttcggaaaaa  1380
gagttggtag ctcttgatcc ggcaaacaaa ccaccgctgg tagcggtggt ttttttgttt  1440
gcaagcagca gattacgcgc agaaaaaaag gatctcaaga agatcctttg atctttcta   1500
cggggtctga cgctcagtgg aacgaaaact cacgttaagg gattttggtc atgagattat  1560
caaaaaggat cttcacctag atccttttaa attaaaaatg aagttttaaa tcaatctaaa  1620
gtatatatga gtaaacttgg tctgacagtt accaatgctt aatcagtgag gcacctatct  1680
cagcgatctg tctatttcgt tcatccatag ttgcctgact ccccgtcgtg tagataacta  1740
cgatacggga gggcttacca tctggcccca gtgctgcaat gataccgcga gacccacgct  1800
caccggctcc agatttatca gcaataaacc agccagccgg aagggccgag cgcagaagtg  1860
gtcctgcaac tttatccgcc tccatccagt ctattaattg ttgccgggaa gctagagtaa  1920
gtagttcgcc agttaatagt ttgcgcaacg ttgttgccat tgctacaggc atcgtggtgt  1980
cacgctcgtc gtttggtatg gcttcattca gctccggttc ccaacgatca aggcgagtta  2040
catgatcccc catgttgtgc aaaaaagcgg ttagctcctt cggtcctccg atcgttgtca  2100
gaagtaagtt ggccgcagtg ttatcactca tggttatggc agcactgcat aattctctta  2160
ctgtcatgcc atccgtaaga tgcttttctg tgactggtga gtactcaacc aagtcattct  2220
gagaatagtg tatgcggcga ccgagttgct cttgcccggc gtcaatacgg gataataccg  2280
```

```
cgccacatag cagaacttta aaagtgctca tcattggaaa acgttcttcg gggcgaaaac    2340
tctcaaggat cttaccgctg ttgagatcca gttcgatgta acccactcgt gcacccaact    2400
gatcttcagc atcttttact ttcaccagcg tttctgggtg agcaaaaaca ggaaggcaaa    2460
atgccgcaaa aaagggaata agggcgacac ggaaatgttg aatactcata ctcttccttt    2520
ttcaatatta ttgaagcatt tatcagggtt attgtctcat gagcggatac atatttgaat    2580
gtatttagaa aaataaacaa ataggggttc cgcgcacatt tccccgaaaa gtgccacctg    2640
acgtctaaga aaccattatt atcatgacat taacctataa aaataggcgt atcacgaggc    2700
cctttcgtct cgcgcgtttc ggtgatgacg gtgaaaacct ctgacacatg cagctcccgg    2760
agacggtcac agcttgtctg taagcggatg ccggagcag  acaagcccgt cagggcgcgt    2820
cagcgggtgt tggcgggtgt cggggctggc ttaactatgc ggcatcagag cagattgtac    2880
tgagagtgca ccatatatgc ggtgtgaaat accgcacaga tgcgtaagga gaaaataccg    2940
catcaggcgc ctcctcaacc tgtatattcg taaaccacgc ccaatgggag ctgtctcagg    3000
tttgttcctg attggttacg gcgcgtttcg catcattgtt gagttttcc gccagcccga    3060 cgcgcagttt accggtgcct gggtgcagta catcagcatg gggcaaattc tttccatccc    3120
gatgattgtc gcgggtgtga tcatgatggt ctgggcatat cgtcgcagcc cacagcaaca    3180
cgtttcctga ggaaccatga aacagtattt agaactgatg caaaaagtgc tcgacgaagg    3240
cacacagaaa aacgaccgta ccggaaccgg aacgctttcc attttggtc atcagatgcg    3300 ttttaacctg caagatggat tcccgctggt gacaactaaa cgttgccacc tgcgttccat    3360
catccatgaa ctgctgtggt ttctgcaggg cgacactaac attgcttatc tacacgaaaa    3420
caatgtcacc atctgggacg aatgggccga tgaaacggc gacctcgggc cagtgtatgg    3480
taaacagtgg cgcgcctggc caacgccaga tggtcgtcat attgaccaga tcactacggt    3540
actgaaccag ctgaaaaacg acccggattc gcgccgcatt attgtttcag cgtggaacgt    3600
aggcgaactg gataaaatgg cgctggcacc gtgccatgca ttcttccagt tctatgtggc    3660
agacggcaaa ctctcttgcc agctttatca gcgctcctgt gacgtcttcc tcggcctgcc    3720
gttcaacatt gccagctacg cgttattggt gcatatgatg cgcagcagt gcgatctgga    3780 agtgggtgat tttgtctgga ccggtggcga cacgcatctg tacagcaacc atatggatca    3840
aactcatctg caattaagcc gcgaaccgcg tccgctgccg aagttgatta tcaaacgtaa    3900
acccgaatcc atcttcgact accgtttcga agactttgag attgaaggct acgatccgca    3960
tccgggcatt aaagccggg tggctatcta attacgaaac atcctgccag agccgacgcc    4020
agtgtgcgtc ggtttttta ccctccgtta aattcttcga gacgccttcc cgaaggcgcc    4080
attcgccatt caggctgcgc aactgttggg aagggcgatc ggtgcgggcc tcttcgctat    4140
tacgccagct ggcgaaaggg ggatgtgctg caaggcgatt aagttgggta acgccagggt    4200
tttcccagtc acgacgttgt aaaacgacgg ccagtgccaa gctttcttta atgaagcagg    4260
gcatcaggac ggtatctttg tggagaaagc agagtaatct tattcagcct gactggtggg    4320
aaaccaccag tcagaatgtg ttagcgcatg ttgacaaaaa taccattagt cacattatcc    4380
gtcagtcgga cgacatggta gataacctgt ttattatgcg ttttgatctt acgtttaata    4440 ttaccttat gcgatgaaac ggtcttggct ttgatattca tttggtcaga gatttgaatg    4500
gttccctgac ctgccatcca cattcgcaac atactcgatt cggttcgct caatgataac    4560 gtcggcatat ttaaaaacga ggttatcgtt gtctcttttt tcagaatatc gccaaggata    4620
tcgtcgagag attccggttt aatcgattta gaactgatca ataaattttt tctgaccaat    4680
```

```
agatattcat caaaatgaac attggcaatt gccataaaaa cgataaataa cgtattggga   4740
tgttgattaa tgatgagctt gatacgctga ctgttagaag catcgtggat gaaacagtcc   4800
tcattaataa acaccactga agggcgctgt gaatcacaag ctatggcaag gtcatcaacg   4860
gtttcaatgt cgttgatttc tcttttttta acccctctac tcaacagata cccggttaaa   4920
cctagtcggg tgtaactaca taaatccata ataatcgttg acatggcata ccctcactca   4980
atgcgtaacg ataattcccc ttacctgaat atttcatcat gactaaacgg aacaacatgg   5040
gtcacctaat gcgccactct cgcgattttt caggcggact tactatcccg taaagtgttg   5100
tataatttgc ctggaattgt cttaaagtaa agtaaatgtt gcgatatgtg agtgagctta   5160
aaacaaatat ttcgctgcag gagtatcctg aagatgttc gtgagaagct tactgctcac   5220
aagaaaaaag gcacgtcatc tgacgtgcct tttttatttg tactaccctg tacgattact   5280
gcagctcgag ctaacacgag ctatgtttat ccacgtttat ccagtgattg actatgggga   5340
tataagtatt ttttggagtt atatcgtacc aaggagtagg ataaataaca atctgtgacg   5400
ctgatgtacc taaataagcc ccccaccaac taaaactact attcgctata atatgatggt   5460
tagctaagct cattaaccat aaatcttctt cttgtgataa atcttctgaa taatatatat   5520
tatatttttt actgagtaat gtttcgatat tttctttaca ccaaaaaata tcatcactga   5580
aaataaacac gtcacgtatc attgccaaat cgcgtatttt atttaaagct ttttttgtaat  5640 actctaacga acaaacgcca tgagttaaag tagctgtttt gttttttata taatctcctc   5700
ttcttatatg aatagaaagt gatgattgag attcaagaat ttttgctgca agtaaatttg   5760
cttgttcaga cacattcttt ggaataaaaa attcttttag atctaatata tgtttatgga   5820
aaaagtgctc agattgccaa taccctatat atttttttgga tttccatttt tgcgctatat  5880
attcaaaatc ataaccatag gcatgaaatt cattgcaaaa acctaaaaaa agaaagattt   5940
caggatataa tcttgaccca cgaaccaaaa atttataaat attattaatt tttggtgtgt   6000
aatactgtaa atattcctct ggaatttgta gattgtttag cctgtaacca ccatgatcat   6060
cattttcagc ataatgactt atatcaaaat ataatggtgt cccattaatt ttggaaagcg   6120
catacccaaa tgagaactga aaagttgat ttccaagtcc gccttgtaat cttataatag    6180
acattatatc tccttcttg                                                6199
```

<210> SEQ ID NO 17
<211> LENGTH: 6170
<212> TYPE: DNA
<213> ORGANISM: Artificial Sequence
<220> FEATURE:
<223> OTHER INFORMATION: plasmid pG216

<400> SEQUENCE: 17

```
tctagaattc taaaaattga ttgaatgtat gcaaataaat gcatacacca taggtgtggt    60
ttaatttgat gccctttttc agggctggaa tgtgtaagag cggggttatt tatgctgttg   120 ttttttttgtt actcgggaag ggctttacct cttccgcata aacgcttcca tcagcgttta   180
tagttaaaaa aatctttcgg aactggtttt gcgcttaccc caaccaacag gggatttgct   240
gctttccatt gagcctgttt ctgcgcgcga cgttcgcggc ggcgtgtttg tgcatccatc   300
tggattctcc tgtcagttag ctttggtggt gtgtggcagt tgtagtcctg aacgaaaacc   360
ccccgcgatt ggcacattgg cagctaatcc ggaatcgcac ttacggccaa tgcttcgttt   420
cgtatcacac accccaaagc cttctgcttt gaatgctgcc cttcttcagg gcttaatttt   480
```

```
taagagcgtc accttcatgg tggtcagtgc gtcctgctga tgtgctcagt atcaccgcca    540
gtggtattta tgtcaacacc gccagagata atttatcacc gcagatggtt atctgtatgt    600
tttttatatg aatttatttt ttgcaggggg gcattgtttg gtaggtgaga gatcaattct    660
gcattaatga atcggccaac gcgcggggag aggcggtttg cgtattgggc gctcttccgc    720
ttcctcgctc actgactcgc tgcgctcggt cgttcggctg cggcgagcgg tatcagctca    780
ctcaaaggcg gtaatacggt tatccacaga atcaggggat aacgcaggaa agaacatgtg    840
agcaaaaggc cagcaaaagg ccaggaaccg taaaaaggcc gcgttgctgg cgttttttcca   900
taggctccgc cccctgacg agcatcacaa aaatcgacgc tcaagtcaga ggtggcgaaa     960
cccgacagga ctataaagat accaggcgtt tccccctgga agctccctcg tgcgctctcc    1020
tgttccgacc ctgccgctta ccggatacct gtccgccttt ctcccttcgg gaagcgtggc    1080
gctttctcat agctcacgct gtaggtatct cagttcggtg taggtcgttc gctccaagct    1140
gggctgtgtg cacgaacccc ccgttcagcc cgaccgctgc gccttatccg gtaactatcg    1200
tcttgagtcc aacccggtaa gacacgactt atcgccactg gcagcagcca ctggtaacag    1260
gattagcaga gcgaggtatg taggcggtgc tacagagttc ttgaagtggt ggcctaacta    1320
cggctacact agaaggacag tatttggtat ctgcgctctg ctgaagccag ttaccttcgg    1380
aaaaagagtt ggtagctctt gatccggcaa acaaaccacc gctggtagcg gtggtttttt    1440
tgtttgcaag cagcagatta cgcgcagaaa aaaaggatct caagaagatc ctttgatctt    1500
ttctacgggg tctgacgctc agtggaacga aaactcacgt taagggattt tggtcatgag    1560
attatcaaaa aggatcttca cctagatcct ttttaaattaa aaatgaagtt ttaaatcaat    1620
ctaaagtata tatgagtaaa cttggtctga cagttaccaa tgcttaatca gtgaggcacc    1680
tatctcagcg atctgtctat ttcgttcatc catagttgcc tgactccccg tcgtgtagat    1740
aactacgata cgggagggct taccatctgg ccccagtgct gcaatgatac cgcgagaccc    1800
acgctcaccg gctccagatt tatcagcaat aaaccagcca gccggaaggg ccgagcgcag    1860
aagtggtcct gcaactttat ccgcctccat ccagtctatt aattgttgcc gggaagctag    1920
agtaagtagt tcgccagtta atagtttgcg caacgttgtt gccattgcta caggcatcgt    1980
ggtgtcacgc tcgtcgtttg gtatggcttc attcagctcc ggttcccaac gatcaaggcg    2040
agttacatga tcccccatgt tgtgcaaaaa agcggttagc tccttcggtc ctccgatcgt    2100
tgtcagaagt aagttggccg cagtgttatc actcatggtt atggcagcac tgcataattc    2160
tcttactgtc atgccatccg taagatgctt ttctgtgact ggtgagtact caaccaagtc    2220
attctgagaa tagtgtatgc ggcgaccgag ttgctcttgc ccggcgtcaa tacgggataa    2280
taccgcgcca catagcagaa ctttaaaagt gctcatcatt ggaaaacgtt cttcggggcg    2340
aaaactctca aggatcttac cgctgttgag atccagttcg atgtaaccca ctcgtgcacc    2400
caactgatct tcagcatctt ttactttcac cagcgtttct gggtgagcaa aaacaggaag    2460
gcaaaatgcc gcaaaaaagg gaataagggc gacacggaaa tgttgaatac tcatactctt    2520
cctttttcaa tattattgaa gcatttatca gggttattgt ctcatgagcg gatacatatt    2580
tgaatgtatt tagaaaaata aacaaatagg ggttccgcgc acatttcccc gaaaagtgcc    2640
acctgacgtc taagaaacca ttattatcat gacattaacc tataaaaata ggcgtatcac    2700
gaggcccttt cgtctcgcgc gtttcggtga tgacggtgaa aacctctgac acatgcagct    2760
cccggagacg tcacagcttg tctgtaagc ggatgccggg agcagacaag cccgtcaggg    2820
cgcgtcagcg ggtgttggcg ggtgtcgggg ctggcttaac tatgcggcat cagagcagat    2880
```

```
tgtactgaga gtgcaccata tatgcggtgt gaaataccgc acagatgcgt aaggagaaaa    2940
taccgcatca ggcgcctcct caacctgtat attcgtaaac cacgcccaat gggagctgtc    3000
tcaggtttgt tcctgattgg ttacggcgcg tttcgcatca ttgttgagtt tttccgccag    3060
cccgacgcgc agtttaccgg tgcctgggtg cagtacatca gcatgggggca aattctttcc    3120 atcccgatga ttgtcgcggg tgtgatcatg atggtctggg catatcgtcg cagcccacag    3180
caacacgttt cctgaggaac catgaaacag tatttagaac tgatgcaaaa agtgctcgac    3240
gaaggcacac agaaaaacga ccgtaccgga accggaacgc tttccatttt tggtcatcag    3300
atgcgtttta acctgcaaga tggattcccg ctggtgacaa ctaaacgttg ccacctgcgt    3360
tccatcatcc atgaactgct gtggtttctg cagggcgaca ctaacattgc ttatctacac    3420
gaaaacaatg tcaccatctg ggacgaatgg gccgatgaaa acggcgacct cgggccagtg    3480
tatggtaaac agtggcgcgc ctggccaacg ccagatggtc gtcatattga ccagatcact    3540
acggtactga accagctgaa aaacgacccg gattcgcgcc gcattattgt ttcagcgtgg    3600
aacgtaggcg aactggataa aatggcgctg gcaccgtgcc atgcattctt ccagttctat    3660
gtggcagacg gcaaactctc ttgccagctt tatcagcgct cctgtgacgt cttcctcggc    3720
ctgccgttca acattgccag ctacgcgtta ttggtgcata tgatggcgca gcagtgcgat    3780
ctggaagtgg gtgattttgt ctggaccggt ggcgacacgc atctgtacag caaccatatg    3840
gatcaaactc atctgcaatt aagccgcgaa ccgcgtccgc tgccgaagtt gattatcaaa    3900
cgtaaacccg aatccatctt cgactaccgt ttcgaagact ttgagattga aggctacgat    3960
ccgcatccgg gcattaaagc gccggtggct atctaattac gaaacatcct gccagagccg    4020
acgccagtgt gcgtcggttt ttttaccctc cgttaaattc ttcgagacgc cttcccgaag    4080
gcgccattcg ccattcaggc tgcgcaactg ttgggaaggg cgatcggtgc gggcctcttc    4140
gctattacgc cagctggcga aagggggatg tgctgcaagg cgattaagtt gggtaacgcc    4200
agggttttcc cagtcacgac gttgtaaaac gacggccagt gccaagcttt ctttaatgaa    4260
gcagggcatc aggacggtat ctttgtggag aaagcagagt aatcttattc agcctgactg    4320
gtgggaaacc accagtcaga atgtgttagc gcatgttgac aaaaatacca ttagtcacat    4380
tatccgtcag tcggacgaca tggtagataa cctgtttatt atgcgttttg atcttacgtt    4440
taatattacc tttatgcgat gaaacggtct tggctttgat attcatttgg tcagagattt    4500
gaatggttcc ctgacctgcc atccacattc gcaacatact cgattcggtt cggctcaatg    4560
ataacgtcgg catatttaaa aacgaggtta tcgttgtctc ttttttcaga atatcgccaa    4620
ggatatcgtc gagagattcc ggtttaatcg atttagaact gatcaataaa ttttttctga    4680
ccaatagata ttcatcaaaa tgaacattgg caattgccat aaaaacgata ataacgtat    4740 tgggatgttg attaatgatg agcttgatac gctgactgtt agaagcatcg tggatgaaac    4800
agtcctcatt aataaacacc actgaagggc gctgtgaatc acaagctatg caaggtcat    4860 caacggtttc aatgtcgttg atttctcttt ttttaacccc tctactcaac agatacccgg    4920
ttaaacctag tcgggtgtaa ctacataaat ccataataat cgttgacatg catacctc     4980 actcaatgcg taacgataat tccccttacc tgaatatttc atcatgacta aacgaacaa    5040 catgggtcac ctaatgcgcc actctcgcga ttttcaggc ggacttacta tcccgtaaag    5100
tgttgtataa tttgcctgga attgtcttaa agtaaagtaa atgttgcgat atgtgagtga    5160
gcttaaaaca aatatttcgc tgcaggagta tcctggaaga tgttcgtaga agcttactgc    5220
```

```
tcacaagaaa aaaggcacgt catctgacgt gccttttta tttgtactac cctgtacgat    5280
tactgcagct cgagttagga tttcgtttcg aattgggatt cgattttaac ccagtctttg    5340
cacaggatgt tttcgttacc gtaaatccag tgggacggac caatgataat ttttccgga    5400 tttttgatca ggtaggctgc ccaccaggag taagtgctgt tagtgatgat accgtgtttg    5460
caagactgca tcagcatcat gtcccagtgg gctgcaccat cacgcgtcgt catgtcaaca    5520
aacgggtaac ccagatccag gttctgtacg aattccagat cctcgcagaa caggaacagt    5580
tccagatttt gaacacgttt tgccatatac gcaatggcgc gcagctggta ggagatgtcc    5640
agctgccagc ccaggcgcat gtaatcgcca cggcggatgt gaacgaacac agagttttc    5700 gcagccagga tctgggacag tttacgagag tactgttccg cgtgttcggt cgggtgaggc    5760
agggtgaaag tttgtttgat cagagggag atatcttcga aatagcgcgg gtcctgaaag    5820
tagccatgga aatacgcaat gcggctcggt tcaaacagtt ccggcatgta ctcgaataca    5880
atttctttgc taacgcggcc cagacccata cgacgcagtg caccacgcac cagacgcggc    5940
aggttctgca tgtgtgccgc ggcgatctgc tgggcggacg cacactgcag gtcgatcggg    6000
aacaggtgca ggcccagttc acggttaccg taatcgaacc aagtggtatc cagcagtacc    6060
ggaatgttca ggtgagtctg cagagattta gcgaatgcgt actggaacat ctggttaccc    6120
aggccgccgt gcacctgaac gattttgaaa tccattatat ctccttcttg              6170

<210> SEQ ID NO 18
<211> LENGTH: 6155
<212> TYPE: DNA
<213> ORGANISM: Artificial Sequence
<220> FEATURE:
<223> OTHER INFORMATION: plasmid pG217

<400> SEQUENCE: 18
tctagaattc taaaaattga ttgaatgtat gcaaataaat gcatacacca taggtgtggt      60
ttaatttgat gccctttttc agggctggaa tgtgtaagag cggggttatt tatgctgttg     120 ttttttttgtt actcgggaag ggctttacct cttccgcata aacgcttcca tcagcgttta     180
tagttaaaaa aatctttcgg aactggtttt gcgcttaccc caaccaacag gggatttgct     240
gctttccatt gagcctgttt ctctgcgcga cgttcgcggc ggcgtgtttg tgcatccatc     300
tggattctcc tgtcagttag cttggtggt gtgtggcagt tgtagtcctg aacgaaaacc     360
ccccgcgatt ggcacattgg cagctaatcc ggaatcgcac ttacggccaa tgcttcgttt     420
cgtatcacac accccaaagc cttctgcttt gaatgctgcc cttcttcagg gcttaatttt     480
taagagcgtc accttcatgg tggtcagtgc gtcctgctga tgtgctcagt atcaccgcca     540
gtggtattta tgtcaacacc gccagagata atttatcacc gcagatggtt atctgtatgt     600 ttttttatatg aatttatttt tgcaggggg gcattgttg gtaggtgaga gatcaattct     660
gcattaatga atcggccaac gcgcgggag aggcggtttg cgtattgggc gctcttccgc     720
ttcctcgctc actgactcgc tgcgctcggt cgttcggctg cggcgagcgg tatcagctca     780
ctcaaaggcg gtaatacggt tatccacaga atcaggggat aacgcaggaa agaacatgtg     840
agcaaaaggc cagcaaaagg ccaggaaccg taaaaaggcc gcgttgctgg cgttttcca      900 taggctccgc ccccctgacg agcatcacaa aaatcgacgc tcaagtcaga ggtggcgaaa     960
cccgacagga ctataaagat accaggcgtt tccccctgga agctccctcg tgcgctctcc    1020
tgttccgacc ctgccgctta ccggatacct gtccgccttt ctcccttcgg gaagcgtggc    1080
gctttctcat agctcacgct gtaggtatct cagttcggtg taggtcgttc gctccaagct    1140
```

```
gggctgtgtg cacgaacccc ccgttcagcc cgaccgctgc gccttatccg gtaactatcg    1200
tcttgagtcc aacccggtaa gacacgactt atcgccactg gcagcagcca ctggtaacag    1260
gattagcaga gcgaggtatg taggcggtgc tacagagttc ttgaagtggt ggcctaacta    1320
cggctacact agaaggacag tatttggtat ctgcgctctg ctgaagccag ttaccttcgg    1380
aaaaagagtt ggtagctctt gatccggcaa acaaaccacc gctggtagcg gtggtttttt    1440
tgtttgcaag cagcagatta cgcgcagaaa aaaggatct caagaagatc ctttgatctt    1500
ttctacgggg tctgacgctc agtggaacga aaactcacgt taagggattt tggtcatgag    1560
attatcaaaa aggatcttca cctagatcct tttaaattaa aaatgaagtt ttaaatcaat    1620
ctaaagtata tatgagtaaa cttggtctga cagttaccaa tgcttaatca gtgaggcacc    1680
tatctcagcg atctgtctat ttcgttcatc catagttgcc tgactccccg tcgtgtagat    1740
aactacgata cgggagggct taccatctgg ccccagtgct gcaatgatac cgcgagaccc    1800
acgctcaccg gctccagatt tatcagcaat aaaccagcca gccggaaggg ccgagcgcag    1860
aagtggtcct gcaactttat ccgcctccat ccagtctatt aattgttgcc gggaagctag    1920
agtaagtagt tcgccagtta atagtttgcg caacgttgtt gccattgcta caggcatcgt    1980
ggtgtcacgc tcgtcgtttg gtatggcttc attcagctcc ggttcccaac gatcaaggcg    2040
agttacatga tcccccatgt tgtgcaaaaa agcggttagc tccttcggtc ctccgatcgt    2100
tgtcagaagt aagttggccg cagtgttatc actcatggtt atggcagcac tgcataattc    2160
tcttactgtc atgccatccg taagatgctt ttctgtgact ggtgagtact caaccaagtc    2220
attctgagaa tagtgtatgc ggcgaccgag ttgctcttgc ccggcgtcaa tacgggataa    2280
taccgcgcca catagcagaa ctttaaaagt gctcatcatt ggaaaacgtt cttcggggcg    2340
aaaactctca aggatcttac cgctgttgag atccagttcg atgtaaccca ctcgtgcacc    2400
caactgatct tcagcatctt ttactttcac cagcgtttct gggtgagcaa aaacaggaag    2460
gcaaaatgcc gcaaaaaagg gaataagggc gacacggaaa tgttgaatac tcatactctt    2520 ccttttcaa tattattgaa gcatttatca gggttattgt ctcatgagcg gatacatatt    2580
tgaatgtatt tagaaaaata aacaaatagg ggttccgcgc acatttcccc gaaaagtgcc    2640
acctgacgtc taagaaacca ttattatcat gacattaacc tataaaaata ggcgtatcac    2700
gaggcccttt cgtctcgcgc gtttcggtga tgacggtgaa aacctctgac acatgcagct    2760
cccggagacg gtcacagctt gtctgtaagc ggatgccggg agcagacaag cccgtcaggg    2820
cgcgtcagcg ggtgttggcg ggtgtcgggg ctggcttaac tatgcggcat cagagcagat    2880
tgtactgaga gtgcaccata tatgcggtgt gaaataccgc acagatgcgt aaggagaaaa    2940
taccgcatca ggcgcctcct caacctgtat attcgtaaac cacgcccaat gggagctgtc    3000
tcaggtttgt tcctgattgg ttacggcgcg tttcgcatca ttgttgagtt tttccgccag    3060
cccgacgcgc agtttaccgg tgcctggtg cagtacatca gcatgggca aattcttcc     3120 atcccgatga ttgtcgcggg tgtgatcatg atggtctggg catatcgtcg cagcccacag    3180
caacacgttt cctgaggaac catgaaacag tatttagaac tgatgcaaaa agtgctcgac    3240
gaaggcacac agaaaaacga ccgtaccgga accggaacgc tttccatttt tggtcatcag    3300
atgcgtttta acctgcaaga tggattcccg ctggtgacaa ctaaacgttg ccacctgcgt    3360
tccatcatcc atgaactgct gtggtttctg cagggcgaca ctaacattgc ttatctacac    3420
gaaaacaatg tcaccatctg ggacgaatgg gccgatgaaa acggcgacct cgggccagtg    3480
```

```
tatggtaaac agtggcgcgc ctggccaacg ccagatggtc gtcatattga ccagatcact   3540
acggtactga accagctgaa aaacgacccg gattcgcgcc gcattattgt ttcagcgtgg   3600
aacgtaggcg aactggataa aatggcgctg gcaccgtgcc atgcattctt ccagttctat   3660
gtggcagacg gcaaactctc ttgccagctt tatcagcgct cctgtgacgt cttcctcggc   3720
ctgccgttca acattgccag ctacgcgtta ttggtgcata tgatggcgca gcagtgcgat   3780
ctggaagtgg gtgattttgt ctggaccggt ggcgacacgc atctgtacag caaccatatg   3840
gatcaaactc atctgcaatt aagccgcgaa ccgcgtccgc tgccgaagtt gattatcaaa   3900
cgtaaacccg aatccatctt cgactaccgt ttcgaagact tgagattga aggctacgat   3960
ccgcatccgg gcattaaagc gccggtggct atctaattac gaaacatcct gccagagccg   4020
acgccagtgt gcgtcggttt ttttacccctc cgttaaattc ttcgagacgc cttcccgaag   4080
gcgccattcg ccattcaggc tgcgcaactg ttgggaaggg cgatcggtgc gggcctcttc   4140
gctattacgc cagctggcga aaggggggatg tgctgcaagg cgattaagtt gggtaacgcc   4200
agggttttcc cagtcacgac gttgtaaaac gacggccagt gccaagcttt ctttaatgaa   4260
gcagggcatc aggacggtat ctttgtggag aaagcagagt aatcttattc agcctgactg   4320
gtgggaaacc accagtcaga atgtgttagc gcatgttgac aaaaatacca ttagtcacat   4380
tatccgtcag tcggacgaca tggtagataa cctgtttatt atgcgttttg atcttacgtt   4440
taatattacc tttatgcgat gaaacggtct tggctttgat attcatttgg tcagagattt   4500
gaatggttcc ctgacctgcc atccacattc gcaacatact cgattcggtt cggctcaatg   4560
ataacgtcgg catatttaaa aacgaggtta tcgttgtctc tttttttcaga atatcgccaa   4620
ggatatcgtc gagagattcc ggtttaatcg atttagaact gatcaataaa tttttttctga   4680
ccaatagata ttcatcaaaa tgaacattgg caattgccat aaaaacgata aataacgtat   4740
tgggatgttg attaatgatg agcttgatac gctgactgtt agaagcatcg tggatgaaac   4800
agtcctcatt aataaacacc actgaagggc gctgtgaatc acaagctatg gcaaggtcat   4860
caacggtttc aatgtcgttg atttctcttt ttttaaccccc tctactcaac agatacccgg   4920
ttaaacctag tcgggtgtaa ctacataaat ccataataat cgttgacatg gcatacccctc   4980
actcaatgcg taacgataat tcccccttacc tgaatatttc atcatgacta aacggaacaa   5040
catgggtcac ctaatgcgcc actctcgcga ttttttcaggc ggacttacta tcccgtaaag   5100
tgttgtataa tttgcctgga attgtcttaa agtaaagtaa atgttgcgat atgtgagtga   5160
gcttaaaaca aatatttcgc tgcaggagta tcctggaaga tgttcgtaga agcttactgc   5220
tcacaagaaa aaaggcacgt catctgacgt gccttttttta tttgtactac cctgtacgat   5280
tactgcagct cgagttagga taccggcact ttgatccaac cagtcgggta gatatccggt   5340
gcttcggagt gctggaacca acggctcggc acaataacag tcttatccat attagggttc   5400
agccaggcac cccaccaaga aaacgtgctg ttacaaatga tgtgatgttt gcaatgagac   5460
atcagcatca tatcctgcca ggagtcttca tcagtgttcc agtcaatata aaccgcattc   5520
tgcagtggca gattttcttt aacccacgcg atatcgtcgg agaagatata gtaagatggg   5580
ctagcaacac gacgggacat ttccgcgata gcattctggt aatacggcag ctggcacacg   5640
gaaccggtag tagcccagtg tttcggctgc agatagtcac cacgacgaat gtgcagggaa   5700
accgcgtttt catctttgtc caggattcca agcatgttca ggctgcggga atttgctttg   5760
ttcttatcaa aggtgaagga ttcacgcact tcgtctttga tatcagcgaa gaaacgctcg   5820
ctctgataga aaccttttaaa gtacagcagc ggccagaaat acttcttctc gaacgcacgc   5880
```

-continued

```
agagagttcg gcgcctgctt gcgttcgtag atttttttaa aaaacaggaa ttcgataact    5940
tttttcagcg gttggttgat gcagaattcg gtgtgcggca ggttgaacac gcggtgcatt    6000
tcgtaaccgt aatggacttt gtaatgcatc atgtcgctca ggtcgatacg gaccttcggg    6060
taatactttt tcatacgcag atagaaagca tagataaaca tctggttgcc cagaccgcca    6120
gtcactttga tcagacgcat tatatctcct tcttg                               6155
```